United States Patent
Pevarello et al.

(10) Patent No.: US 11,155,538 B2
(45) Date of Patent: Oct. 26, 2021

(54) BICYCLIC CX3CR1 RECEPTOR AGONISTS

(71) Applicants: Board of Regents, The University of Texas System, Austin, TX (US); Axxam S.p.A., Milan (IT)

(72) Inventors: Paolo Pevarello, Pavia (IT); William J. Ray, Houston, TX (US); Mary Hamby, Houston, TX (US); Yaima Luzardo Lightfoot, Pearland, TX (US); Philip Jones, Houston, TX (US); Russell Thomas, Siena (IT); Chiara Liberati, Milan (IT); Domenica Torino, Praia a Mare (IT); Valentina Cusano, Naples (IT); Francesco Piscitelli, Marina di Strongoli (IT); Ali Munaim Yousif, Aversa (IT); Silvia Bovolenta, Milan (IT)

(73) Assignees: Board of Regents, The University of Texas System, Austin, TX (US); Axxam S.p.A., Bresso (IT)

(*) Notice: Subject to any disclaimer, the term of this patent is extended or adjusted under 35 U.S.C. 154(b) by 0 days.

(21) Appl. No.: 16/937,005

(22) Filed: Jul. 23, 2020

(65) Prior Publication Data
US 2021/0024510 A1 Jan. 28, 2021

Related U.S. Application Data

(60) Provisional application No. 62/877,660, filed on Jul. 23, 2019.

(51) Int. Cl.
| | |
|---|---|
| *C07D 409/14* | (2006.01) |
| *C07C 233/78* | (2006.01) |
| *C07D 333/78* | (2006.01) |
| *C07D 409/12* | (2006.01) |

(52) U.S. Cl.
CPC .......... *C07D 409/14* (2013.01); *C07C 233/78* (2013.01); *C07D 333/78* (2013.01); *C07D 409/12* (2013.01)

(58) Field of Classification Search
CPC .................................................. C07D 409/14
See application file for complete search history.

(56) References Cited

U.S. PATENT DOCUMENTS

| 8,841,290 B2 * | 9/2014 | Schwink | A61P 3/04 514/217.04 |
|---|---|---|---|
| 2012/0015936 A1 | 1/2012 | Schwink | |
| 2012/0015943 A1 | 1/2012 | Blackburn | |
| 2012/0141471 A1 | 6/2012 | Salvino | |
| 2017/0044187 A1 | 2/2017 | Liu | |
| 2020/0062768 A1 | 2/2020 | Salvino | |

FOREIGN PATENT DOCUMENTS

WO 2021016449 1/2021

OTHER PUBLICATIONS

International Application No. PCT/US2020/043258; International Search Report and Written Opinion of the International Searching Authority, dated Dec. 22, 2020; 9 pages.
PubChem CID 95903032, N-[3-(Dimethylamino)propyl]-5,6,7,8-tetrahydronaphthalene-2-carboxamide, create date: Dec. 11, 2015 (Dec. 11, 2015), especially p. 2, formula., https://pubchem.ncbi.nlm.nih.gov/compound/95903032.

* cited by examiner

*Primary Examiner* — Golam M Shameem
(74) *Attorney, Agent, or Firm* — Dennis A. Bennett; Lauren L. Stevens; Cynthia Hathaway

(57) ABSTRACT

Disclosed herein are novel cycloalka[b]heteroaryl compounds having CX3CR1/fractalkine receptor (CX3CR1) agonistic properties, pharmaceutical compositions comprising these compounds, chemical processes for preparing these compounds and their use in the treatment or prophylaxis of diseases associated with CX3CR1 receptor activity in animals, in particular humans.

17 Claims, 2 Drawing Sheets

BICYCLIC CX3CR1 RECEPTOR AGONISTS

This application claims the benefit of priority of U.S. Provisional Application No. 62/877,660, filed Jul. 23, 2019, the disclosure of which is hereby incorporated by reference as if written herein in its entirety.

Disclosed herein are novel bicyclic, e.g., cycloalka[b] heteroaryl compounds having CX3CR1/fractalkine receptor (CX3CR1) agonistic properties, pharmaceutical compositions comprising these compounds, chemical processes for preparing these compounds and their use in the treatment or prophylaxis of diseases associated with CX3CR1 receptor activity in animals, in particular humans.

Although neuroinflammation in the aging brain has been recognized for many years, only recently have human genetic studies demonstrated that activated microglia are not passive bystanders to neurodegeneration, but actively contribute to the pathogenesis. Microglia play both beneficial and potentially damaging roles in the CNS and fractalkine (FKN; CX3CL1) signalling is a principal means of neuron-to-microglial communication and thus is a strong candidate target for therapeutic exploration. FKN is a large membrane-anchored or secreted cytokine and is the only member of the CX3C chemokine family. Unlike other chemokines that are promiscuous, FKN binds only one receptor, the seven transmembrane $G_i$ protein-coupled receptor (GPCR) CX3CR1. In the CNS FKN is only expressed on neurons, and its receptor CX3CR1 is exclusively expressed on microglia. This complementary expression pattern led to the hypothesis that FKN mediates neuronal/microglial communication. Studies in CX3CR1-/- mice have confirmed that microglial maintenance of neuronal function requires this signalling system. CX3CR1-/- mice exhibit reduced or slowed synaptic maturation, impaired neuronal survival, deficits in synaptic transmission and plasticity and suboptimal hippocampal-dependent learning and memory.

CX3CR1 activation appears to limit inflammation and promote homeostatic activities such as synaptic maintenance. After injury, FKN can be released from the neuronal cell surface, attracting microglia to the site of injury to participate in tissue repair. In AD mouse models, FKN signalling plays a unique role in regulating disease progression. CX3CR1-/- and CX3CL1-/- mice have been bred to various AD models, and profound differences in the pathology and behaviour of the animals was observed. CX3CR1-/- in APP/PS-1 mice increased cytokine levels and Tau hyperphosphorylation and impaired behavioural performance. In two other models CX3CR1 ablation promoted A clearance and induced microglial activation and prevented neuronal loss. Like other key neuroinflammation genes, mouse studies have demonstrated either exacerbation or amelioration of AD pathology and memory by genetic alteration of this system, in a context-dependent manner, including whether the model was amyloid or tau-based or was examined at a young or older age. These data clearly demonstrate that the FKN signalling system can powerfully modulate AD pathogenesis. Thus, targeting CX3CR1 is worthwhile of further exploration and may provide novel opportunities for treatment of AD.

Unfortunately, despite widespread interest for many years across the pharmaceutical industry, there are no CNS-compatible inhibitors of CX3CR1. Furthermore there are no small molecule agonists or positive allosteric modulators of any kind.

Consequently, there is still an unmet need for compounds which are able to efficiently stimulate CX3CR1 and that can be delivered to the different target organs which are sites of any CX3CR1-mediated pathology. Such compounds are provided herein.

Various embodiments of the compounds provided herein are presented hereafter.

DETAILED DESCRIPTION

Figure 1:
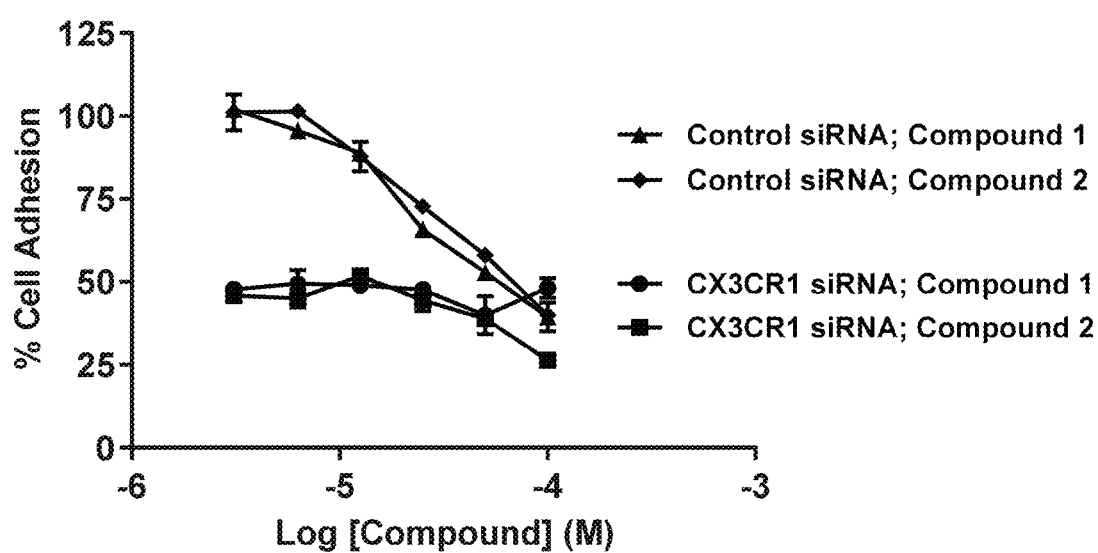
FIG. 1 shows the effect of various concentrations of compounds disclosed herein on THP-1 cell adhesion to HepG2 cells.

Disclosed herein are bicyclic compounds of the following formula (I), constituting Embodiment 1:

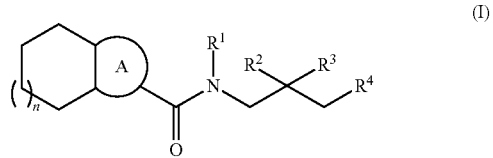

(I)

or a stereoisomer thereof, or a salt of any of the foregoing, wherein:

n is an integer between 1 and 4, forming a 6-10-membered cycloalkyl;

A is chosen from phenyl and heteroaryl, optionally substituted with one or more $C_1$-$C_3$ alkyl substituents;

$R^1$ is chosen from hydrogen and $C_1$-$C_3$ alkyl;

$R^2$ and $R^3$ are independently chosen from hydrogen, phenyl, and $C_1$-$C_6$ alkyl; or $R^2$ and $R^3$ are joined together via a group Y, such that $R^2$—Y—$R^3$, together with the carbon to which $R^2$ and $R^3$ attach, forms $C_3$-$C_7$ cycloalkyl or $C_3$-$C_7$ heterocycloalkyl, either of which is optionally substituted with one or more substituents chosen from hydroxyl, halogen, and $C_1$-$C_6$ alkyl; or the $C_3$-$C_7$ cycloalkyl or $C_3$-$C_7$ heterocycloalkyl is fused with a phenyl ring, which is optionally substituted with one or more substituents chosen from hydroxyl, halogen, and $C_1$-$C_6$ alkyl;

Y is chosen from C and O;

$R^4$ is chosen from

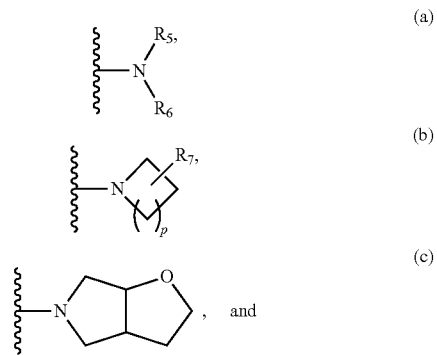

(a)

(b)

(c)

, and

-continued

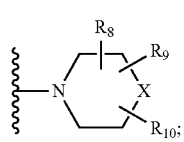
(d)

$R^5$ and $R^6$ are each independently $C_1$-$C_6$ alkyl;

$R^7$, $R^8$, $R^9$, and $R^{10}$ are independently chosen from hydrogen and hydroxyl, or is independently chosen from $C_1$-$C_6$ alkyl and $C_1$-$C_6$ alkyloxy, either of which is optionally substituted with methoxy;

p is 1 or 2;

X is chosen from C, O, and $NR^{11}$; and $R^{11}$ is hydrogen or $C_1$-$C_3$ alkyl.

In certain embodiments, if A is thiophene, n is 3, $R^1$ is hydrogen, and $R^4$ is

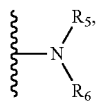

then either $R^5$ and $R^6$ are not both methyl, or $R^2$ and $R^3$ are not both methyl.

In certain embodiments, A is thiophene.

In certain embodiments, $R^1$ is chosen from hydrogen and methyl.

In certain embodiments, $R^2$ and $R^3$ are independently chosen from hydrogen, methyl, ethyl, and phenyl; or $R^2$ and $R^3$ are joined together via a group Y, such that $R^2$—Y—$R^3$, together with the carbon to which $R^2$ and $R^3$ attach, forms $C_3$-$C_6$ cycloalkyl or heterocycloalkyl, either of which is optionally substituted with one or more substituents chosen from hydroxyl, fluorine, and methyl; or the $C_3$-$C_7$ cycloalkyl or $C_3$-$C_7$ heterocycloalkyl is fused with a phenyl ring which is optionally substituted with one or more substituents chosen from hydroxyl, halogen, and $C_1$-$C_6$ alkyl.

In certain embodiments, $R^2$ and $R^3$ are independently chosen from hydrogen, methyl, ethyl, and phenyl.

In certain embodiments, $R^2$ and $R^3$ are joined together via a group Y, such that $R^2$—Y—$R^3$, together with the carbon to which $R^2$ and $R^3$ attach, forms $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

In certain embodiments, $R^5$ and $R^6$ are each independently $C_1$-$C_3$ alkyl.

In certain embodiments, $R^7$, $R^8$, $R^9$, and $R^{10}$ are independently chosen from hydrogen and hydroxyl, or is independently chosen from $C_1$-$C_3$ alkyl and $C_1$-$C_3$ alkoxy, either of which is optionally substituted with methoxy.

In certain embodiments, X is chosen from C, O, or NH.

In certain embodiments, provided herein is a compound of Formula I wherein:

n is a number between 1 and 4, forming a 6-10-membered cycloalkyl;

A is thiophene;

$R^1$ is chosen from hydrogen and methyl;

$R^2$ and $R^3$ are independently chosen from hydrogen, methyl, ethyl, and phenyl; or $R^2$ and $R^3$ are joined together via a group Y, such that $R^2$—Y—$R^3$, together with the carbon to which $R^2$ and $R^3$ attach, forms $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

Y is chosen from C and O;

$R^4$ is chosen from

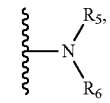
(a)

(b)

(c)

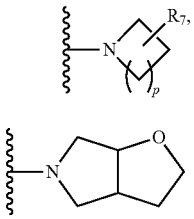
, and

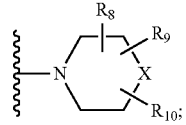
(d)

$R^5$ and $R^6$ are independently $C_1$-$C_3$ alkyl;

$R^7$, $R^8$, $R^9$, and $R^{10}$ are independently chosen from hydrogen and hydroxyl, or is independently chosen from $C_1$-$C_3$ alkyl and $C_1$-$C_3$ alkoxy, either of which is optionally substituted with methoxy;

p is 1 or 2;

X is chosen from C, O, and $NR^{11}$; and $R^{11}$ is hydrogen or $C_1$-$C_3$ alkyl.

In certain embodiments, A is 3-methylthiophene.

In certain embodiments, $R^1$ is chosen from hydrogen and methyl.

In certain embodiments, $R^2$ and $R^3$ are independently chosen from hydrogen, methyl, ethyl, and phenyl; or $R^2$ and $R^3$ are joined together via a group Y, such that $R^2$—Y—$R^3$, together with the carbon to which $R^2$ and $R^3$ attach, forms a $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

In certain embodiments, $R^2$ and $R^3$ are independently chosen from hydrogen, methyl, ethyl, and phenyl.

In certain embodiments, $R^2$ and $R^3$ are joined together via a group Y, such that $R^2$—Y—$R^3$, together with the carbon to which $R^2$ and $R^3$ attach, forms $C_3$-$C_6$ cycloalkyl or heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

In certain embodiments, either:

R² is hydrogen and R³ is methyl or phenyl; or

R² and R³ are both methyl or both ethyl.

In certain embodiments, R² is hydrogen and R³ is methyl or phenyl.

In certain embodiments, R² and R³ are both methyl or ethyl.

In certain embodiments,

Y is chosen from C and O; and

R² and R³ are joined together via the group Y, such that the group R²—Y—R³, together with the carbon to which R² and R³ attach, forms a cyclopropyl, cyclobutyl, cyclopentyl, cyclohexyl, furan-3-yl, pyran-3-yl, and pyran-4-yl, any of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

In certain embodiments, R⁵ and R⁶ are each independently $C_1$-$C_3$ alkyl.

In certain embodiments, R⁷, R⁸, R⁹, and R¹⁰ are independently chosen from hydrogen and hydroxyl, or is independently chosen from $C_1$-$C_3$ alkyl and $C_1$-$C_3$ alkoxy, either of which is optionally substituted with methoxy.

In certain embodiments, X is chosen from C, O, or NH.

In certain embodiments,

X is chosen from C, O, and NR¹¹; and

R₁₁ is $C_1$-$C_3$ alkyl.

In certain embodiments, provided herein is a compound of Formula I wherein:

n is a number between 1 and 4, forming a 6-10-membered cycloalkyl;

A is 3-methylthiophene;

R¹ is chosen from hydrogen and methyl;

R² and R³ are independently hydrogen, methyl, ethyl, and phenyl; or R² and R³ are joined together via a group Y, such that R²—Y—R³, together with the carbon to which R² and R³ attach, forms $C_3$-$C_6$ cycloalkyl or $C_3$-$C_6$ heterocycloalkyl chosen from cyclopropyl, cyclobutyl, cyclopentyl, cyclohexyl, furan-3-yl, pyran-3-yl, and pyran-4-yl, any of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl;

Y is chosen from C and O;

R⁴ is chosen from

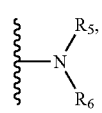

(a)

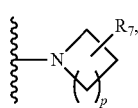

(b)

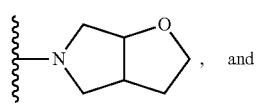

, and (c)

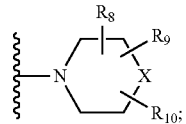

(d)

R⁵ and R⁶ are independently $C_1$-$C_3$ alkyl;

R⁷, R⁸, R⁹, and R¹⁰ are independently chosen from hydrogen and hydroxyl, or is independently chosen from methyl and $C_1$-$C_3$ alkyloxy, either of which is optionally substituted with methoxy;

p is 1 or 2; and

X is chosen from C, O, and NR¹¹; and

R₁₁ is $C_1$-$C_3$ alkyl.

In certain embodiments, provided herein is a compound of Formula I wherein:

n is an integer between 1 and 4, forming a 6-10-membered cycloalkyl;

A is chosen from phenyl and heteroaryl, optionally substituted with one or more $C_1$-$C_3$ alkyl substituents;

R¹ is chosen from hydrogen and $C_1$-$C_3$ alkyl;

R² and R³ are joined together via a group Y, such that R²—Y—R³, together with the carbon to which R² and R³ attach, forms $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl;

Y is chosen from C and O;

R⁴ is chosen from

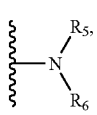

(a)

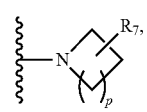

(b)

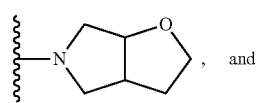

, and (c)

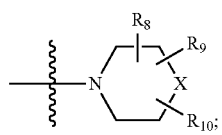

(d)

R⁵ and R⁶ are each independently $C_1$-$C_6$ alkyl;

R⁷, R⁸, R⁹, and R¹⁰ are independently chosen from hydrogen and hydroxyl, or is independently chosen from $C_1$-$C_6$ alkyl and $C_1$-$C_6$ alkyloxy, either of which is optionally substituted with methoxy;

p is 1 or 2; and

X is chosen from C, O, or NR¹¹ where R¹¹ is hydrogen or $C_1$-$C_3$ alkyl;

with the proviso that if A is thiophene, n is 2 or 3, $R^1$ is hydrogen, and $R^4$ is

then $R^5$ and $R^6$ are not both methyl.

Also provided are the following specific embodiments.

Embodiment 1.1: The compound of Embodiment 1, wherein if A is thiophene, n is 3, $R^1$ is hydrogen, and $R^4$ is

then either $R^5$ and $R^6$ are not both methyl, or $R^2$ and $R^3$ are not both methyl.

Embodiment 2: The compound of anyone of Embodiments 1-1.1, wherein A is thiophene.

Embodiment 3: The compound of any one of Embodiments 1-2, wherein $R^1$ is chosen from hydrogen and methyl.

Embodiment 4: The compound of any one of Embodiments 1-3, wherein $R^2$ and $R^3$ are independently chosen from hydrogen, methyl, ethyl, and phenyl; or $R^2$ and $R^3$ are joined together via a group Y, such that $R^2$—Y—$R^3$, together with the carbon to which $R^2$ and $R^3$ attach, forms $C_3$-$C_6$ cycloalkyl or heterocycloalkyl, either of which is optionally substituted with one or more substituents chosen from hydroxyl, fluorine, and methyl; or the $C_3$-$C_7$ cycloalkyl or $C_3$-$C_7$ heterocycloalkyl is fused with a phenyl ring which is optionally substituted with one or more substituents chosen from hydroxyl, halogen, and $C_1$-$C_6$ alkyl.

Embodiment 5: The compound of Embodiment 4, wherein $R^2$ and $R^3$ are independently chosen from hydrogen, methyl, ethyl, and phenyl.

Embodiment 6: The compound of Embodiment 4, wherein $R^2$ and $R^3$ are joined together via a group Y, such that $R^2$—Y—$R^3$, together with the carbon to which $R^2$ and $R^3$ attach, forms $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

Embodiment 7: The compound of Embodiment 6, wherein $R^5$ and $R^6$ are each independently $C_1$-$C_3$ alkyl.

Embodiment 8: The compound of Embodiment 6, wherein $R^7$, $R^8$, $R^9$, and $R^{10}$ are independently chosen from hydrogen and hydroxyl, or is independently chosen from $C_1$-$C_3$ alkyl and $C_1$-$C_3$ alkoxy, either of which is optionally substituted with methoxy.

Embodiment 9: The compound of Embodiment 6, wherein X is chosen from C, O, or NH.

Embodiment 10: The compound of any one of Embodiments 1-9, wherein:

n is a number between 1 and 4, forming a 6-10-membered cycloalkyl;

A is thiophene;

$R^1$ is chosen from hydrogen and methyl;

$R^2$ and $R^3$ are independently chosen from hydrogen, methyl, ethyl, and phenyl; or $R^2$ and $R^3$ are joined together via a group Y, such that $R^2$—Y—$R^3$, together with the carbon to which $R^2$ and $R^3$ attach, forms $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

Y is chosen from C and O;

$R^4$ is chosen from

 (a)

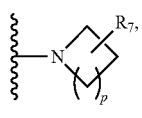 (b)

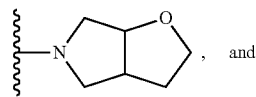 (c)

, and

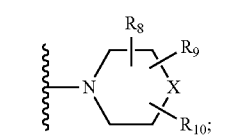 (d)

$R^5$ and $R^6$ are independently $C_1$-$C_3$ alkyl;

$R^7$, $R^8$, $R^9$, and $R^{10}$ are independently chosen from hydrogen and hydroxyl, or is independently chosen from $C_1$-$C_3$ alkyl and $C_1$-$C_3$ alkoxy, either of which is optionally substituted with methoxy;

p is 1 or 2;

X is chosen from C, O, and $NR^{11}$; and $R^{11}$ is hydrogen or $C_1$-$C_3$ alkyl.

Embodiment 11: The compound of anyone of Embodiments 1-10, wherein A is 3-methylthiophene.

Embodiment 12: The compound of anyone of Embodiments 1-11, wherein $R^1$ is chosen from hydrogen and methyl.

Embodiment 13: The compound of any one of Embodiments 1-12, wherein $R^2$ and $R^3$ are independently chosen from hydrogen, methyl, ethyl, and phenyl; or $R^2$ and $R^3$ are joined together via a group Y, such that $R^2$—Y—$R^3$, together with the carbon to which $R^2$ and $R^3$ attach, forms a $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

Embodiment 14: The compound of Embodiment 13, wherein $R^2$ and $R^3$ are independently chosen from hydrogen, methyl, ethyl, and phenyl.

Embodiment 15: The compound of Embodiment 13, wherein $R^2$ and $R^3$ are joined together via a group Y, such that $R^2$—Y—$R^3$, together with the carbon to which $R^2$ and $R^3$ attach, forms $C_3$-$C_6$ cycloalkyl or heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

Embodiment 16: The compound of Embodiment 14, wherein either:
$R^2$ is hydrogen and $R^3$ is methyl or phenyl; or
$R^2$ and $R^3$ are both methyl or both ethyl.

Embodiment 17: The compound of Embodiment 14, wherein $R^2$ is hydrogen and $R^3$ is methyl or phenyl.

Embodiment 18: The compound of Embodiment 14, wherein $R^2$ and $R^3$ are both methyl or ethyl.

Embodiment 19: The compound of Embodiment 15, wherein
Y is chosen from C and O; and
$R^2$ and $R^3$ are joined together via the group Y, such that the group $R^2$—Y—$R^3$, together with the carbon to which $R^2$ and $R^3$ attach, forms a cyclopropyl, cyclobutyl, cyclopentyl, cyclohexyl, furan-3-yl, pyran-3-yl, and pyran-4-yl, any of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl.

Embodiment 20: The compound of Embodiment 19, wherein $R^5$ and $R^6$ are each independently $C_1$-$C_3$ alkyl.

Embodiment 21: The compound of Embodiment 19, wherein $R^7$, $R^8$, $R^9$, and $R^{10}$ are independently chosen from hydrogen and hydroxyl, or is independently chosen from $C_1$-$C_3$ alkyl and $C_1$-$C_3$ alkoxy, either of which is optionally substituted with methoxy.

Embodiment 22: The compound of Embodiment 19, wherein X is chosen from C, O, or NH.

Embodiment 23: The compound of Embodiment 19, wherein
X is chosen from C, O, and $NR^{11}$; and
$R_{11}$ is $C_1$-$C_3$ alkyl.

Embodiment 24: The compound of any one of Embodiments 1-23, wherein:
n is a number between 1 and 4, forming a 6-10-membered cycloalkyl;
A is 3-methylthiophene;
$R^1$ is chosen from hydrogen and methyl;
$R^2$ and $R^3$ are independently hydrogen, methyl, ethyl, and phenyl; or $R^2$ and $R^3$ are joined together via a group Y, such that $R^2$—Y—$R^3$, together with the carbon to which $R^2$ and $R^3$ attach, forms $C_3$-$C_6$ cycloalkyl or $C_3$-$C_6$ heterocycloalkyl chosen from cyclopropyl, cyclobutyl, cyclopentyl, cyclohexyl, furan-3-yl, pyran-3-yl, and pyran-4-yl, any of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl;
Y is chosen from C and O;
$R^4$ is chosen from

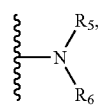

(a)

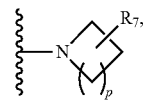

(b)

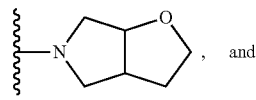

, and (c)

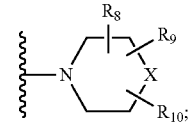

(d)

$R^5$ and $R^6$ are independently $C_1$-$C_3$ alkyl;
$R^7$, $R^8$, $R^9$, and $R^{10}$ are independently chosen from hydrogen and hydroxyl, or is independently chosen from methyl and $C_1$-$C_3$ alkyloxy, either of which is optionally substituted with methoxy;
p is 1 or 2; and
X is chosen from C, O, and $NR^{11}$; and
$R_{11}$ is $C_1$-$C_3$ alkyl.

In certain embodiments, a compound of formula (I) disclosed herein is chosen from the compounds set forth in Table 1. In certain embodiments, Ex. 70 is excluded.

TABLE 1

| Ex. | Chemical Name |
|---|---|
| 1 | N-(2,2-dimethyl-3-pyrrolidin-1-ylpropyl)-4,5,6,7,8,9-hexahydrocycloocta[b]thiophene-2-carboxamide |
| 2 | N-[[1-[(dimethylamino)methyl]cyclopentyl]methyl]-4,5,6,7,8,9-hexahydrocycloocta[b]thiophene-2-carboxamide |
| 3 | N-[3-(dimethylamino)-2-methylpropyl]-4,5,6,7,8,9-hexahydrocycloocta[b]thiophene-2-carboxamide |
| 4 | N-[[1-(pyrrolidin-1-ylmethyl)cyclopropyl]methyl]-4,5,6,7,8,9-hexahydrocycloocta[b]thiophene-2-carboxamide |
| 5 | N-[[1-(pyrrolidin-1-ylmethyl)cyclopentyl]methyl]-4,5,6,7,8,9-hexahydrocycloocta[b]thiophene-2-carboxamide |
| 6 | N-[[1-[[methyl(propyl)amino]methyl]cyclopentyl]methyl]-4,5,6,7,8,9-hexahydrocycloocta[b]thiophene-2-carboxamide |
| 7 | N-[3-(dimethylamino)-2,2-dimethylpropyl]-N-methyl-4,5,6,7,8,9-hexahydrocycloocta[b]thiophene-2-carboxamide |
| 8 | N-[2-[(dimethylamino)methyl]-2-ethylbutyl]-4,5,6,7,8,9-hexahydrocycloocta[b]thiophene-2-carboxamide |
| 9 | N-[2-ethyl-2-(pyrrolidin-1-ylmethyl)butyl]-4,5,6,7,8,9-hexahydrocycloocta[b]thiophene-2-carboxamide |
| 10 | N-[[2-[(dimethylamino)methyl]-1,3-dihydroinden-2-yl]methyl]-4,5,6,7,8,9-hexahydrocycloocta[b]thiophene-2-carboxamide |
| 11 | N-[[2-(pyrrolidin-1-ylmethyl)-1,3-dihydroinden-2-yl]methyl]-4,5,6,7,8,9-hexahydrocycloocta[b]thiophene-2-carboxamide |
| 12 | N-[[1-(diethylaminomethyl)cyclopentyl]methyl]-4,5,6,7,8,9-hexahydrocycloocta[b]thiophene-2-carboxamide |
| 13 | N-(2,2-dimethyl-3-piperidin-1-ylpropyl)-4,5,6,7,8,9-hexahydrocycloocta[b]thiophene-2-carboxamide |
| 14 | N-[[1-(azetidin-1-ylmethyl)cyclopentyl]methyl]-4,5,6,7,8,9-hexahydrocycloocta[b]thiophene-2-carboxamide |
| 15 | N-[[1-(piperidin-1-ylmethyl)cyclopentyl]methyl]-4,5,6,7,8,9-hexahydrocycloocta[b]thiophene-2-carboxamide |
| 16 | N-[3-(diethylamino)-2,2-dimethylpropyl]-4,5,6,7,8,9-hexahydrocycloocta[b]thiophene-2-carboxamide |
| 17 | N-[[1-[[2-hydroxyethyl(methyl)amino]methyl]cyclopentyl]methyl]-4,5,6,7,8,9-hexahydrocycloocta[b]thiophene-2-carboxamide |
| 18 | N-[[1-(pyrrolidin-1-ylmethyl)cyclohexyl]methyl]-4,5,6,7,8,9-hexahydrocycloocta[b]thiophene-2-carboxamide |
| 19 | N-[[4-[(dimethylamino)methyl]oxan-4-yl]methyl]-4,5,6,7,8,9-hexahydrocycloocta[b]thiophene-2-carboxamide |
| 20 | N-[[4-(pyrrolidin-1-ylmethyl)oxan-4-yl]methyl]-4,5,6,7,8,9-hexahydrocycloocta[b]thiophene-2-carboxamide |

TABLE 1-continued

| Ex. | Chemical Name |
|---|---|
| 21 | N-[[1-(pyrrolidin-1-ylmethyl)cyclobutyl]methyl]-4,5,6,7,8,9-hexahydrocycloocta[b]thiophene-2-carboxamide |
| 22 | N-[[1-[(dimethylamino)methyl]cyclohexyl]methyl]-4,5,6,7,8,9-hexahydrocycloocta[b]thiophene-2-carboxamide |
| 23 | N-[[1-[(dimethylamino)methyl]cyclobutyl]methyl]-4,5,6,7,8,9-hexahydrocycloocta[b]thiophene-2-carboxamide |
| 24 | N-(2,2-dimethyl-3-pyrrolidin-1-ylpropyl)-5,6,7,8,9,10-hexahydro-4H-cyclonona[b]thiophene-2-carboxamide |
| 25 | N-[[1-[(3-hydroxypyrrolidin-1-yl)methyl]cyclopentyl]methyl]-4,5,6,7,8,9-hexahydrocycloocta[b]thiophene-2-carboxamide |
| 26 | N-[[1-(pyrrolidin-1-ylmethyl)cyclobutyl]methyl]-5,6,7,8,9,10-hexahydro-4H-cyclonona[b]thiophene-2-carboxamide |
| 27 | N-[[1-[(3-hydroxypiperidin-1-yl)methyl]cyclopentyl]methyl]-4,5,6,7,8,9-hexahydrocycloocta[b]thiophene-2-carboxamide |
| 28 | N-[[1-[(4-hydroxypiperidin-1-yl)methyl]cyclopentyl]methyl]-4,5,6,7,8,9-hexahydrocycloocta[b]thiophene-2-carboxamide |
| 29 | N-[[1-[[2-hydroxyethyl(methyl)amino]methyl]cyclopentyl]methyl]-5,6,7,8,9,10-hexahydro-4H-cyclonona[b]thiophene-2-carboxamide |
| 30 | N-[[1-[[2-hydroxyethyl(methyl)amino]methyl]cyclobutyl]methyl]-4,5,6,7,8,9-hexahydrocycloocta[b]thiophene-2-carboxamide |
| 31 | N-[[1-[(dimethylamino)methyl]-3-hydroxycyclobutyl]methyl]-4,5,6,7,8,9-hexahydrocycloocta[b]thiophene-2-carboxamide |
| 32 | N-[[3-hydroxy-1-(pyrrolidin-1-ylmethyl)cyclobutyl]methyl]-4,5,6,7,8,9-hexahydrocycloocta[b]thiophene-2-carboxamide |
| 33 | N-[[1-[(dimethylamino)methyl]cyclopentyl]methyl]-5,6,7,8,9,10-hexahydrobenzo[8]annulene-3-carboxamide |
| 34 | N-[[1-[[2-hydroxyethyl(methyl)amino]methyl]cyclopentyl]methyl]-5,6,7,8-tetrahydro-4H-cyclohepta[b]thiophene-2-carboxamide |
| 35 | N-[[4-(azetidin-1-ylmethyl)oxan-4-yl]methyl]-4,5,6,7,8,9-hexahydrocycloocta[b]thiophene-2-carboxamide |
| 36 | N-[[1-(azetidin-1-ylmethyl)cyclobutyl]methyl]-4,5,6,7,8,9-hexahydrocycloocta[b]thiophene-2-carboxamide |
| 37 | N-[[3-[(dimethylamino)methyl]oxan-3-yl]methyl]-4,5,6,7,8,9-hexahydrocycloocta[b]thiophene-2-carboxamide |
| 38 | N-[[3-[(dimethylamino)methyl]oxolan-3-yl]methyl]-4,5,6,7,8,9-hexahydrocycloocta[b]thiophene-2-carboxamide |
| 39 | N-[[3-(pyrrolidin-1-ylmethyl)oxolan-3-yl]methyl]-4,5,6,7,8,9-hexahydrocycloocta[b]thiophene-2-carboxamide |
| 40 | N-[[4-[(4-hydroxypiperidin-1-yl)methyl]oxan-4-yl]methyl]-4,5,6,7,8,9-hexahydrocycloocta[b]thiophene-2-carboxamide |
| 41 | N-[[1-[(4-hydroxypiperidin-1-yl)methyl]cyclobutyl]methyl]-4,5,6,7,8,9-hexahydrocycloocta[b]thiophene-2-carboxamide |
| 42 | N-[3-[4-(2-methoxyethoxy)piperidin-1-yl]-2,2-dimethylpropyl]-4,5,6,7,8,9-hexahydrocycloocta[b]thiophene-2-carboxamide |
| 43 | N-[[3-[(3-hydroxypyrrolidin-1-yl)methyl]oxan-3-yl]methyl]-4,5,6,7,8,9-hexahydrocycloocta[b]thiophene-2-carboxamide |
| 44 | N-[[3-(pyrrolidin-1-ylmethyl)oxan-3-yl]methyl]-4,5,6,7,8,9-hexahydrocycloocta[b]thiophene-2-carboxamide |
| 45 | N-[[3-[(4-hydroxypiperidin-1-yl)methyl]oxan-3-yl]methyl]-4,5,6,7,8,9-hexahydrocycloocta[b]thiophene-2-carboxamide |
| 46 | N-[3-(3-hydroxypiperidin-1-yl)-2,2-dimethylpropyl]-4,5,6,7,8,9-hexahydrocycloocta[b]thiophene-2-carboxamide |
| 47 | N-[3-(4-methoxypiperidin-1-yl)-2,2-dimethylpropyl]-4,5,6,7,8,9-hexahydrocycloocta[b]thiophene-2-carboxamide |
| 48 | N-[[1-[(4-methoxy-4-methylpiperidin-1-yl)methyl]cyclobutyl]methyl]-4,5,6,7,8,9-hexahydrocycloocta[b]thiophene-2-carboxamide |
| 49 | N-[[1-[(4-methoxypiperidin-1-yl)methyl]cyclobutyl]methyl]-4,5,6,7,8,9-hexahydrocycloocta[b]thiophene-2-carboxamide |
| 50 | N-[[1-[(3-propan-2-yloxypiperidin-1-yl)methyl]cyclobutyl]methyl]-4,5,6,7,8,9-hexahydrocycloocta[b]thiophene-2-carboxamide |
| 51 | N-[[1-[(4-propan-2-yloxypiperidin-1-yl)methyl]cyclobutyl]methyl]-4,5,6,7,8,9-hexahydrocycloocta[b]thiophene-2-carboxamide |
| 52 | N-[[1-[(3-hydroxy-3-methylpiperidin-1-yl)methyl]cyclopentyl]methyl]-4,5,6,7,8,9-hexahydrocycloocta[b]thiophene-2-carboxamide |
| 53 | N-[[1-[(4-methoxy-4-methylpiperidin-1-yl)methyl]cyclopentyl]methyl]-4,5,6,7,8,9-hexahydrocycloocta[b]thiophene-2-carboxamide |
| 54 | N-[3-(3-methoxypiperidin-1-yl)-2,2-dimethylpropyl]-4,5,6,7,8,9-hexahydrocycloocta[b]thiophene-2-carboxamide |
| 55 | N-[3-(3-methoxypiperidin-1-yl)-2,2-dimethylpropyl]-4,5,6,7,8,9-hexahydrocycloocta[b]thiophene-2-carboxamide |
| 56 | N-[[1-[(dimethylamino)methyl]-3,3-difluorocyclobutyl]methyl]-4,5,6,7,8,9-hexahydrocycloocta[b]thiophene-2-carboxamide |
| 57 | N-[[3,3-difluoro-1-(pyrrolidin-1-ylmethyl)cyclobutyl]methyl]-4,5,6,7,8,9-hexahydrocycloocta[b]thiophene-2-carboxamide |
| 58 | N-[[1-[(4-hydroxy-3,3-dimethylpiperidin-1-yl)methyl]cyclobutyl]methyl]-4,5,6,7,8,9-hexahydrocycloocta[b]thiophene-2-carboxamide |
| 59 | N-[[1-[(3-hydroxy-3-methylpiperidin-1-yl)methyl]cyclobutyl]methyl]-4,5,6,7,8,9-hexahydrocycloocta[b]thiophene-2-carboxamide |
| 60 | N-[[1-[(dimethylamino)methyl]-2-methylcyclopentyl]methyl]-4,5,6,7,8,9-hexahydrocycloocta[b]thiophene-2-carboxamide |
| 61 | N-[[1-[(dimethylamino)methyl]-2-methylcyclopentyl]methyl]-4,5,6,7,8,9-hexahydrocycloocta[b]thiophene-2-carboxamide |
| 62 | N-[[2-methyl-1-(pyrrolidin-1-ylmethyl)cyclopentyl]methyl]-4,5,6,7,8,9-hexahydrocycloocta[b]thiophene-2-carboxamide |
| 63 | N-[[1-[(3-hydroxypyrrolidin-1-yl)methyl]cyclopentyl]methyl]-4,5,6,7,8,9-hexahydrocycloocta[b]thiophene-2-carboxamide |
| 64 | N-[[1-[(3-hydroxypyrrolidin-1-yl)methyl]cyclopentyl]methyl]-4,5,6,7,8,9-hexahydrocycloocta[b]thiophene-2-carboxamide |
| 65 | N-[[1-[(3-hydroxypiperidin-1-yl)methyl]cyclobutyl]methyl]-4,5,6,7,8,9-hexahydrocycloocta[b]thiophene-2-carboxamide |
| 66 | N-[[1-[(3-hydroxypyrrolidin-1-yl)methyl]cyclobutyl]methyl]-4,5,6,7,8,9-hexahydrocycloocta[b]thiophene-2-carboxamide |
| 67 | N-[3-(4-hydroxy-4-methylpiperidin-1-yl)-2,2-dimethylpropyl]-4,5,6,7,8,9-hexahydrocycloocta[b]thiophene-2-carboxamide |
| 68 | N-[3-(4-hydroxy-3,3-dimethylpiperidin-1-yl)-2,2-dimethylpropyl]-4,5,6,7,8,9-hexahydrocycloocta[b]thiophene-2-carboxamide |
| 69 | N-[[1-[[(3aR,6aS)-2,3,3a,4,6,6a-hexahydrofuro[2,3-c]pyrrol-5-yl]methyl]cyclopentyl]methyl]-4,5,6,7,8,9-hexahydrocycloocta[b]thiophene-2-carboxamide |
| 70 | N-[3-(dimethylamino)-2,2-dimethylpropyl]-4,5,6,7,8,9-hexahydrocycloocta[b]thiophene-2-carboxamide |

Also provided herein is a compound as disclosed herein for use as a medicament.

Also provided herein is a compound as disclosed herein, or a stereoisomer thereof, or a salt of any of the foregoing, for use in the treatment of a CR3CX1-mediated disease.

Also provided herein is a compound as disclosed herein, or a stereoisomer thereof, or a salt of any of the foregoing, for use in the manufacture of a medicament for the prevention or treatment of a disease or condition ameliorated by the modulation of CX3CR1.

Also provided herein is a pharmaceutical composition comprising a compound as disclosed herein, or a stereoisomer thereof, or a salt of any of the foregoing, together with a pharmaceutically acceptable carrier.

Also provided herein is a method of treatment of a CX3CR1-mediated disease comprising the administration of a therapeutically effective amount of a compound as disclosed herein, or a stereoisomer thereof, or a salt of any of the foregoing, to a subject in need thereof.

In certain embodiments, the disease is chosen from cancer, an inflammatory disorder, pain, a neurodegenerative disorders, a cognitive disorder, and a psychiatric disorder.

In certain embodiments, the disease is Alzheimer's Disease.

Also provided herein is a method of modulation of CX3CR1 comprising contacting CX3CR1 with a compound as disclosed herein, or a stereoisomer thereof, or a salt of any of the foregoing.

Also provided herein is a method of making a compound disclosed herein, comprising the procedure(s) described below and variations thereupon.

Compounds of formula (I) can be prepared by reacting a compound of formula (II):

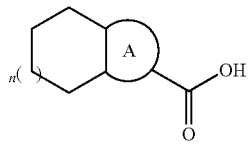

(II)

wherein n is between 1 and 4 and the meanings of A are as defined above, with a compound of formula (III)

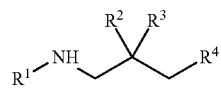

(III)

wherein the meanings of $R^1$, $R^2$, $R^3$ and $R^4$ are as defined above.

The reaction of a compound of formula (II) with a compound of formula (III) may be carried out in a reaction-inert solvent such as $CH_2Cl_2$, THF or toluene, and in the presence of a suitable coupling reagents such as CDI, HATU, PyBOP or $SOCl_2$ and of a suitable base such as TEA or DBU. The reaction may conveniently be carried out at a temperatures between room temperature and the reflux temperature of the reaction mixture and optionally converting the obtained compound of formula (I) into an addition salt thereof, and/or preparing stereochemically isomeric forms thereof.

Reagents of formula (III) are known in the art.

Reagents of formula (II) either are commercially available, or can be prepared according to the following schemes:

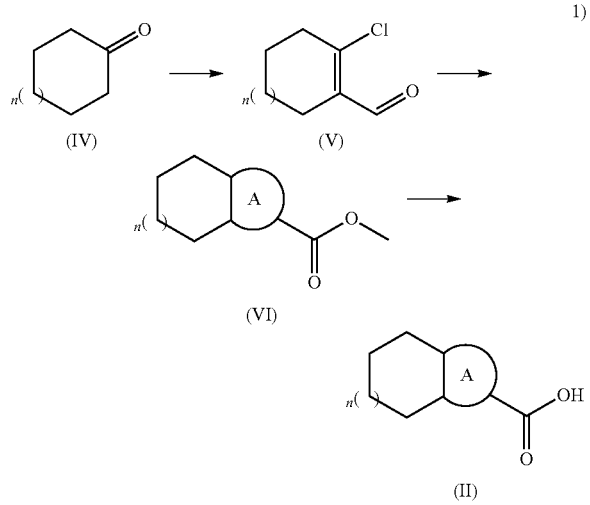

1)

wherein n is 4 and the meanings of A are as defined above;

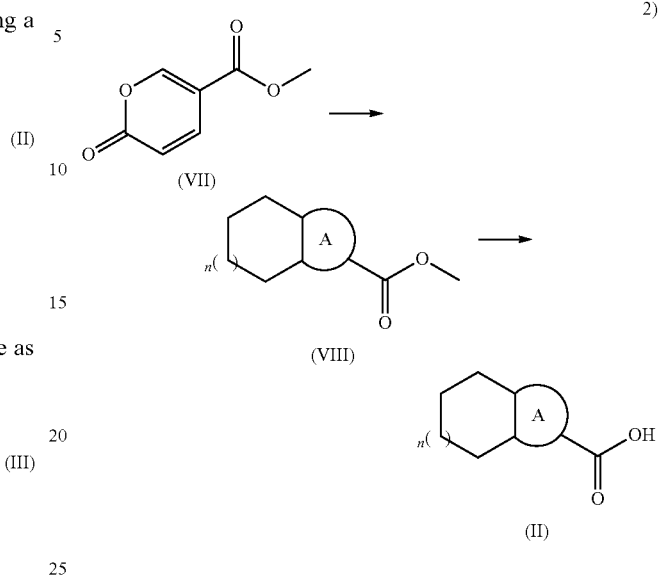

2)

wherein n is 3 and the meanings of A are as defined above.

Compounds of formula (I) can also be prepared by reacting a compound of formula (IX):

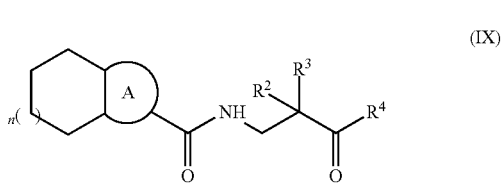

(IX)

wherein n is between 1 and 4, the meanings of A are as defined above and the meanings of $R^2$, $R^3$ and $R^4$ are as defined above, with an hydride such as $LiAlH_4$. The reaction may be carried out in a solvent such as THF at, e.g., room temperature.

Compounds of formula (IX) can also be prepared as reported in the specific examples below.

The compounds disclosed herein may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (1) involves liquid chromatography using a chiral stationary phase. Said pure stereochemically isomeric forms may also be derived from the corresponding pure stereochemically isomeric forms of the appropriate starting materials, provided that the reaction occurs stereospecifically. If a specific stereoisomer is desired, said compound may be synthesized by stereospecific methods of preparation. These methods will advantageously employ enantiomerically pure starting materials.

The compounds of formula (I), the pharmaceutically acceptable salts and stereoisomeric forms thereof possess CX3CR1 receptor agonism as demonstrated in the Pharmacological Examples. Other examples of art-known group transformation reactions to convert compounds of formula (I) into other compounds of formula (I) are hydrolysis of carboxylic esters to the corresponding carboxylic acid or alcohol; hydrolysis of amides to the corresponding carboxylic acids or amines; alcohols may be converted into esters and ethers; primary amines may be converted into secondary or tertiary amines; double bonds may be hydrogenated to the corresponding single bond. The starting materials and some of the intermediates are known compounds and are commercially available or may be prepared according to conventional reaction procedures generally known in the art. The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. If a specific stereoisomer is desired, said compound will be synthesized by stereospecific methods of preparation. These methods will advantageously employ enantiomerically pure starting materials. In the preparation of the compounds of formula I and the starting materials and/or intermediates described herein it may be useful to protect certain groups which are sensitive to the reaction conditions. The evaluation of the usefulness of the optional protection, as well as the selection of the suitable protecting agent, according to the reaction carried out in the preparation of the compounds provided herein and the functional group to be protected, are within the common knowledge of the skilled person. The removal of the optional protective groups is carried out according to conventional techniques.

The preparation of the salts of the compounds of formula I is carried out according to known methods.

The present compounds of formula (I) (as well as stereoisomer(s) thereof and/or salt(s) thereof) are useful in the treatment of a condition or disease mediated by the CX3CR1 receptor, in particular CX3CR1 receptor agonistic activity. Furthermore, the present compounds (as well as stereoisomer(s) thereof and/or salt(s) thereof) may be used for the manufacture of a medicine for treatment of a condition or a disease mediated by CX3CR1 receptor activity, in particular CX3CR1 receptor agonistic activity.

The present disclosure also provides the use of a compound of formula (I) (as well as stereoisomer(s) thereof and/or salt(s) thereof) for the manufacture of a medicament for the treatment of conditions or diseases such as CX3CR1 receptor mediated conditions or diseases.

Definitions

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 mL (milliliters)," which is intended to include 1 mL, 3 mL, and everything in between to any number of significant figures (e.g., 1.255 mL, 2.1 mL, 2.9999 mL, etc.).

As used herein, the term "about" is intended to qualify the numerical values which it modifies, denoting such a value as variable within a range. When no range, such as a margin of error or a standard deviation to a mean value given in a chart or table of data, is recited, the term "about" should be understood to mean the greater of the range which would encompass the recited value and the range which would be included by rounding up or down to that figure as well, considering significant figures, and the range which would encompass the recited value plus or minus 20%.

As used herein, the term "agonist" refers to a moiety that interacts with, and activates, a receptor and thereby initiates a physiological or pharmacological response characteristic of that receptor. Unless specified otherwise, an agonist may be full or partial or a superagonist, selective or nonselective, reversible or irreversible. An agonist may bind at the active site of the target protein or it may bind to another site which alters the binding of the target site with a ligand (i.e., an allosteric site).

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The terms "halo," "halogen," and "halide," as used herein, alone or in combination, are interchangeable, and refer to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "perhaloalkoxy" refers to an alkoxy group where all of the hydrogen atoms are replaced by halogen atoms. One example of perhaloalkyl is perhalomethyl, also called trifluormethyl.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "perhaloalkyl" as used herein, alone or in combination, refers to an alkyl group where all of the hydrogen atoms are replaced by halogen atoms.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. Stereogenic centers may have the R- or S-configuration; substituents on bivalent cyclic (partially) saturated radicals may have either the cis- or trans-configuration. Stereochemically isomeric forms of the compounds of formula (I) are intended to be embraced within the scope of this disclosure. The absolute stereochemical configuration of the compounds of formula (I) and of the intermediates used in their preparation may easily be determined by those skilled in the art while using well-known methods such as, for example, X-ray diffraction.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, "treating," "treatment," and the like means ameliorating a disease, so as to reduce, ameliorate, or eliminate its cause, its progression, its severity, or one or more of its symptoms, or otherwise beneficially alter the disease in a subject. In certain embodiments, reference to "treating" or "treatment" of a subject at risk for developing a disease, or at risk of disease progression to a worse state, is intended to include prophylaxis. Prevention of a disease may involve complete protection from disease, for example as in the case of prevention of infection with a pathogen, or may involve prevention of disease progression, for example from prediabetes to diabetes. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

Furthermore, some compounds of formula (I) and some of the intermediates used in their preparation may exhibit polymorphism. It is to be understood that the present disclosure encompasses any polymorphic forms possessing properties useful in the treatment of the conditions noted hereinabove.

The pharmaceutically acceptable salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, trifluoromethanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form. The compounds of formula (I) may exist in both unsolvated and solvated forms. The term 'solvate' is used herein to describe a molecular association comprising a compound disclosed herein and one or more pharmaceutically acceptable solvent molecules, e.g. water or ethanol. The term 'hydrate' is used when said solvent is water.

Pharmaceutical Compositions

Additionally, pharmaceutical compositions/formulations comprising at least one pharmaceutically acceptable carrier and a therapeutically effective amount of a compound of formula (I) (as well as stereoisomer(s) thereof and/or salt(s) thereof) are provided herein. In order to prepare the pharmaceutical compositions of the compounds (as well as stereoisomer(s) thereof and/or salt(s) thereof) provided herein, a compound, optionally in base or acid addition salt form (or stereoisomer thereof), as the active ingredient (and typically, if administered alone, in a therapeutically effective amount), is combined with at least one pharmaceutically acceptable carrier, which carrier may take a variety of forms depending on the form of preparation desired for administration. These pharmaceutical compositions may be in unitary dosage form suitable for oral administration, rectal administration, percutaneous administration or parenteral injection.

Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a salt or stereoisomer thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Compounds (as well as stereoisomer(s) thereof and/or salt(s) thereof, described herein can be administered as follows:

Oral Administration

The compounds (as well as stereoisomer(s) thereof and/or salt(s) thereof) may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds (as well as stereoisomer(s) thereof and/or salt(s) thereof) may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds (as well as stereoisomer(s) thereof and/or salt(s) thereof) may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Rectal, Buccal, and Sublingual Administration

Suppositories for rectal administration of the compounds (as well as stereoisomer(s) thereof and/or salt(s) thereof) can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Administration by Inhalation

For administration by inhalation, compounds may be conveniently delivered from an insufflator, nebulizer pressurized packs or other convenient means of delivering an aerosol spray or powder. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions described herein may be prepared by any of the well-known techniques of pharmacy, such as effective formulation and administration procedures. Preferred unit dosage formulations are those containing an effective dose, as herein recited, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity.

Additionally pharmaceutical compositions/formulations comprising at least one pharmaceutically acceptable carrier and a therapeutically effective amount of a compound of formula (I) are provided herein.

In order to prepare the pharmaceutical compositions of the compounds provided herein, an effective amount of the particular compound, optionally in base or acid addition salt form, as the active ingredient, is combined with at least one pharmaceutically acceptable carrier, which carrier may take a variety of forms depending on the form of preparation desired for administration. These pharmaceutical compositions may be in unitary dosage form suitable for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient.

Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (1), due to their increased water solubility over the corresponding base form, are obviously more suitable in the preparation of aqueous compositions.

It is especially advantageous to formulate the pharmaceutical compositions of the compounds disclosed herein in dosage unit form for ease of administration and uniformity of dosage.

"Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the compounds disclosed herein may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium lauryl sulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the disclosure comprise at least one intense sweetener such as aspartame, acesulfame potassium, sodium cyclamate, alitame, dihydrochalcone sweetener, monellin, stevioside sucralose (4,1',6'-trichloro-4,1',6'-trideoxygalactosucrose) or, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, such as from about 10% to 15% (weight/volume). The pharmaceutically acceptable flavours which can mask the bitter tasting ingredients in the low-dosage formulations comprise fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like.

Each flavour may be present in the final composition in a concentration ranging from about 0.05% to 1% (weight/volume). Combinations of said strong flavours are advantageously used. In some embodiments, a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the ligand-gated ion channels will easily determine the therapeutically effective amount of a compound of formula (I) from the test results presented hereinafter. In general it is contemplated that a therapeutically effective dose will be from about 0.001 mg/kg to about 50 mg/kg of body weight, such as from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible GPR120 receptor modulating response.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds (as well as stereoisomer(s) thereof and/or salt(s) thereof) described herein. The effective daily amount ranges mentioned hereinabove are therefore only guidelines.

Indications and Methods of Treatment

Also provided herein are: methods of treating CX3CR1-mediated disorders in a human or animal subject in need of such treatment, comprising administering to said subject an amount of a compound disclosed herein effective to reduce or prevent said disorder in the subject, alone or in combination with at least one additional agent for the treatment of said disorder that is known in the art. Certain embodiments provide therapeutic compositions comprising at least one compound disclosed herein, optionally in combination with one or more additional agents for the treatment of CX3CR1-mediated disorders.

Also provided herein are: the use of a compound of formula (I) or a pharmaceutically acceptable salt thereof as a medicament; the use of a compound of formula (I) or a pharmaceutically acceptable salt thereof in, or in the treatment of, a CX3CR1 mediated disease; the use of a compound of formula (I) or a pharmaceutically acceptable salt thereof in the manufacture of a medicament for the treatment of a CX3CR1 mediated disease; and a method of treatment of CX3CR1 mediated disease comprising administering a compound of formula (I) or a pharmaceutically acceptable salt thereof. Further provided herein is a method of treatment of a disease mediated by CX3CR1 activity, in a mammalian subject, which comprises administering a therapeutically effective amount of a compound of formula (I) or a pharmaceutically acceptable salt thereof.

CX3CR1-mediated diseases include proliferative disorders such as cancers, inflammatory disorders, pain, neurodegenerative disorders, cognitive and psychiatric disorders, and other diseases as disclosed below.

Compounds disclosed herein are useful for the treatment of neurodegenerative disorders of various origins such as Alzheimer's disease and other dementia conditions such as Lewy body dementia, fronto-temporal dementia and other taupathies; amyotrophic lateral sclerosis, multiple sclerosis, Parkinson's disease and other parkinsonian syndromes; HIV-induced neuroinflammation; essential tremors; other spinocerebellar degenerations and neuropathies such as Charcot-Marie-Tooth neuropathy. The compounds disclosed herein are also useful for the treatment of neurological conditions such as epilepsy including simple partial seizure, complex partial seizure, secondary generalized seizure, further including absence seizure, myoclonic seizure, clonic seizure, tonic seizure, tonic clonic seizure and atonic seizure, and for prevention and treatment of status epilepticus (SE).

The compounds disclosed herein are also useful for the treatment of cognitive disorders and of psychiatric disorders. Psychiatric disorders include, and are not limited to major depression, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behaviour, delusional disorders, brief psychotic disorders, shared psychotic disorders, psychotic disorder due to a general medical condition, substance-induced psychotic disorders or a psychotic disorder not otherwise specified, anxiety disorders such as generalised anxiety disorder, panic disorders, post-traumatic stress disorder, impulse control disorders, phobic disorders, dissociative states and moreover in smoke, drug addiction and alcoholism. In particular bipolar disorders, psychosis, anxiety and addiction.

The compounds disclosed herein are useful in the prevention or treatment of neuroinflammation and CNS damage induced by HIV infection and of HIV-associated neurocognitive deficits. The compounds disclosed herein are useful in the prevention or treatment of neuropathic pain. Neuropathic pain syndromes include, and are not limited to: chemotherapy-induced peripheral neuropathy, diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and peripheral forms of pain such as complex regional pain syndromes (CRPS) also called reflex sympathetic dystrophies.

The compounds disclosed herein are also useful for the treatment of pain, including chronic pain. Chronic pain includes, and is not limited to, chronic pain caused by inflammation or an inflammatory-related condition, ostheoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds disclosed herein are also useful in the treatment of acute pain caused by acute injury, illness, sport-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis or surgery (such as open heart or bypass surgery), post operative pain, kidney stone pain, gallbladder pain, gallstone pain, obstetric pain or dental pain.

The compounds disclosed herein are also useful in the treatment of headaches such as migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

Compounds disclosed herein are also useful in the treatment of diseases such as vertigo, tinnitus, muscle spasm, and other disorders including and not limited to cardiovascular diseases (such as cardiac arrhythmia, cardiac infarction or angina pectoris, hypertension, cardiac ischemia, cerebral ischemia) endocrine disorders (such as acromegaly or diabetes insipidus) diseases in which the pathophysiology of the disorder involves excessive or hypersecretory or otherwise inappropriate cellular secretion of an endogenous substance (such as catecholamine, a hormone or a growth factor).

The compounds disclosed herein are also useful in the selective treatment of liver disease, such as inflammatory liver diseases, for example chronic viral hepatitis B, chronic viral hepatitis C, alcoholic liver injury, primary biliary cirrhosis, autoimmune hepatitis, liver fibrosis, non-alcoholic steatohepatitis and liver transplant rejection.

The compounds disclosed herein inhibit inflammatory processes affecting all body systems. Therefore are useful in the treatment of inflammatory processes of the muscular-skeletal system of which the following is a list of examples but it is not comprehensive of all target disorders: arthritic conditions such as alkylosing spondylitis, cervical arthritis, fibromyalgia, gout, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis *nodosa*, thyroiditis, aplastic anaemia, scleroderma, myasthenia gravis, multiple sclerosis and other demyelinizating disorders, encephalomyelitis, sarcoidosis, nephritic syndrome, Bechet's syndrome, polymyositis, gingivitis.

Compounds disclosed herein are also useful in the treatment of gastrointestinal (GI) tract disorders such as inflammatory bowel disorders (IBD) including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyrosis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhoea, and visceral inflammation.

Compounds disclosed herein are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexities, pelvic inflammation, bartholinities and vaginitis. In particular, overactive bladder and urinary incontinence.

Compounds disclosed herein are also useful in the treatment of renal disorders such as ncluding diabetic nephropathy, renal allograft rejection, infectious renal diseases, IgA nephropathy, fibrotic kidney disease, lupus nephritis and glo-merulonephritis, acute kidney injury and renal carcinoma.

The compounds disclosed herein are also useful in the treatment of ophthalmic diseases such as retinitis, retinopathies, uveitis and acute injury to the eye tissue, age-related macular degeneration or glaucoma, conjunctivitis.

The compounds disclosed herein are also useful in the treatment of eating disorders such as anorexia nervosa including the subtypes restricting type and binge-eating/purging type; bulimia nervosa including the subtypes purging type and non-purging type; obesity; compulsive eating disorders; binge eating disorder; and eating disorder not otherwise specified.

The compounds disclosed herein are also useful in the treatment of allergie dermatitis, hyperresponsiveness of the airway, chronic obstructive pulmonary disease (COPD), bronchitis, septic shock, Sjögren's syndrome, glomerulonephritis, atherosclerosis, growth and metastases of malignant cells, myoblastic leukaemia, diabetes, meningitis, osteoporosis, burn injury, ischaemic heart disease, stroke, peripheral vascular disease, varicose veins, glaucoma.

In some embodiments, the compounds and pharmaceutical compositions of the present disclosure may be useful in the treatment or prevention of progression of cancer. The cancer may be a hematologic malignancy or solid tumor. Hematologic malignancies include leukemias, lymphomas, multiple myeloma, and subtypes thereof. Lymphomas can be classified various ways, often based on the underlying type of malignant cell, including Hodgkin's lymphoma (often cancers of Reed-Sternberg cells, but also sometimes originating in B cells; all other lymphomas are non-Hodgkin's lymphomas), B-cell lymphomas, T-cell lymphomas, mantle cell lymphomas, Burkitt's lymphoma, follicular lymphoma, and others as defined herein and known in the art.

B-cell lymphomas include, but are not limited to, diffuse large B-cell lymphoma (DLBCL), chronic lymphocytic leukemia (CLL)/small lymphocytic lymphoma (SLL), and others as defined herein and known in the art.

T-cell lymphomas include T-cell acute lymphoblastic leukemia/lymphoma (T-ALL), peripheral T-cell lymphoma (PTCL), T-cell chronic lymphocytic leukemia (T-CLL) Sezary syndrome, and others as defined herein and known in the art.

Leukemias include acute myeloid (or myelogenous) leukemia (AML), chronic myeloid (or myelogenous) leukemia (CML), acute lymphocytic (or lymphoblastic) leukemia (ALL), chronic lymphocytic leukemia (CLL) hairy cell leukemia (sometimes classified as a lymphoma) and others as defined herein and known in the art.

Plasma cell cell malignancies include lymphoplasmacytic lymphoma, plasmacytoma, and multiple myeloma.

Solid tumors include melanomas, neuroblastomas, gliomas or carcinomas such as tumors of the brain, head and neck, breast, lung (e.g., non-small cell lung cancer, NSCLC), reproductive tract (e.g., ovary), upper digestive tract, pancreas, liver, renal system (e.g., kidneys), bladder, prostate and colorectum.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

General Synthetic Methods

Compounds of formula (I) can be prepared according to the procedures described in the following general methods.

Abbreviations which are used in the description of the Schemes and the Examples that follows include:
Anh: Anhydrous
CC: Column Chromatography;
CDI: 1,1'-Carbonyldiimidazole;
$CH_2Cl_2$: Dichloromethane;
$CH_3CN$: Acetonitrile;
DBU: 1,5-diazabiciclo(5.4.0)undec-7-ene;
DMF: Dimethylformamide
DMSO: Dimethylsulfoxide
EtOAc: Ethyl acetate
EtOH: Ethanol
ESI: Electrospray ionization
HATU: 1-[Bis(dimethylamino)methylene]-1H-1,2,3-triazolo[4,5-b]pyridinium 3-oxid hexafluorophosphate;
h: hour;
$H_2O$: Water
HCl: hydrochloric acid
$K_2CO_3$: Potassium carbonate;
$LiAlH_4$: Lithium aluminium hydride
M: Molar
MeOH: Methanol
Min: Minute(s)
NMR: Nuclear Magnetic Resonance
NaOH: Sodium hydroxide;
$NaHCO_3$: Sodium bicarbonate
$Na_2SO_4$: Sodium solfate:
PyBop: Benzotriazol-1-yl-oxytripyrrolidinophosphonium hexafluorophosphate;
Pd/C: Palladium on carbon
rt: Room Temperature;
TFA: Trifluoroacetic acid;
THF: Tetrahydrofuran;
TEA: Triethylamine;
UPLC-MS: UltraPerformance LiquidChromatography-Mass Spectrometry In general, the nomenclature used in this Application is based on ChemSketch™ (ACDLabs) and generated according to the IUPAC systematic nomenclature. Chemical structures shown herein were prepared using ISIS® version 2.2. Certain compounds were drawn using CambridgeSoft's ChemDraw 18.0. Any open valency appearing on a carbon, oxygen, sulfur, or nitrogen atom in the structures herein indicates the presence of a hydrogen atom unless indicated otherwise. Where a nitrogen-containing heteroaryl ring is shown with an open valency on a nitrogen atom and variables such as $R^1$, $R^2$, $R^3$ etc. are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structure herein are intended to encompass all naturally occurring isotopes of such atoms. Thus, for example, the hydrogen atoms represented herein are meant to include deuterium and tritium, and the carbon atoms are meant to include $^{13}C$ and $^{14}C$ isotopes.

The following schemes can be used to practice the present invention.

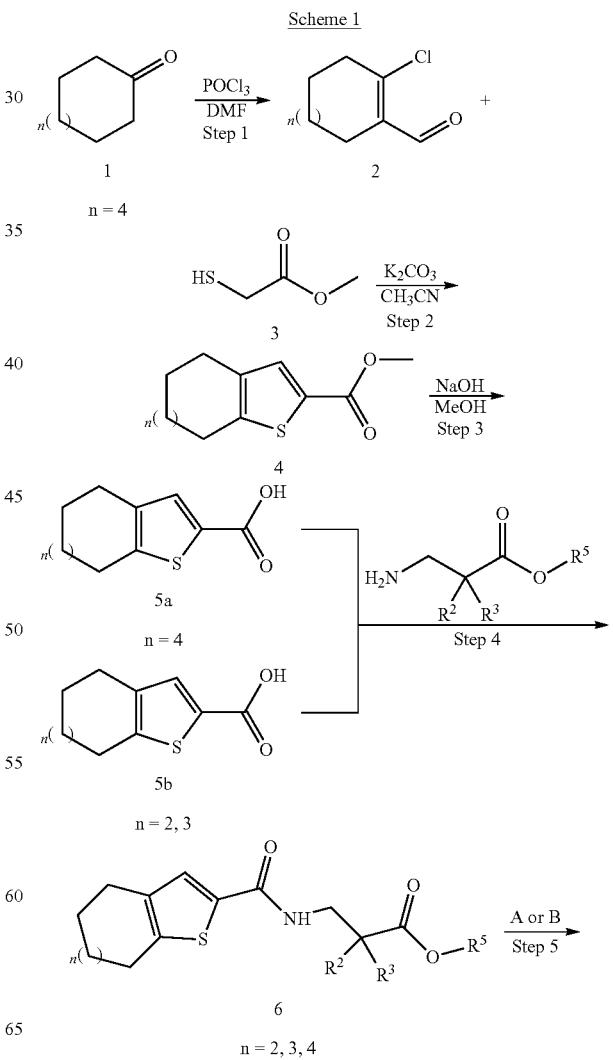

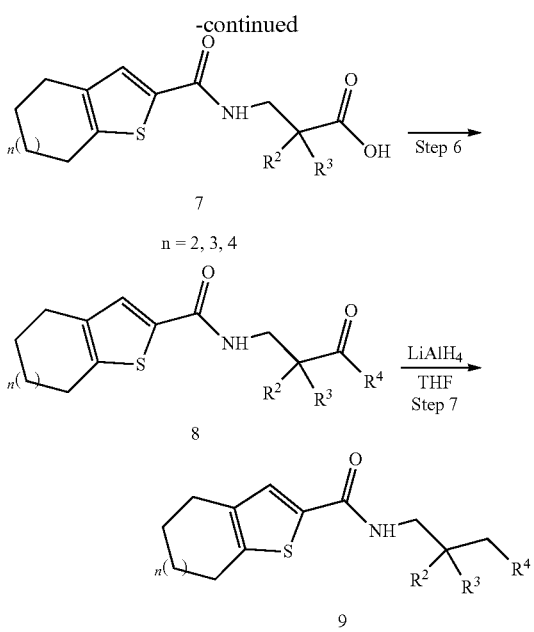

n = 2, 3, 4

Step 1. POCl$_3$ (2.0 eq) was added dropwise to anhydrous DMF (1.6 eq) at 0° C. with stirring under nitrogen atmosphere. After addition, the mixture was warmed to room temperature for 20 min, and re-cooled to 0° C. before the dropwise addition of 1 (1.0 eq). The resulting mixture was stirred overnight at room temperature, then poured over ice, neutralized with saturated aqueous NaHCO$_3$, and extracted with EtOAc (×3). Combined organic layers were washed with water (×3) and brine (×3), dried (Na$_2$SO$_4$), filtered, and dried under reduced pressure. The product was used for the next step without further purification.

Step 2. To a solution of 2 (1.0 eq) in CH$_3$CN, 3 (1.5 eq) and K$_2$CO$_3$ (3 eq) were added. The mixture was heated at reflux for 4 h and cooled to room temperature. H$_2$O was added and the mixture extracted with EtOAC (×3). The combined organic layers were washed with brine, dried (Na$_2$SO$_4$), filtered and evaporated under reduced pressure. The desired product was obtained after purification of the crude material as reported in the specific example.

Step 3. To a solution of 4 (1.0 eq) in MeOH 3N NaOH (3.0 eq) was added and the reaction mixture was stirred at room temperature overnight. The solvent was evaporated under reduced pressure, water was added and the solution extracted with EtOAC (×3). The aqueous phase was then acidified with 1N HCl and the product extracted with EtOAc (×3). The organic layer was washed with brine, dried (Na$_2$SO$_4$) and evaporated to give the desired product.

Step 4
Method A.
A mixture of 5b (1.0 eq) and 1,1'-carbonyldiimidazole (1.05 eq) in anhydrous THF was stirred at room temperature for 2 h. Then a solution of the appropriate P-aminoester (1.5 eq) in anhydrous THF was added, the reaction mixture was stirred at room temperature overnight and then heated to 55° C. for 6 h. The reaction mixture was diluted with water and extracted with EtOAC (×3). The combined organic layers were washed with brine (×3), dried (Na$_2$SO$_4$), filtered and evaporated under reduced pressure. The desired product was obtained after purification of the crude material as reported in the specific examples.

Method B.
To a solution of 5a or 5b (1.0 eq) in CH$_2$Cl$_2$ HATU (1.2 eq) was added and the mixture was stirred at room temperature for 10 min. Then the appropriate P-aminoester (1.2 eq) and TEA (3.0 eq) were added and the resulting mixture was stirred at room temperature overnight. The solvent was evaporated under reduced pressure. The desired product was obtained after purification of the crude material as reported in the specific examples.

Method C.
Thionyl chloride (3.0 eq) was added dropwise to a suspension of 5b (1.0 eq) in anhydrous toluene. The reaction mixture was stirred at rt for 1 h and then at 70° C. for 45 minutes. After cooling, the solvent was evaporated, the residue was dissolved in anhydrous CH$_2$Cl$_2$ and TEA (3.0 eq) and the appropriate P-aminoester (1.0 eq) were added. The reaction mixture was stirred at room temperature overnight. The solvent was evaporated under reduced pressure. The desired product was obtained after purification of the crude material as reported in the specific examples.

Step 5.
Method A.
To a solution of 6 (1.0 eq) in MeOH or EtOH 3N NaOH (3.0 eq) was added and the reaction mixture was stirred at room temperature overnight. The solvent was evaporated under reduced pressure, water was added and the solution extracted with EtOAC (×3). The aqueous phase was then acidified with 1N HCl and the product extracted with EtOAc (×3). The organic layer was washed with brine, dried (Na$_2$SO$_4$) and evaporated under reduced pressure. The product was used for the next step without further purification.

Method B.
To a 1M solution of 6 in CH$_2$Cl$_2$, TFA was added to reach an overall molarity of 0.5M and the resulting mixture stirred at room temperature for 3.5 h. The solvent was evaporated under vacuum and the resulting residue taken up in CH$_2$Cl$_2$. The product was used for the next step without further purification.

Step 6.
Method A.
To a solution of 7 (1.0 eq) in CH$_2$Cl$_2$ HATU (1.2 eq) was added and the mixture was stirred at room temperature for 10 min. Then the appropriate amine (1.2 eq) and TEA or DBU (3.0 eq) were added and the resulting mixture was stirred at room temperature overnight. The solvent was evaporated under reduced pressure. The desired product was obtained after purification of the crude material as reported in the specific examples.

Method B.
A mixture of 7 (1.0 eq) and 1,1'-carbonyldiimidazole (1.05 eq) in anhydrous THF was stirred at room temperature for 2 h. Then a solution of the appropriate P-aminoester (1.5 eq) in anhydrous THF was added, the reaction mixture was stirred at room temperature overnight and then heated to 55° C. for 6 h. The reaction mixture was diluted with water and extracted with EtOAC (×3). The combined organic layers were washed with brine (×3), dried (Na$_2$SO$_4$), filtered and evaporated under reduced pressure. The desired product was obtained after purification of the crude material as reported in the specific examples.

Step 7.
A solution of 8 in THF was cooled to 0° C. and LiAlH$_4$ was added dropwise. The reaction mixture was stirred at r.t. for 2 h, re-cooled to 0° C. and H$_2$O was added slowly. The precipitated was filtered and the solution extracted with EtOAC (×3). The combined organic layer was washed with brine, dried (Na$_2$SO$_4$), filtered and evaporated under reduced Scheme 2

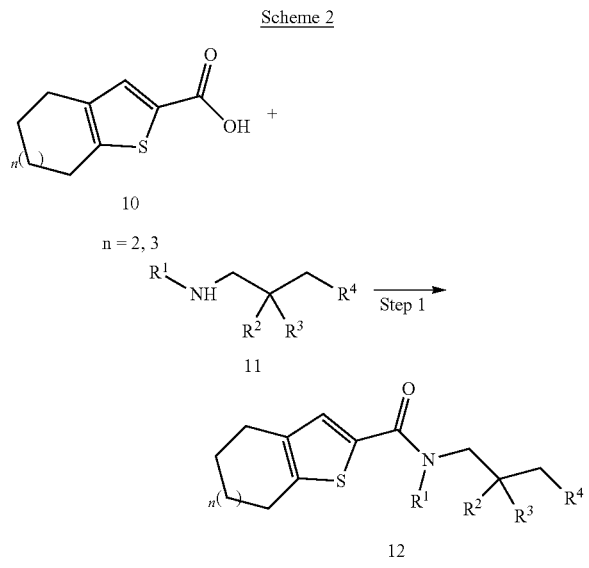

Step 1
Method A.

A mixture of 10 (1.0 eq) and 1,1'-carbonyldiimidazole (1.05 eq) in anhydrous THF was stirred at room temperature for 2 h. Then a solution of the appropriate amine (1.5 eq) in anhydrous THF was added, the reaction mixture was stirred at room temperature overnight and then heated to 55° C. for 6 h. The reaction mixture was diluted with water and extracted with EtOAC (×3). The combined organic layers were washed with brine (×3), dried ($Na_2SO_4$), filtered and evaporated under reduced pressure. The desired product was obtained after purification of the crude material as reported in the specific examples.

Method B.

To a solution of 10 (1.0 eq) in $CH_2Cl_2$ HATU (1.2 eq) was added and the mixture was stirred at room temperature for 10 min. Then the appropriate amine (1.2 eq) and TEA (3.0 eq) were added and the resulting mixture was stirred at room temperature overnight. The solvent was evaporated under reduced pressure. The desired product was obtained after purification of the crude material as reported in the specific examples.

Method C.

To a solution of 10 (1.0 eq) in anhydrous DMF, PyBOP (1.2 eq), TEA (3.0 eq) and the appropriate amine (1.0 eq) were added. The reaction mixture was stirred at rt overnight. The reaction mixture was diluted with $H_2O$ and extracted with EtOAc (×3). The combine organic layers were washed with brine (×5), dried ($Na_2SO_4$), filtered and evaporated. The desired product was obtained after purification of the crude material as reported in the specific examples.

Method D.

Thionyl chloride (3.0 eq) was added dropwise to a suspension of 10 (1.0 eq) in anhydrous toluene. The reaction mixture was stirred at rt for 1 h and then at 70° C. for 45 minutes. After cooling, the solvent was evaporated, the residue was dissolved in anhydrous $CH_2Cl_2$ and TEA (3.0 eq) and the appropriate amine (1.0 eq) were added. The reaction mixture was stirred at room temperature overnight. The solvent was evaporated under reduced pressure. The desired product was obtained after purification of the crude material as reported in the specific examples.

Scheme 3

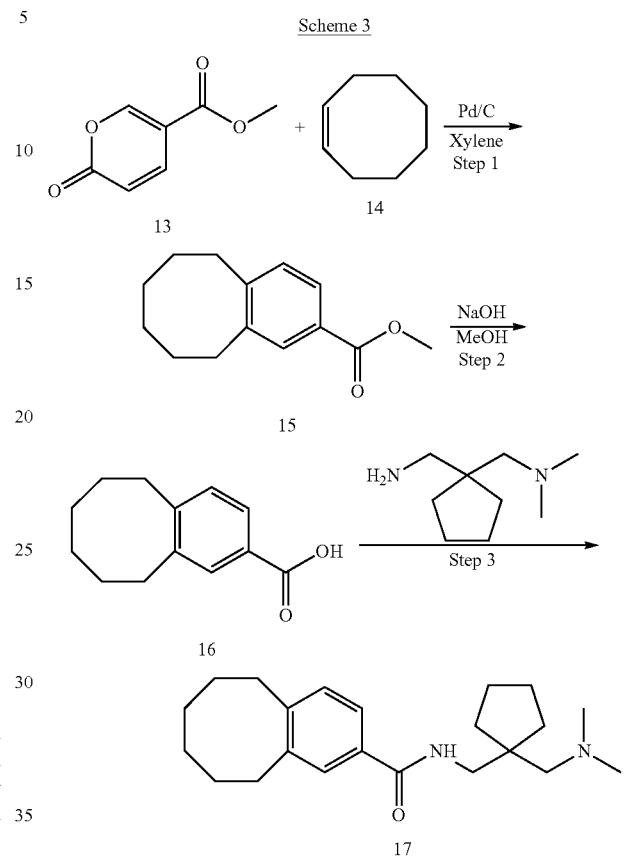

Step 1.

To a solution of 13 (1.0 eq) and 14 (5.0 eq) in xylene, Pd/C (0.36 eq) was added and the mixture was heated at reflux overnight. After cooling to room temperature the mixture was filtered on celite e the solvent evaporated under vacuum. The desired product was obtained after purification of the crude material as reported in the specific example.

Step 2.

To a solution of 15 (1.0 eq) in MeOH 3N NaOH (3.0 eq) was added and the reaction mixture was stirred at room temperature overnight. The solvent was evaporated under reduced pressure, water was added and the solution extracted with EtOAC (×3). The aqueous phase was then acidified with 1N HCl and the product extracted with EtOAc (×3). The organic layer was washed with brine, dried ($Na_2SO_4$) and evaporated under reduced pressure. The product was used for the next step without further purification.

Step 3.

To a solution of 16 (1.0 eq) in $CH_2Cl_2$ HATU (1.2 eq) was added and the mixture was stirred at room temperature for 10 min. Then the appropriate amine (1.2 eq) and TEA (3.0 eq) were added and the resulting mixture was stirred at room temperature overnight. The solvent was evaporated under reduced pressure. The desired product was obtained after purification of the crude material as reported in the specific example.

EXAMPLES

The invention is further illustrated by the following examples.

Example 1

N-[2,2-Dimethyl-3-(pyrrolidin-1-yl)propyl]-4H,5H,6H,7H,8H,9H-cycloocta[b]thiophene-2-carboxamide The title compound was prepared by the general procedure (scheme 2, step 1, method A) from 4,5,6,7,8,9-hexahydrocycloocta[b]thiophene-2-carboxylic acid (CAS: 40133-09-3) and CDI at room temperature for 2 hours. Then 2,2-dimethyl-3-(pyrrolidin-1-yl)propan-1-amine (CAS: 681247-27-8) was added and the resulting mixture was stirred at room temperature overnight and then heated to 55° C. for 6 hours. The crude product was purified by flash silica gel chromatography using a linear gradient of methanol in ethyl acetate from 0% to 15% (y=10%). Yellow solid.

Example 2

N-({1-[(Dimethylamino)methyl]cyclopentyl}methyl)-4H,5H,6H,7H,8H,9H-cycloocta[b]thiophene-2-carboxamide The title compound was prepared by the general procedure (scheme 2, step 1, method D) from 4,5,6,7,8,9-hexahydrocycloocta[b]thiophene-2-carboxylic acid (CAS: 40133-09-3) and {1-[(dimethylamino)methyl]cyclopentyl}methanamine (CAS: 1247566-89-7). The crude product was purified by flash silica gel chromatography using a linear gradient of methanol in dichloromethane from 0% to 15% (y=71%). Colourless oil.

Example 3

N-[3-(Dimethylamino)-2-methylpropyl]-4,5,6,7,8,9-hexahydrocycloocta[b]thiophene-2-carboxamide The title compound was prepared by the general procedure (scheme 2, step 1, method D) from 4,5,6,7,8,9-hexahydrocycloocta[b]thiophene-2-carboxylic acid (CAS: 40133-09-3) and (3-amino-2-methylpropyl)dimethylamine (CAS: 6105-72-2). The crude product was purified by RP-HPLC using a linear gradient of acetonitrile in water (with 0.05% of HCCOH) from 10 to 90% (y=45%). Yellow oil.

Example 4

N-{[1-(Pyrrolidin-1-ylmethyl)cyclopropyl]methyl}-4H,5H,6H,7H,8H,9H-cycloocta[b]thiophene-2-carboxamide The title compound was prepared by the general procedure (scheme 2, step 1, method C) from 4,5,6,7,8,9-hexahydrocycloocta[b]thiophene-2-carboxylic acid (CAS: 40133-09-3), PyBOP, TEA and 1-{1-[(pyrrolidin-1-yl)methyl]cyclopropyl}methanamine (CAS: 1001345-81-8). The resulting mixture was stirred at room temperature overnight. The crude product was purified by flash silica gel chromatography using a linear gradient of methanol in dichloromethane from 0% to 15% with TEA (0.2%) as additive. (y=41%). Yellow oil.

Example 5

N-{[1-(Pyrrolidin-1-ylmethyl)cyclopentyl]methyl}-4H,5H,6H,7H,8H,9H-cycloocta[b]thiophene-2-carboxamide Methyl 1-[[[(4H,5H,6H,7H,8H,9H-cycloocta[b]thiophen-2-ylcarbonyl)amino]methyl]cyclopentanecarboxylate (Intermediate 1)

The title compound was prepared by the general procedure (scheme 1, step 4, method A) from 4,5,6,7,8,9-hexahydrocycloocta[b]thiophene-2-carboxylic acid (CAS: 40133-09-3) and [1-(methoxycarbonyl)cyclopentyl]methanaminium chloride (CAS: 1481175-03-4). The crude product was purified by flash silica gel chromatography using a linear gradient of ethyl acetate in hexane from 0% to 70% (y=80%). White solid.

1-{[(4,5,6,7,8,9-Hexahydrocycloocta[b]thiophen-2-ylcarbonyl)amino]methyl}cyclopentanecarboxylic acid (Intermediate 2)

The title compound was prepared by the general procedure (scheme 1, step 5, method A) from Intermediate 1. Y=91%. White solid.

N-{[1-(Pyrrolidine-1-carbonyl)cyclopentyl]methyl}-4H,5H,6H,7H,8H,9H-cycloocta[b]thiophene-2-carboxamide (Intermediate 3)

The title compound was prepared by the general procedure (scheme 1, step 6, method B) from Intermediate 2 and pyrrolidine (CAS: 123-75-1). The crude product was purified by silica gel column chromatography using a linear gradient of ethyl acetate in hexane from 10% to 60% (y=69%). White solid.

N-{[1-(Pyrrolidin-1-ylmethyl)cyclopentyl]methyl}-4H,5H,6H,7H,8H,9H-cycloocta[b]thiophene-2-carboxamide The title compound was prepared by the general procedure (scheme 1, step 7) from Intermediate 3. The crude product was purified by silica gel column chromatography using a linear gradient of methanol in dichloromethane from 0% to 20% (y=69%). Colorless oil.

Example 6

N-[(1-{[Methyl(propyl)amino]methyl}cyclopentyl)methyl]-4H,5H,6H,7H,8H,9H-cycloocta[b]thiophene-2-carboxamide N-({1-[Methyl(propyl)carbamoyl]cyclopentyl}methyl)-4H,5H,6H,7H,8H,9H-cycloocta[b]thiophene-2-carboxamide (Intermediate 4)

The title compound was prepared by the general procedure (scheme 1, step 6, method B) from Intermediate 2 and N-methylpropanamine (CAS: 627-35-0). The crude product was purified by silica gel column chromatography using a linear gradient of ethyl acetate in hexane from 10% to 50% (y=67%). White solid.

N-[(1-{[Methyl(propyl)amino]methyl}cyclopentyl)methyl]-4H,5H,6H,7H,8H,9H-cycloocta[b]thiophene-2-carboxamide The title compound was prepared by the general procedure (scheme 1, step 7) from Intermediate 4. The crude product was purified by silica gel column chromatography using a linear gradient of methanol in dichloromethane from 0% to 20% (y=71%). Colorless oil.

Example 7

N-[3-(Dimethylamino)-2,2-dimethylpropyl]-N-methyl-4H,5H,6H,7H,8H,9H-cycloocta[b]thiophene-2-carboxamide The title compound was prepared by the general procedure (scheme 2, step 1, method C) from 4,5,6,7,8,9-hexahydrocycloocta[b]thiophene-2-carboxylic acid (CAS: 40133-09-3), PyBOP, TEA and $N^1,N^1,N^3,2,2$-pentamethylpropane-1,3-diamine (CAS: 85996-44-7). The resulting mixture was stirred at room temperature overnight. The crude product was purified by flash silica gel chromatography using a linear gradient of methanol in dichloromethane from 0% to 15% with TEA (0.2%) as additive. (y=38%). Colourless oil.

Example 8

N-{2-[(Dimethylamino)methyl]-2-ethylbutyl}-4H,5H,6H,7H,8H,9H-cycloocta[b]thiophene-2-carboxamide

Methyl 2-({4H,5H,6H,7H,8H,9H-cycloocta[b]thiophen-2-ylformamido}methyl)-2-ethylbutanoate (Intermediate 5)

The title compound was prepared by the general procedure (scheme 1, step 4, method A) from 4,5,6,7,8,9-hexahydrocycloocta[b]thiophene-2-carboxylic acid (CAS: 40133-09-3) and 2-ethyl-2-(methoxycarbonyl)butan-1-aminium chloride (CAS: 177269-36-2). The crude product was purified by flash silica gel chromatography using a linear gradient of ethyl acetate in hexane from 0% to 70% (y=87%). White solid.

2-({4H,5H,6H,7H,8H,9H-cycloocta[b]thiophen-2-ylformamido}methyl)-2-ethylbutanoic acid (Intermediate 6)

The title compound was prepared by the general procedure (scheme 1, step 5, method A) from Intermediate 5. Y=99%. White solid.

2-({4H,5H,6H,7H,8H,9H-Cycloocta[b]thiophen-2-ylformamido}methyl)-2-ethyl-N,N-dimethylbutanamide (Intermediate 7)

The title compound was prepared by the general procedure (scheme 1, step 6, method A) from Intermediate 6 and dimethylamine (CAS: 160-40-3). The crude product was purified by silica gel column chromatography using a linear gradient of ethyl acetate in hexane from 10% to 50% (y=81%). White solid.

N-{2-[(Dimethylamino)methyl]-2-ethylbutyl}-4H,5H,6H,7H,8H,9H-cycloocta[b]thiophene-2-carboxamide The title compound was prepared by the general procedure (scheme 1, step 7) from Intermediate 7. The crude product was purified by silica gel column chromatography using a linear gradient of methanol in dichloromethane from 0% to 20% (y=68%). Colorless oil.

Example 9

N-[2-Ethyl-2-(pyrrolidin-1-ylmethyl)butyl]-4H,5H,6H,7H,8H,9H-cycloocta[b]thiophene-2-carboxamide

N-[2,2-Diethyl-3-oxo-3-(pyrrolidin-1-yl)propyl]-4H,5H,6H,7H,8H,9H-cycloocta[b]thiophene-2-carboxamide (Intermediate 8)

The title compound was prepared by the general procedure (scheme 1, step 6, method A) from Intermediate 6 and pyrrolidine (CAS: 123-75-1). The crude product was purified by silica gel column chromatography using a linear gradient of ethyl acetate in hexane from 10% to 50% (y=87%). White solid.

N-[2-Ethyl-2-(pyrrolidin-1-ylmethyl)butyl]-4H,5H,6H,7H,8H,9H-cycloocta[b]thiophene-2-carboxamide The title compound was prepared by the general procedure (scheme 1, step 7) from Intermediate 8. The crude product was purified by silica gel column chromatography using a linear gradient of methanol in dichloromethane from 0% to 20% (y=71%). Colorless oil.

Example 10

N-({2-[(Dimethylamino)methyl]-2,3-dihydro-1H-inden-2-yl}methyl)-4H,5H,6H,7H,8H,9H-cycloocta[b]thiophene-2-carboxamide

[2-(Methoxycarbonyl)-2,3-dihydro-1H-inden-2-yl]methanaminium chloride (Intermediate 9)

Thionyl chloride was added to a cooled (0° C.) solution of 2-aminomethyl-indan-2-carboxylic acid hydrochloride (CAS: 1360547-49-4) in methanol. The reaction was heated to reflux temperature and stirred for 3 h. After cooling, the volatiles were evaporated and the residue was used for the next step without further purification.

Methyl 2-({4H,5H,6H,7H,8H,9H-cycloocta[b]thiophen-2-ylformamido}methyl)-2,3-dihydro-1H-indene-2-carboxylate (Intermediate 10)

The title compound was prepared by the general procedure (scheme 1, step 4, method A) from 4,5,6,7,8,9-hexahydrocycloocta[b]thiophene-2-carboxylic acid (CAS: 40133-09-3) and Intermediate 9. The crude product was purified by flash silica gel chromatography using a linear gradient of ethyl acetate in hexane from 0% to 30% (y=84%). White solid.

2-({4H,5H,6H,7H,8H,9H-cycloocta[b]thiophen-2-ylformamido}methyl)-2,3-dihydro-1H-indene-2-carboxylic acid (Intermediate 11)

The title compound was prepared by the general procedure (scheme 1, step 5, method A) from Intermediate 10. Y=99%. White solid.

N-{[2-(Dimethylcarbamoyl)-2,3-dihydro-1H-inden-2-yl]methyl}-4H,5H,6H,7H,8H,9H-cycloocta[b]thiophene-2-carboxamide (Intermediate 12)

The title compound was prepared by the general procedure (scheme 1, step 6, method A) from Intermediate 11 and dimethylamine (CAS: 160-40-3). The crude product was purified by silica gel column chromatography using a linear gradient of ethyl acetate in hexane from 10% to 50% (y=81%). White solid.

N-({2-[(Dimethylamino)methyl]-2,3-dihydro-1H-inden-2-yl}methyl)-4H,5H,6H,7H,8H,9H-cycloocta[b]thiophene-2-carboxamide The title compound was prepared by the general procedure (scheme 1, step 7) from Intermediate 12. The crude product was purified by silica gel column chromatography using a linear gradient of methanol in dichloromethane from 0% to 8% (y=59%). Colorless oil.

Example 11

N-{[2-(Pyrrolidin-1-ylmethyl)-2,3-dihydro-1H-inden-2-yl]methyl}-4H,5H,6H,7H,8H,9H-cycloocta[b]thiophene-2-carboxamide

N-{[2-(Pyrrolidine-1-carbonyl)-2,3-dihydro-1H-inden-2-yl]methyl}-4H,5H,6H,7H,8H,9H-cycloocta[b]thiophene-2-carboxamide (Intermediate 13)

The title compound was prepared by the general procedure (scheme 1, step 6, method A) from Intermediate 10 and pyrrolidine (CAS: 123-75-1). The crude product was purified by silica gel column chromatography using a linear gradient of ethyl acetate in hexane from 10% to 50% (y=87%). White solid.

N-{[2-(Pyrrolidin-1-ylmethyl)-2,3-dihydro-1H-inden-2-yl]methyl}-4H,5H,6H,7H,8H,9H-cycloocta[b]thiophene-2-carboxamide The title compound was prepared by the general procedure (scheme 1, step 7) from Intermediate 13. The crude product was purified by silica gel column chromatography using a linear gradient of methanol in dichloromethane from 0% to 8% (y=61%). Colorless oil.

Example 12

N-({1-[(Diethylamino)methyl]cyclopentyl}methyl)-4H,5H,6H,7H,8H,9H-cycloocta[b]thiophene-2-carboxamide

N-{[1-(Diethylcarbamoyl)cyclopentyl]methyl}-4H,5H,6H,7H,8H,9H-cycloocta[b]thiophene-2-carboxamide (Intermediate 14)

The title compound was prepared by the general procedure (scheme 1, step 6, method A) from Intermediate 2 and diethylamine (CAS: 109-89-7). The crude product was purified by silica gel column chromatography using a linear gradient of ethyl acetate in hexane from 10% to 50% (y=91%). White solid.

N-({1-[(Diethylamino)methyl]cyclopentyl}methyl)-4H,5H,6H,7H,8H,9H-cycloocta[b]thiophene-2-carboxamide The title compound was prepared by the general procedure (scheme 1, step 7) from Intermediate 14. The crude product was purified by silica gel column chromatography using a linear gradient of methanol in dichloromethane from 0% to 8% (y=68%). Colorless oil.

Example 13

N-[2,2-Dimethyl-3-(piperidin-1-yl)propyl]-4H,5H,6H,7H,8H,9H-cycloocta[b]thiophene-2-carboxamide

Methyl 3-[(4H,5H,6H,7H,8H,9H-cycloocta[b]thiophen-2-ylcarbonyl)amino]-2,2-dimethylpropionate (Intermediate 15)

The title compound was prepared by the general procedure (scheme 1, step 4, Method C) from 4,5,6,7,8,9-hexahydrocycloocta[b]thiophene-2-carboxylic acid (CAS: 40133-09-3) and methyl 3-amino-2,2-dimethylpropanoate hydrochloride (CAS: 177269-37-3). The crude product was purified by flash silica gel chromatography using a linear gradient of ethyl acetate in hexane from 0% to 70% (y=92%). White solid.

3-{4H,5H,6H,7H,8H,9H-Cycloocta[b]thiophen-2-ylformamido}-2,2-dimethylpropanoic acid (Intermediate 16)

The title compound was prepared by the general procedure (scheme 1, step 5, method A) from Intermediate 15. Y=88%. White solid.

N-[2,2-Dimethyl-3-oxo-3-(piperidin-1-yl)propyl]-4H,5H,6H,7H,8H,9H-cycloocta[b]thiophene-2-carboxamide (Intermediate 17)

The title compound was prepared by the general procedure (scheme 1, step 6, method A) from Intermediate 16 and piperidine (CAS: 110-89-4). The crude product was purified by silica gel column chromatography using a linear gradient of ethyl acetate in hexane from 5% to 70% (y=93%). White solid.

N-[2,2-Dimethyl-3-(piperidin-1-yl)propyl]-4H,5H,6H,7H,8H,9H-cycloocta[b]thiophene-2-carboxamide The title compound was prepared by the general procedure (scheme 1, step 7) from Intermediate 17. The crude product was purified by silica gel column chromatography using a linear gradient of ethyl acetate in hexane from 10% to 60% (y=82%). Colorless oil.

Example 14

N-{[1-(Azetidin-1-ylmethyl)cyclopentyl]methyl}-4H,5H,6H,7H,8H,9H-cycloocta[b]thiophene-2-carboxamide

N-{[1-(Azetidine-1-carbonyl)cyclopentyl]methyl}-4H,5H,6H,7H,8H,9H-cycloocta[b]thiophene-2-carboxamide (Intermediate 18)

The title compound was prepared by the general procedure (scheme 1, step 6, method A) from Intermediate 2 and azetidine hydrochloride (CAS: 6674-22-2). The crude product was purified by silica gel column chromatography using a linear gradient of ethyl acetate in hexane from 10% to 50% (y=84%). White solid.

N-{[1-(Azetidin-1-ylmethyl)cyclopentyl]methyl}-4H,5H,6H,7H,8H,9H-cycloocta[b]thiophene-2-carboxamide The title compound was prepared by the general procedure (scheme 1, step 7) from Intermediate 18. The crude product was purified by silica gel column chromatography using a linear gradient of methanol in dichloromethane from 0% to 8% (y=89%). Colorless oil.

Example 15

N-{[1-(Piperidin-1-ylmethyl)cyclopentyl]methyl}-4H,5H,6H,7H,8H,9H-cycloocta[b]thiophene-2-carboxamide N-{[1-(Piperidine-1-carbonyl)cyclopentyl]methyl}-4H,5H,6H,7H,8H,9H-cycloocta[b]thiophene-2-carboxamide (Intermediate 19)

The title compound was prepared by the general procedure (scheme 1, step 6, method A) from Intermediate 2 and piperidine (CAS: 110-89-4). The crude product was purified by silica gel column chromatography using a linear gradient of ethyl acetate in hexane from 10% to 50% (y=84%). White solid.

N-{[1-(Piperidin-1-ylmethyl)cyclopentyl]methyl}-4H,5H,6H,7H,8H,9H-cycloocta[b]thiophene-2-carboxamide The title compound was prepared by the general procedure (scheme 1, step 7) from Intermediate 19. The crude product was purified by silica gel column chromatography using a linear gradient of methanol in dichloromethane from 0% to 20% (y=89%). Colorless oil.

Example 16

N-[3-(Diethylamino)-2,2-dimethylpropyl]-4H,5H,6H,7H,8H,9H-cycloocta[b]thiophene-2-carboxamide 3-{4H,5H,6H,7H,8H,9H-Cycloocta[b]thiophen-2-ylformamido}-N,N-diethyl-2,2-dimethylpropanamide (Intermediate 20)

The title compound was prepared by the general procedure (scheme 1, step 6, method A) from Intermediate 16 and diethylamine (CAS: 109-89-7). The crude product was purified by silica gel column chromatography using a linear gradient of ethyl acetate in hexane from 10% to 80% (y=83%). White solid.

N-[3-(Diethylamino)-2,2-dimethylpropyl]-4H,5H,6H,7H,8H,9H-cycloocta[b]thiophene-2-carboxamide The title compound was prepared by the general procedure (scheme 1, step 7) from Intermediate 20. The crude product was purified by silica gel column chromatography using a linear gradient of methanol in dichloromethane from 2% to 16% (y=39%). Yellow oil.

Example 17

N-[(1-{[(2-Hydroxyethyl)(methyl)amino]methyl}cyclopentyl)methyl]-4H,5H,6H,7H,8H,9H-cycloocta[b]thiophene-2-carboxamide N-({1-[(2-Hydroxyethyl)(methyl)carbamoyl]cyclopentyl}methyl)-4H,5H,6H,7H,8H,9H-cycloocta[b]thiophene-2-carboxamide (Intermediate 21)

The title compound was prepared by the general procedure (scheme 1, step 6, method A) from Intermediate 2 and 2-(methylamino)ethanol (CAS: 109-83-1). The crude product was purified by silica gel column chromatography using a linear gradient of ethyl acetate in hexane from 50% to 100% (y=51%). White solid.

N-[(1-{[(2-Hydroxyethyl)(methyl)amino]methyl}cyclopentyl)methyl]-4H,5H,6H,7H,8H,9H-cycloocta[b]thiophene-2-carboxamide The title compound was prepared by the general procedure (scheme 1, step 7) from Intermediate 21. The crude product was purified by silica gel column chromatography using a linear gradient of methanol in dichloromethane from 0% to 20% (y=79%). Colorless oil.

Example 18

N-{[1-(Pyrrolidin-1-ylmethyl)cyclohexyl]methyl}-4H,5H,6H,7H,8H,9H-cycloocta[b]thiophene-2-carboxamide Methyl 1-({4H,5H,6H,7H,8H,9H-cycloocta[b]thiophen-2-ylformamido}methyl)cyclohexane-1-carboxylate (Intermediate 22)

The title compound was prepared by the general procedure (scheme 1, step 4, method A) from 4,5,6,7,8,9-hexahydrocycloocta[b]thiophene-2-carboxylic acid (CAS: 40133-09-3) and [1-(methoxycarbonyl)cyclohexyl]methanaminium chloride (CAS: 227203-36-3). The crude product was purified by flash silica gel chromatography using a linear gradient of ethyl acetate in hexane from 0% to 40% (y=67%). White solid.

1-({4H,5H,6H,7H,8H,9H-Cycloocta[b]thiophen-2-ylformamido}methyl)cyclohexane-1-carboxylic acid (Intermediate 23)

The title compound was prepared by the general procedure (scheme 1, step 5, method A) from Intermediate 22. Y=90%. White solid.

N-{[1-(Pyrrolidine-1-carbonyl)cyclohexyl]methyl}-4H,5H,6H,7H,8H,9H-cycloocta[b]thiophene-2-carboxamide (Intermediate 24)

The title compound was prepared by the general procedure (scheme 1, step 6, method A) from Intermediate 23 and pyrrolidine (CAS: 123-75-1). The crude product was purified by silica gel column chromatography using a linear gradient of ethyl acetate in hexane from 10% to 60% (y=86%). White solid.

N-{[1-(Pyrrolidin-1-ylmethyl)cyclohexyl]methyl}-4H,5H,6H,7H,8H,9H-cycloocta[b]thiophene-2-carboxamide The title compound was prepared by the general procedure (scheme 1, step 7) from Intermediate 24. The crude product was purified by silica gel column chromatography using a linear gradient of ethyl acetate in hexane from 30% to 100% (y=52%). Colorless oil.

Example 19

N-({4-[(Dimethylamino)methyl]oxan-4-yl}methyl)-4H,5H,6H,7H,8H,9H-cycloocta[b]thiophene-2-carboxamide Methyl 4-[[(4H,5H,6H,7H,8H,9H-cycloocta[b]thiophen-2-ylcarbonyl)amino]methyl]oxane-4-carboxylate (Intermediate 25)

The title compound was prepared by the general procedure (scheme 1, step 4, method A) from 4,5,6,7,8,9-hexahydrocycloocta[b]thiophene-2-carboxylic acid (CAS: 40133-09-3) and methyl 4-(aminomethyl)oxane-4-carboxylate hydrochloride (CAS: 362707-24-2). The crude product was purified by flash silica gel chromatography using a linear gradient of ethyl acetate in hexane from 0% to 60% (y=76%). White solid.

4-[[(4,5,6,7,8,9-Hexahydrocycloocta[b]thiophen-2-ylcarbonyl)amino]methyl]oxane-4-carboxylic acid (Intermediate 26)

The title compound was prepared by the general procedure (scheme 1, step 5, method A) from Intermediate 25. Y=93%. White solid.

4-[[(4,5,6,7,8,9-Hexahydrocycloocta[b]thiophen-2-ylcarbonyl)amino]methyl]-N,N-dimethyloxane-4-carboxamide (Intermediate 27)

The title compound was prepared by the general procedure (scheme 1, step 6, method A) from Intermediate 26 and dimethylamine (CAS: 160-40-3). The crude product was purified by silica gel column chromatography using a linear gradient of ethyl acetate in hexane from 10% to 55% (y=80%). White solid.

N-({4-[(Dimethylamino)methyl]oxan-4-yl}methyl)-4H,5H,6H,7H,8H,9H-cycloocta[b]thiophene-2-carboxamide The title compound was prepared by the general procedure (scheme 1, step 7) from Intermediate 27. The crude product was purified by silica gel column chromatography using a linear gradient of ethyl acetate in hexane from 30% to 100% (y=25%). Colorless oil.

Example 20

N-{[4-(Pyrrolidin-1-ylmethyl)oxan-4-yl]methyl}-4H,5H,6H,7H,8H,9H-cycloocta[b]thiophene-2-carboxamide N-{[4-(Pyrrolidine-1-carbonyl)oxan-4-yl]methyl}-4H,5H,6H,7H,8H,9H-cycloocta[b]thiophene-2-carboxamide (Intermediate 28)

The title compound was prepared by the general procedure (scheme 1, step 6, method A) from Intermediate 26 and pyrrolidine (CAS: 123-75-1). The crude product was purified by silica gel column chromatography using a linear gradient of ethyl acetate in hexane from 10% to 55% (y=62%). Colorless oil.

N-{[4-(Pyrrolidin-1-ylmethyl)oxan-4-yl]methyl}-4H,5H,6H,7H,8H,9H-cycloocta[b]thiophene-2-carboxamide The title compound was prepared by the general procedure (scheme 1, step 7) from Intermediate 28. The crude product was purified by silica gel column chromatography using a linear gradient of ethyl acetate in hexane from 30% to 100% (y=28%). Colorless oil.

Example 21

N-{[1-(Pyrrolidin-1-ylmethyl)cyclobutyl]methyl}-4H,5H,6H,7H,8H,9H-cycloocta[b]thiophene-2-carboxamide Methyl 1-[[(4,5,6,7,8,9-hexahydrocycloocta[b]thiophen-2-ylcarbonyl)amino]methyl]cyclobutanecarboxylate (Intermediate 29)

The title compound was prepared by the general procedure (scheme 1, step 4, method B) from 4,5,6,7,8,9-hexahydrocycloocta[b]thiophene-2-carboxylic acid (CAS: 40133-09-3) and [1-(methoxycarbonyl)cyclobutyl]methanaminium chloride (CAS: 1172902-07-6). The crude product was purified by flash silica chromatography using a linear gradient of ethyl acetate in hexane from 0% to 50% (y=94%). White solid.

1-[[(4,5,6,7,8,9-hexahydrocycloocta[b]thiophen-2-ylcarbonyl)amino]methyl]cyclobutanecarboxylic acid (Intermediate 30)

The title compound was prepared by the general procedure (scheme 1, step 5, method A) from Intermediate 29. Y=99%. White solid.

N-{[1-(Pyrrolidine-1-carbonyl)cyclobutyl]methyl}-4H,5H,6H,7H,8H,9H-cycloocta[b]thiophene-2-carboxamide (Intermediate 31)

The title compound was prepared by the general procedure (scheme 1, step 6, method A) from intermediate 30 and HATU at room temperature for 10 min. Then pyrrolidine (CAS: 123-75-1) and TEA were added and the resulting mixture was stirred at room temperature overnight. The crude product was purified by flash silica gel chromatography using a linear gradient of ethyl acetate in hexane from 0% to 100% (y=82%). Colourless oil.

N-{[1-(Pyrrolidin-1-ylmethyl)cyclobutyl]methyl}-4H,5H,6H,7H,8H,9H-cycloocta[b]thiophene-2-carboxamide The title compound was prepared by the general procedure (scheme 1, step 7) from intermediate 31 and LiAlH$_4$. The crude product was purified by flash silica gel chromatography using a linear gradient of ethyl acetate in hexane from 20% to 100% (y=67%). Colourless oil.

Example 22

N-({1-[(Dimethylamino)methyl]cyclohexyl}methyl)-4H,5H,6H,7H,8H,9H-cycloocta[b]thiophene-2-carboxamide N-{[1-(Dimethylcarbamoyl)cyclohexyl]methyl}-4H,5H,6H,7H,8H,9H-cycloocta[b]thiophene-2-carboxamide (Intermediate 32)

The title compound was prepared by the general procedure (scheme 1, step 6, method A) from Intermediate 23 and dimethylamine (CAS: 160-40-3). The crude product was purified by silica gel column chromatography using a linear gradient of ethyl acetate in hexane from 10% to 60% (y=87%). White solid.

N-({1-[(Dimethylamino)methyl]cyclohexyl}methyl)-4H,5H,6H,7H,8H,9H-cycloocta[b]thiophene-2-carboxamide The title compound was prepared by the general procedure (scheme 1, step 7) from intermediate 32 and LiAlH$_4$. The crude product was purified by flash silica gel chromatography using a linear gradient of ethyl acetate in hexane from 50% to 100% (y=68%). Yellowish oil.

Example 23

N-({1-[(Dimethylamino)methyl]cyclobutyl}methyl)-4H,5H,6H,7H,8H,9H-cycloocta[b]thiophene-2-carboxamide N-[[1-(Dimethylaminocarbonyl)cyclobutyl]methyl]-4,5,6,7,8,9-hexahydrocycloocta[b]thiophene-2-carboxamide (Intermediate 33)

The title compound was prepared by the general procedure (scheme 1, step 6, method A) from Intermediate 30 and dimethylamine (CAS: 160-40-3). The crude product was purified by silica gel column chromatography using a linear gradient of ethyl acetate in hexane from 10% to 80% (y=88%). White solid N-({1-[(Dimethylamino)methyl]cyclobutyl}methyl)-4H,5H,6H,7H,8H,9H-cycloocta[b]thiophene-2-carboxamide The title compound was prepared by the general procedure (scheme 1, step 7) from intermediate 33 and LiAlH$_4$. The crude product was purified by flash silica gel chromatography using a linear gradient of ethyl acetate in hexane from 50% to 100% (y=30%). Yellowish oil.

Example 24

N-[2,2-Dimethyl-3-(pyrrolidin-1-yl)propyl]-4H,5H,6H,7H,8H,9H,10H-cyclonona[b]thiophene-2-carboxamide (1Z)-2-Chlorocyclonon-1-ene-1-carbaldehyde (Intermediate 34)

The title compound was prepared by general procedure (scheme 1, step 1) from Cyclooctanone (CAS: 502-49-8). The crude product was used for the next step.

Methyl 5,6,7,8,9,10-hexahydro-4H-cyclonona[b]thiophene-2-carboxylate (Intermediate 35)

The title compound was prepared by general procedure (scheme 1, step 2) from intermediate 34 and methyl thioglycolate (CAS: 2365-48-2). The crude product was purified by flash silica gel chromatography using a linear gradient of ethyl acetate in hexane from 0% to 10% (y=21%). Colourless oil.

5,6,7,8,9,10-Hexahydro-4H-cyclonona[b]thiophene-2-carboxylic acid (Intermediate 36)

The title compound was prepared by the general procedure (scheme 1, step 3) from Intermediate 35 and 3N NaOH. The product was obtained pure (y=91%). White solid.

N-[2,2-Dimethyl-3-(pyrrolidin-1-yl)propyl]-4H,5H,6H,7H,8H,9H,10H-cyclonona[b]thiophene-2-carboxamide The title compound was prepared by the general procedure (scheme 2, step 1, method B) from Intermediate 36 and 2,2-dimethyl-3-(pyrrolidin-1-yl)propan-1-amine (CAS: 681247-27-8). The crude product was purified by flash silica gel chromatography using a linear gradient of ethyl acetate in hexane from 50% to 100% (y=82%). Colourless oil.

Example 25

N-({1-[(3-Hydroxypyrrolidin-1-yl)methyl]cyclopentyl}methyl)-4H,5H,6H,7H,8H,9H-cycloocta[b]thiophene-2-carboxamide N-{[1-(3-Hydroxypyrrolidine-1-carbonyl)cyclopentyl]methyl}-4H,5H,6H,7H,8H,9H-cycloocta[b]thiophene-2-carboxamide (Intermediate 37)

The title compound was prepared by the general procedure (scheme 1, step 6, method A) from Intermediate 2 and pyrrolidin-3-ol hydrochloride (CAS: 86070-82-8). The crude product was purified by silica gel column chromatography using a linear gradient of methanol in dichloromethane from 0% to 15% (y=75%). White solid.

N-({1-[(3-Hydroxypyrrolidin-1-yl)methyl]cyclopentyl}methyl)-4H,5H,6H,7H,8H,9H-cycloocta[b]thiophene-2-carboxamide The title compound was prepared by the general procedure (scheme 1, step 7) from intermediate 37 and LiAlH$_4$. The crude product was purified by flash silica gel chromatography using a linear gradient of ethyl acetate in hexane from 0% to 15% (y=85%). Colorless oil.

Example 26

N-{[1-(Pyrrolidin-1-ylmethyl)cyclobutyl]methyl}-4H,5H,6H,7H,8H,9H,10H-cyclonona[b]thiophene-2-carboxamide Methyl 1-[[(5,6,7,8,9,10-hexahydro-4-{H}-cyclonona[b]thiophen-2-ylcarbonyl)amino]methyl]cyclobutanecarboxylate (Intermediate 38)

The title compound was prepared by the general procedure (scheme 1, step 4, method B) from Intermediate 36 and methyl [1-(aminomethyl)cyclobutyl]acetate (CAS: 1027337-70-7). The crude product was purified by flash silica gel chromatography using a linear gradient of ethyl acetate in hexane from 10% to 50% (y=82%). White solid.

1-[[(5,6,7,8,9,10-Hexahydro-4H-cyclonona[b]thiophen-2-ylcarbonyl)amino]methyl]cyclobutanecarboxylic acid (Intermediate 39)

The title compound was prepared by the general procedure (scheme 1, step 5, method A) from Intermediate 38 and 3N NaOH. The product was obtained pure (y=87%). White solid.

N-{[1-(Pyrrolidine-1-carbonyl)cyclobutyl]methyl}-4H,5H,6H,7H,8H,9H,10H-cyclonona[b]thiophene-2-carboxamide (Intermediate 40)

The title compound was prepared by the general procedure (scheme 1, step 6, method A) from Intermediate 39 and pyrrolidine (CAS: 123-75-1). The crude product was purified by flash silica gel chromatography using a linear gradient of ethyl acetate in hexane from 30% to 100% (y=80%). Colourless oil.

N-{[1-(Pyrrolidin-1-ylmethyl)cyclobutyl]methyl}-4H,5H,6H,7H,8H,9H,10H-cyclonona[b]thiophene-2-carboxamide. The title compound was prepared by the general procedure (scheme 1, step 7) from Intermediate 40 and LiAlH$_4$. The crude product was purified by flash silica gel chromatography using a linear gradient of ethyl acetate in hexane from 30% to 100% (y=62%). Colourless oil.

Example 27

N-({1-[(3-Hydroxypiperidin-1-yl)methyl]cyclopentyl}methyl)-4H,5H,6H,7H,8H,9H-cycloocta[b]thiophene-2-carboxamide N-{[1-(3-Hydroxypiperidine-1-carbonyl)cyclopentyl]methyl}-4H,5H,6H,7H,8H,9H-cycloocta[b]thiophene-2-carboxamide (Intermediate 41)

The title compound was prepared by the general procedure (scheme 1, step 6, method A) from Intermediate 2 and piperidin-3-ol (CAS: 6859-99-0). The crude product was purified by silica gel column chromatography using a linear gradient of methanol in dichloromethane from 0% to 15% (y=78%). White solid.

N-({1-[(3-Hydroxypiperidin-1-yl)methyl]cyclopentyl}methyl)-4H,5H,6H,7H,8H,9H-cycloocta[b]thiophene-2-carboxamide The title compound was prepared by the general procedure (scheme 1, step 7) from Intermediate 41 and LiAlH$_4$. The crude product was purified by flash silica gel chromatography using a linear gradient of ethyl acetate in hexane from 0% to 15% (y=82%). Colorless oil.

Example 28

N-({1-[(4-Hydroxypiperidin-1-yl)methyl]cyclopentyl}methyl)-4H,5H,6H,7H,8H,9H-cycloocta[b]thiophene-2-carboxamide N-{[1-(4-Hydroxypiperidine-1-carbonyl)cyclopentyl]methyl}-4H,5H,6H,7H,8H,9H-cycloocta[b]thiophene-2-carboxamide (Intermediate 42)

The title compound was prepared by the general procedure (scheme 1, step 6, method A) from Intermediate 2 and piperidin-3-ol (CAS: 6859-99-0). The crude product was purified by silica gel column chromatography using a linear gradient of methanol in dichloromethane from 0% to 15% (y=78%). White solid.

N-({1-[(4-Hydroxypiperidin-1-yl)methyl]cyclopentyl}methyl)-4H,5H,6H,7H,8H,9H-cycloocta[b]thiophene-2-carboxamide The title compound was prepared by the general procedure (scheme 1, step 7) from Intermediate 42 and LiAlH$_4$. The crude product was purified by flash silica gel chromatography using a linear gradient of ethyl acetate in hexane from 0% to 15% (y=70%). Colorless oil.

Example 29

N-[(1-{[(2-Hydroxyethyl)(methyl)amino]methyl}cyclopentyl)methyl]-4H,5H,6H,7H,8H,9H,10H-cyclonona[b]thiophene-2-carboxamide Methyl 1-[[(5,6,7,8,9,10-hexahydro-4H-cyclonona[b]thiophen-2-ylcarbonyl)amino]methyl]cyclopentanecarboxylate (Intermediate 43)

The title compound was prepared by the general procedure (scheme 1, step 4, method B) from Intermediate 36 and methyl [1-(aminomethyl)cyclopentyl]acetate (CAS: 99092-03-2). The crude product was purified by flash silica gel chromatography using a linear gradient of ethyl acetate in hexane from 10% to 50% (y=79%). White solid.

1-[[(5,6,7,8,9,10-Hexahydro-4H-cyclonona[b]thiophen-2-ylcarbonyl)amino]methyl]cyclopentanecarboxylic acid (Intermediate 44)

The title compound was prepared by the general procedure (scheme 1, step 5, method A) from Intermediate 43 and 3N NaOH. The product was obtained pure (y=91%). White solid.

N-({1-[(2-Hydroxyethyl)(methyl)carbamoyl]cyclopentyl}methyl)-4H,5H,6H,7H,8H,9H,10H-cyclonona[b]thiophene-2-carboxamide (Intermediate 45)

The title compound was prepared by the general procedure (scheme 1, step 6, method A) from Intermediate 44 and 2-(methylamino)ethanol (CAS: 109-83-1). The crude product was purified by flash silica gel chromatography using a linear gradient of ethyl acetate in hexane from 30% to 100% (y=75%). Colourless oil.

N-[(1-{[(2-Hydroxyethyl)(methyl)amino]methyl}cyclopentyl)methyl]-4H,5H,6H,7H,8H,9H,10H-cyclonona[b]thiophene-2-carboxamide The title compound was prepared by the general procedure (scheme 1, step 7) from Intermediate 45 and LiAlH$_4$. The crude product was purified by flash silica gel chromatography using a linear gradient of ethyl acetate in hexane from 30% to 100% (y=67%). Colourless oil.

Example 30

N-[(1-{[(2-Hydroxyethyl)(methyl)amino]
methyl}cyclobutyl)methyl]-4H,5H,6H,7H,8H,9H-
cycloocta[b]thiophene-2-carboxamide N-({1-[(2-Hydroxyethyl)(methyl)carbamoyl]
cyclobutyl}methyl)-4H,5H,6H,7H,8H,9H-cycloocta
[b]thiophene-2-carboxamide (Intermediate 46)

The title compound was prepared by the general procedure (scheme 1, step 6, method A) from Intermediate 30 and 2-(methylamino)ethanol (CAS: 109-83-1). The crude product was purified by flash silica gel chromatography using a linear gradient of ethyl acetate in hexane from 30% to 100% (y=80%). Colourless oil.

N-[(1-{[(2-Hydroxyethyl)(methyl)amino]
methyl}cyclobutyl)methyl]-4H,5H,6H,7H,8H,9H-
cycloocta[b]thiophene-2-carboxamide The title compound was prepared by the general procedure (scheme 1, step 7) from Intermediate 46 and LiAlH$_4$. The crude product was purified by flash silica gel chromatography using a linear gradient of ethyl acetate in hexane from 30% to 100% (y=65%). Colourless oil.

Example 31

N-({1-[(Dimethylamino)methyl]-3-
hydroxycyclobutyl}methyl)-4H,5H,6H,7H,8H,9H-
cycloocta[b]thiophene-2-carboxamide Methyl 1-[[(4,5,6,7,8,9-hexahydrocycloocta[b]thio-
phen-2-ylcarbonyl)amino]methyl]-3-hydroxycy-
clobutanecarboxylate (Intermediate 47)

The title compound was prepared by the general procedure (scheme 1, step 4, method B) from 4,5,6,7,8,9-hexahydrocycloocta[b]thiophene-2-carboxylic acid (CAS: 40133-09-3) and methyl 1-(aminomethyl)-3-hydroxycyclobutane-1-carboxylate hydrochloride (CAS: 1955514-52-9). The crude product was purified by flash silica gel chromatography using a linear gradient of methanol in dichloromethane from 0% to 15% (y=98%). White solid.

1-[[(4,5,6,7,8,9-Hexahydrocycloocta[b]thiophen-2-
ylcarbonyl)amino]methyl]-3-hydroxycyclobutan-
ecarboxylic acid (Intermediate 48)

The title compound was prepared by the general procedure (scheme 1, step 5, method A) from Intermediate 47. Y=92%. White solid.

N-{[1-(Dimethylcarbamoyl)-3-hydroxycyclobutyl]
methyl}-4H,5H,6H,7H,8H,9H-cycloocta[b]thio-
phene-2-carboxamide (Intermediate 49)

The title compound was prepared by the general procedure (scheme 1, step 6, method A) from Intermediate 48 and dimethylamine (CAS: 124-40-3). The crude product was purified by silica gel column chromatography using a linear gradient of methanol in dichloromethane from 0% to 5% (y=89%). White solid.

N-({1-[(Dimethylamino)methyl]-3-
hydroxycyclobutyl}methyl)-4H,5H,6H,7H,8H,9H-
cycloocta[b]thiophene-2-carboxamide The title compound was prepared by the general procedure (scheme 1, step 7) from intermediate 49 and LiAlH$_4$. The crude product was purified by flash silica gel chromatography using a linear gradient of ethyl acetate in hexane from 0% to 10% (y=80%). Colorless oil.

Example 32

N-{[3-Hydroxy-1-(pyrrolidin-1-ylmethyl)cy-
clobutyl]methyl}-4H,5H,6H,7H,8H,9H-cycloocta[b]
thiophene-2-carboxamide N-{[3-Hydroxy-1-(pyrrolidine-1-carbonyl)cy-
clobutyl]methyl}-4H,5H,6H,7H,8H,9H-cycloocta[b]
thiophene-2-carboxamide (Intermediate 50)

The title compound was prepared by the general procedure (scheme 1, step 6, method A) from Intermediate 48 and pyrrolidine (CAS: 123-75-1). The crude product was purified by silica gel column chromatography using a linear gradient of methanol in dichloromethane from 0% to 5% (y=80%). White solid.

N-{[3-Hydroxy-1-(pyrrolidin-1-ylmethyl)cy-
clobutyl]methyl}-4H,5H,6H,7H,8H,9H-cycloocta[b]
thiophene-2-carboxamide The title compound was prepared by the general procedure (scheme 1, step 7) from intermediate 50 and LiAlH$_4$. The crude product was purified by flash silica gel chromatography using a linear gradient of ethyl acetate in hexane from 0% to 10% (y=80%). Colorless oil.

Example 33

N-({1-[(Dimethylamino)methyl]
cyclopentyl}methyl)-5,6,7,8,9,10-hexahydrobenzo
[8]annulene-2-carboxamide Methyl 5,6,7,8,9,10-hexahydrobenzo[8]annulene-2-
carboxylate (Intermediate 51)

The title compound was prepared by the general procedure (scheme 3, step 1) from methyl 2-oxo-2H-pyran-5-carboxylate (CAS: 6018-41-3) and cis-cyclooctene (CAS: 931-87-32). The crude product was purified by flash silica gel chromatography using a linear gradient of ethyl acetate in hexane from 0% to 10% (y=5%). Colourless oil.

5,6,7,8,9,10-Hexahydrobenzo[8]annulene-2-carbox-
ylic acid (Intermediate 52)

The title compound was prepared by the general procedure (scheme 3, step 2) from Intermediate 51 and 3N NaOH. The product was obtained pure (y=86%). White solid.

N-({1-[(Dimethylamino)methyl]
cyclopentyl}methyl)-5,6,7,8,9,10-hexahydrobenzo
[8]annulene-2-carboxamide The title compound was prepared by the general procedure (scheme 3, step 3) from Intermediate 52 and HATU at room temperature for 10 min. Then {1-[(dimethylamino)

methyl]cyclopentyl}methanamine (CAS: 1247566-89-7) and TEA were added and the resulting mixture was stirred at room temperature overnight. The crude product was purified by flash silica gel chromatography using a linear gradient of ethyl acetate in hexane from 50% to 100% (y=89%). Colourless oil.

Example 34

N-[(1-{[(2-Hydroxyethyl)(methyl)amino] methyl}cyclopentyl)methyl]-4H,5H,6H,7H,8H,9H-cycloocta[b]thiophene-2-carboxamide N-({1-[(2-Hydroxyethyl)(methyl)carbamoyl] cyclopentyl}methyl)-4H,5H,6H,7H,8H,9H-cycloocta [b]thiophene-2-carboxamide (Intermediate 53)

The title compound was prepared by the general procedure (scheme 1, step 6, method A) from Intermediate 2 and 2-(methylamino)ethanol (CAS: 109-83-1). The crude product was purified by flash silica gel chromatography using a linear gradient of ethyl acetate in hexane from 30% to 100% (y=77%). Colourless oil.

N-[(1-{[(2-Hydroxyethyl)(methyl)amino] methyl}cyclopentyl)methyl]-4H,5H,6H,7H,8H,9H-cycloocta[b]thiophene-2-carboxamide The title compound was prepared by the general procedure (scheme 1, step 7) from Intermediate 53 and LiAlH$_4$. The crude product was purified by flash silica gel chromatography using a linear gradient of ethyl acetate in hexane from 30% to 100% (y=64%). Colourless oil.

Example 35

N-{[4-(Azetidin-1-ylmethyl)oxan-4-yl]methyl}-4H, 5H,6H,7H,8H,9H-cycloocta[b]thiophene-2-carboxamide N-{[4-(Azetidine-1-carbonyl)oxan-4-yl]methyl}-4H, 5H,6H,7H,8H,9H-cycloocta[b]thiophene-2-carboxamide (Intermediate 54)

The title compound was prepared by the general procedure (scheme 1, step 6, method A) from Intermediate 26 and azetidine hydrochloride (CAS: 503-29-7). The crude product was purified by flash silica gel chromatography using a linear gradient of ethyl acetate in hexane from 30% to 100% (y=84%). Colourless oil.

N-{[4-(Azetidin-1-ylmethyl)oxan-4-yl]methyl}-4H, 5H,6H,7H,8H,9H-cycloocta[b]thiophene-2-carboxamide The title compound was prepared by the general procedure (scheme 1, step 7) from Intermediate 54 and LiAlH$_4$. The crude product was purified by flash silica gel chromatography using a linear gradient of ethyl acetate in hexane from 30% to 100% (y=65%). Colourless oil.

Example 36

N-{[1-(Azetidin-1-ylmethyl)cyclobutyl]methyl}-4H, 5H,6H,7H,8H,9H-cycloocta[b]thiophene-2-carboxamide N-{[1-(Azetidine-1-carbonyl)cyclobutyl]methyl}-4H,5H,6H,7H,8H,9H-cycloocta[b]thiophene-2-carboxamide (Intermediate 55)

The title compound was prepared by the general procedure (scheme 1, step 6, method A) from Intermediate 30 and azetidine hydrochloride (CAS: 503-29-7). The crude product was purified by flash silica gel chromatography using a linear gradient of ethyl acetate in hexane from 30% to 100% (y=80%). Colourless oil.

N-{[1-(Azetidin-1-ylmethyl)cyclobutyl]methyl}-4H, 5H,6H,7H,8H,9H-cycloocta[b]thiophene-2-carboxamide The title compound was prepared by the general procedure (scheme 1, step 7) from Intermediate 55 and LiAlH$_4$. The crude product was purified by flash silica gel chromatography using a linear gradient of ethyl acetate in hexane from 30% to 100% (y=65%). Colourless oil.

Example 37

N-({3-[(Dimethylamino)methyl]oxan-3-yl}methyl)-4H,5H,6H,7H,8H,9H-cycloocta[b]thiophene-2-carboxamide tert-Butyl 3-[[(4,5,6,7,8,9-hexahydrocycloocta[b] thiophen-2-ylcarbonyl)amino]methyl]oxane-3-carboxylate (Intermediate 56)

The title compound was prepared by the general procedure (scheme 1, step 4) from 4H,5H,6H,7H,8H,9H-cycloocta[b]thiophene-2-carboxylic acid (CAS: 40133-09-3) and HATU at room temperature for 10 min. Then tert-butyl 3-(aminomethyl)oxane-3-carboxylate (CAS: 2138241-33-3) and TEA were added and the resulting mixture was stirred at room temperature overnight. The crude product was purified by flash silica gel chromatography using a linear gradient of ethyl acetate in hexane from 0% to 50% (y=97%). Yellow oil.

3-{[(4,5,6,7,8,9-Hexahydrocycloocta[b]thiophen-2-ylcarbonyl)amino]methyl}tetrahydro-2H-pyran-3-carboxylic acid (Intermediate 57)

The title compound was prepared by the general procedure (scheme 1, step 5, method B) from Intermediate 56 and CF$_3$COOH (y=99%). White solid.

3-[[(4,5,6,7,8,9-Hexahydrocycloocta[b]thiophen-2-ylcarbonyl)amino]methyl]-N,N-dimethyloxane-3-carboxamide (Intermediate 58)

The title compound was prepared by the general procedure (scheme 1, step 6, method A) from Intermediate 57 and HATU at room temperature for 10 min. Then dimethylamine (2M in THF) (CAS: 124-40-3) and TEA were added and the resulting mixture was stirred at room temperature overnight. The crude product was purified by flash silica gel chromatography using a linear gradient of ethyl acetate in hexane from 0% to 80% (y=99%). Colourless oil.

N-({3-[(Dimethylamino)methyl]oxan-3-yl}methyl)-4H,5H,6H,7H,8H,9H-cycloocta[b]thiophene-2-carboxamide The title compound was prepared by the general procedure (scheme 1, step 7) from intermediate 58 and LiAlH$_4$. The crude product was purified by flash silica gel chromatography using a linear gradient of ethyl acetate in hexane from 20% to 100% (y=42%). Colourless oil.

Example 38

N-({3-[(Dimethylamino)methyl]oxolan-3-yl}methyl)-4H,5H,6H,7H,8H,9H-cycloocta[b]thiophene-2-carboxamide tert-Butyl 3-[[(4,5,6,7,8,9-hexahydrocycloocta[b]thiophen-2-ylcarbonyl)amino]methyl]oxolane-3-carboxylate (Intermediate 59)

The title compound was prepared by the general procedure (scheme 1, step 4, method B) from 4,5,6,7,8,9-hexahydrocycloocta[b]thiophene-2-carboxylic acid (CAS: 40133-09-3) and tert-butyl 3-(aminomethyl)oxolane-3-carboxylate (CAS: 2137778-54-0). The crude product was purified by flash silica gel chromatography using a linear gradient of methanol in dichloromethane from 20% to 60% (y=64%). White solid.

3-[[(4,5,6,7,8,9-Hexahydrocycloocta[b]thiophen-2-ylcarbonyl)amino]methyl]oxolane-3-carboxylic acid (Intermediate 60)

The title compound was prepared by the general procedure (scheme 1, step 5, method B) from Intermediate 59 and $CF_3COOH$ (y=99%). White solid.

3-[[(4,5,6,7,8,9-Hexahydrocycloocta[b]thiophen-2-ylcarbonyl)amino]methyl]-N,N-dimethyloxolane-3-carboxamide (Intermediate 61)

The title compound was prepared by the general procedure (scheme 1, step 6, method A) from Intermediate 60 and dimethylamine (CAS: 124-40-3). The crude product was purified by silica gel column chromatography using a linear gradient of ethyl acetate in hexane from 20% to 60% (y=87%). Yellowish oil.

N-({3-[(Dimethylamino)methyl]oxolan-3-yl}methyl)-4H,5H,6H,7H,8H,9H-cycloocta[b]thiophene-2-carboxamide The title compound was prepared by the general procedure (scheme 1, step 7) from intermediate 61 and $LiAlH_4$. The crude product was purified by flash silica gel chromatography using a linear gradient of methanol in dichloromethane from 0% to 20% (y=60%). Colourless oil.

Example 39

N-{[3-(Pyrrolidin-1-ylmethyl)oxolan-3-yl]methyl}-4H,5H,6H,7H,8H,9H-cycloocta[b]thiophene-2-carboxamide N-{[3-(Pyrrolidine-1-carbonyl)oxolan-3-yl]methyl}-4H,5H,6H,7H,8H,9H-cycloocta[b]thiophene-2-carboxamide (Intermediate 62)

The title compound was prepared by the general procedure (scheme 1, step 6, method A) from Intermediate 60 and pyrrolidine (CAS: 123-75-1). The crude product was purified by silica gel column chromatography using a linear gradient of ethyl acetate in hexane from 20% to 60% (y=78%). Yellowish oil.

N-{[3-(Pyrrolidin-1-ylmethyl)oxolan-3-yl]methyl}-4H,5H,6H,7H,8H,9H-cycloocta[b]thiophene-2-carboxamide The title compound was prepared by the general procedure (scheme 1, step 7) from intermediate 62 and $LiAlH_4$. The crude product was purified by flash silica gel chromatography using a linear gradient of methanol in dichloromethane from 0% to 20% (y=60%). Colourless oil.

Example 40

N-({1-[(4-Hydroxypiperidin-1-yl)methyl]cyclobutyl}methyl)-4H,5H,6H,7H,8H,9H-cycloocta[b]thiophene-2-carboxamide N-{[1-(4-Hydroxypiperidine-1-carbonyl)cyclobutyl]methyl}-4H,5H,6H,7H,8H,9H-cycloocta[b]thiophene-2-carboxamide (Intermediate 63)

The title compound was prepared by the general procedure (scheme 1, step 6, method A) from Intermediate 26 and 4-hydroxypiperidine (CAS: 5382-16-1). The crude product was purified by flash silica gel chromatography using a linear gradient of ethyl acetate in hexane from 30% to 100% (y=78%). Colourless oil.

N-({1-[(4-Hydroxypiperidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 63 and $LiAlH_4$. The crude product was purified by flash silica gel chromatography using a linear gradient of ethyl acetate in hexane from 30% to 100% (y=70%). Colourless oil.

Example 41

N-({1-[(4-Hydroxypiperidin-1-yl)methyl]cyclobutyl}methyl)-4H,5H,6H,7H,8H,9H-cycloocta[b]thiophene-2-carboxamide N-{[1-(4-Hydroxypiperidine-1-carbonyl)cyclobutyl]methyl}-4H,5H,6H,7H,8H,9H-cycloocta[b]thiophene-2-carboxamide (Intermediate 64)

The title compound was prepared by the general procedure (scheme 1, step 6, method A) from Intermediate 30 and 4-hydroxypiperidine (CAS: 5382-16-1). The crude product was purified by flash silica gel chromatography using a linear gradient of ethyl acetate in hexane from 30% to 100% (y=80%). Colourless oil.

N-({1-[(4-Hydroxypiperidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 64 and $LiAlH_4$. The crude product was purified by flash silica gel chromatography using a linear gradient of ethyl acetate in hexane from 30% to 100% (y=63%). Colorless oil.

Example 42

N-{3-[4-(2-Methoxyethoxy)piperidin-1-yl]-2,2-dimethylpropyl}-4H,5H,6H,7H,8H,9H-cycloocta[b]thiophene-2-carboxamide N-{3-[4-(2-Methoxyethoxy)piperidin-1-yl]-2,2-dimethyl-3-oxopropyl}-4H,5H,6H,7H,8H,9H-cycloocta[b]thiophene-2-carboxamide (Intermediate 65)

The title compound was prepared by the general procedure (scheme 1, step 6, method A) from Intermediate 16 and 4-(2-methoxyethoxy)piperidine (CAS: 70978-88-0). The crude product was purified by silica gel column chromatography using a linear gradient of ethyl acetate in hexane from 15% to 70% (y=70%). White solid.

N-{3-[4-(2-Methoxyethoxy)piperidin-1-yl]-2,2-dimethylpropyl}-4H,5H,6H,7H,8H,9H-cycloocta[b]thiophene-2-carboxamide The title compound was prepared by the general procedure (scheme 1, step 7) from intermediate 65 and LiAlH$_4$. The crude product was purified by flash silica gel chromatography using a linear gradient of methanol in dichloromethane from 0% to 20% (y=80%). Colorless oil.

Example 43

N-({3-[(3-Hydroxypyrrolidin-1-yl)methyl]oxan-3-yl}methyl)-4H,5H,6H,7H,8H,9H-cycloocta[b]thiophene-2-carboxamide N-{[3-(3-Hydroxypyrrolidine-1-carbonyl)oxan-3-yl]methyl}-4H,5H,6H,7H,8H,9H-cycloocta[b]thiophene-2-carboxamide (Intermediate 66)

The title compound was prepared by the general procedure (scheme 1, step 6, method A) from Intermediate 57 and HATU at room temperature for 10 min. Then pyrrolidin-3-ol hydrochloride (CAS: 86070-82-8) and TEA were added and the resulting mixture was stirred at room temperature overnight. The crude product was purified by flash silica gel chromatography using a linear gradient of methanol in dichloromethane from 0% to 10% (y=70%). Colourless oil.

N-({3-[(3-Hydroxypyrrolidin-1-yl)methyl]oxan-3-yl}methyl)-4H,5H,6H,7H,8H,9H-cycloocta[b]thiophene-2-carboxamide The title compound was prepared by the general procedure (scheme 1, step 7) from intermediate 66 and LiAlH$_4$. The crude product was purified by flash silica gel chromatography using a linear gradient of methanol in dichloromethane from 0% to 6% (y=13%). Colourless oil.

Example 44

N-{[3-(Pyrrolidin-1-ylmethyl)oxan-3-yl]methyl}-4H,5H,6H,7H,8H,9H-cycloocta[b]thiophene-2-carboxamide N-{[3-(Pyrrolidine-1-carbonyl)oxan-3-yl]methyl}-4H,5H,6H,7H,8H,9H-cycloocta[b]thiophene-2-carboxamide (Intermediate 67)

The title compound was prepared by the general procedure (scheme 1, step 6, method A) from intermediate 57 and HATU at room temperature for 10 min. Then pyrrolidine (CAS: 123-75-1) and TEA were added and the resulting mixture was stirred at room temperature overnight. The crude product was purified by flash silica gel chromatography using a linear gradient of ethyl acetate in hexane from 0% to 100% (y=59%). Colourless oil.

N-{[3-(Pyrrolidin-1-ylmethyl)oxan-3-yl]methyl}-4H,5H,6H,7H,8H,9H-cycloocta[b]thiophene-2-carboxamide The title compound was prepared by the general procedure (scheme 1, step 7) from intermediate 67 and LiAlH$_4$. The crude product was purified by flash silica gel chromatography using a linear gradient of methanol in dichloromethane from 0% to 6% (y=36%). Colourless oil.

Example 45

N-({3-[(3-Hydroxypiperidin-1-yl)methyl]oxan-3-yl}methyl)-4H,5H,6H,7H,8H,9H-cycloocta[b]thiophene-2-carboxamide N-{4H,5H,6H,7H,8H,9H-cycloocta[b]thiophene-2-carbonyl}-3-[(3-hydroxypiperidin-1-yl)methyl]oxane-3-carboxamide (Intermediate 68)

The title compound was prepared by the general procedure (scheme 1, step 6, method A) from intermediate 57 and HATU at room temperature for 10 min. Then 4-hydroxypiperidine (CAS: 5382-16-1) and TEA were added and the resulting mixture was stirred at room temperature overnight. The crude product was purified by flash silica gel chromatography using a linear gradient of methanol in dichloromethane from 0% to 10% (y=64%). White solid.

N-({3-[(3-Hydroxypiperidin-1-yl)methyl]oxan-3-yl}methyl)-4H,5H,6H,7H,8H,9H-cycloocta[b]thiophene-2-carboxamide The title compound was prepared by the general procedure (scheme 1, step 7) from intermediate 68 and LiAlH$_4$. The crude product was purified by flash silica gel chromatography using a linear gradient of methanol in dichloromethane from 0% to 6% (y=35%). Colourless oil.

Example 46

N-[3-(3-Hydroxypiperidin-1-yl)-2,2-dimethylpropyl]-4H,5H,6H,7H,8H,9H-cycloocta[b]thiophene-2-carboxamide N-[3-(3-Hydroxypiperidin-1-yl)-2,2-dimethyl-3-oxopropyl]-4H,5H,6H,7H,8H,9H-cycloocta[b]thiophene-2-carboxamide (Intermediate 69)

The title compound was prepared by the general procedure (scheme 1, step 6, method A) from Intermediate 16 and HATU at room temperature for 10 min. Then piperidin-3-ol (CAS: 6859-99-0) and TEA were added and the resulting mixture was stirred at room temperature overnight. The crude product was purified by flash silica gel chromatography using a linear gradient of methanol in dichloromethane from 0% to 5% (y=87%). Colourless oil.

N-[3-(3-Hydroxypiperidin-1-yl)-2,2-dimethylpropyl]-4H,5H,6H,7H,8H,9H-cycloocta[b]thiophene-2-carboxamide The title compound was prepared by the general procedure (scheme 1, step 7) from intermediate 69 and LiAlH$_4$. The crude product was purified by flash silica gel chromatography using a linear gradient of ethyl acetate in hexane from 20% to 100% (y=22%). Colourless oil.

Example 47

N-[3-(4-Methoxypiperidin-1-yl)-2,2-dimethylpropyl]-4H,5H,6H,7H,8H,9H-cycloocta[b]thiophene-2-carboxamide N-[3-(4-Methoxypiperidin-1-yl)-2,2-dimethyl-3-oxopropyl]-4H,5H,6H,7H,8H,9H-cycloocta[b]thiophene-2-carboxamide (Intermediate 70)

The title compound was prepared by the general procedure (scheme 1, step 6, method A) from Intermediate 16 and HATU at room temperature for 10 min. Then 4-methoxypiperidine hydrochloride (CAS: 4045-25-4) and TEA were added and the resulting mixture was stirred at room temperature overnight. The crude product was purified by flash silica gel chromatography using a linear gradient of methanol in dichloromethane from 0% to 3% (y=98%). Colourless oil.

N-[3-(4-Methoxypiperidin-1-yl)-2,2-dimethylpropyl]-4H,5H,6H,7H,8H,9H-cycloocta[b]thiophene-2-carboxamide The title compound was prepared by the general procedure (scheme 1, step 7) from intermediate 70 and LiAlH$_4$. The crude product was purified by flash silica gel chromatography using a linear gradient of ethyl acetate in hexane from 20% to 100% (y=54%). Colourless oil.

Example 48

N-({1-[(4-Methoxy-4-methylpiperidin-1-yl)methyl]cyclobutyl}methyl)-4H,5H,6H,7H,8H,9H-cycloocta[b]thiophene-2-carboxamide N-{[1-(4-Methoxy-4-methylpiperidine-1-carbonyl)cyclobutyl]methyl}-4H,5H,6H,7H,8H,9H-cycloocta[b]thiophene-2-carboxamide (Intermediate 71)

The title compound was prepared by the general procedure (scheme 1, step 6, method A) from Intermediate 30 and 4-methoxy-4-methylpiperidine (CAS: 3970-72-7). The crude product was purified by flash silica gel chromatography using a linear gradient of ethyl acetate in hexane from 30% to 100% (y=75%). Colourless oil.

N-({1-[(4-Methoxy-4-methylpiperidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 71 and LiAlH$_4$. The crude product was purified by flash silica gel chromatography using a linear gradient of ethyl acetate in hexane from 30% to 100% (y=68%). Colourless oil.

Example 49

N-({1-[(4-Methoxypiperidin-1-yl)methyl]cyclobutyl}methyl)-4H,5H,6H,7H,8H,9H-cycloocta[b]thiophene-2-carboxamide N-{[1-(4-Methoxypiperidine-1-carbonyl)cyclobutyl]methyl}-4H,5H,6H,7H,8H,9H-cycloocta[b]thiophene-2-carboxamide (Intermediate 72)

The title compound was prepared by the general procedure (scheme 1, step 6, method A) from Intermediate 30 and HATU at room temperature for 10 min. Then 4-methoxypiperidine hydrochloride (CAS: 4045-25-4) and TEA were added and the resulting mixture was stirred at room temperature overnight. The crude product was purified by flash silica gel chromatography using a linear gradient of ethyl acetate in hexane from 0% to 80% (y=96%). White solid.

N-({1-[(4-Methoxypiperidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 72 and LiAlH$_4$. The crude product was purified by flash silica gel chromatography using a linear gradient of ethyl acetate in hexane from 0% to 80% (y=34%). Colourless oil.

Example 50

N-[(1-{[3-(Propan-2-yloxy)piperidin-1-yl]methyl}cyclobutyl)methyl]-4H,5H,6H,7H,8H,9H-cycloocta[b]thiophene-2-carboxamide N-({1-[4-(Propan-2-yloxy)piperidine-1-carbonyl]cyclobutyl}methyl)-4H,5H,6H,7H,8H,9H-cycloocta[b]thiophene-2-carboxamide (Intermediate 73)

The title compound was prepared by the general procedure (scheme 1, step 6, method A) from intermediate 30 and HATU at room temperature for 10 min. Then 3-(propan-2-yloxy)piperidine (CAS: 1220175-72-3) and TEA were added and the resulting mixture was stirred at room temperature overnight. The crude product was purified by flash silica gel chromatography using a linear gradient of ethyl acetate in hexane from 0% to 80% (y=93%). White solid.

N-[(1-{[3-(Propan-2-yloxy)piperidin-1-yl]methyl}cyclobutyl)methyl]-4H,5H,6H,7H,8H,9H-cycloocta[b]thiophene-2-carboxamide The title compound was prepared by the general procedure (scheme 1, step 7) from intermediate 73 and LiAlH$_4$. The crude product was purified by flash silica gel chromatography using a linear gradient of ethyl acetate in hexane from 0% to 80% (y=55%). Colourless oil.

Example 51

N-[(1-{[4-(Propan-2-yloxy)piperidin-1-yl]methyl}cyclobutyl)methyl]-4H,5H,6H,7H,8H,9H-cycloocta[b]thiophene-2-carboxamide N-({1-[4-(Propan-2-yloxy)piperidine-1-carbonyl]cyclobutyl}methyl)-4H,5H,6H,7H,8H,9H-cycloocta[b]thiophene-2-carboxamide (Intermediate 74)

The title compound was prepared by the general procedure (scheme 1, step 6, method A) from Intermediate 30 and HATU at room temperature for 10 min. Then 4-(propan-2-yloxy)piperidine (CAS: 43139-18-0) and TEA were added and the resulting mixture was stirred at room temperature overnight. The crude product was purified by flash silica gel chromatography using a linear gradient of ethyl acetate in hexane from 0% to 80% (y=78%). White solid.

N-[(1-{[4-(Propan-2-yloxy)piperidin-1-yl]methyl}cyclobutyl)methyl]-4H,5H,6H,7H,8H,9H-cycloocta[b]thiophene-2-carboxamide The title compound was prepared by the general procedure (scheme 1, step 7) from Intermediate 74 and LiAlH$_4$. The crude product was purified by flash silica gel chromatography using a linear gradient of methanol in dichloromethane from 0% to 20% (y=81%). Colourless oil.

Example 52

N-({1-[(3-Hydroxy-3-methylpiperidin-1-yl)methyl]cyclopentyl}methyl)-4H,5H,6H,7H,8H,9H-cycloocta[b]thiophene-2-carboxamide N-{[1-(3-Hydroxy-3-methylpiperidine-1-carbonyl)cyclopentyl]methyl}-4H,5H,6H,7H,8H,9H-cycloocta[b]thiophene-2-carboxamide (Intermediate 75)

The title compound was prepared by the general procedure (scheme 1, step 6, method A) from Intermediate 2 and 3-methylpiperidin-3-ol (CAS: 473730-88-0). The crude product was purified by flash silica gel chromatography using a linear gradient of ethyl acetate in hexane from 30% to 100% (y=82%). Colourless oil.

N-({1-[(3-Hydroxy-3-methylpiperidin-1-yl)methyl]cyclopentyl}methyl)-4H,5H,6H,7H,8H,9H-cycloocta[b]thiophene-2-carboxamide The title compound was prepared by the general procedure (scheme 1, step 7) from Intermediate 75 and LiAlH$_4$. The crude product was purified by flash silica gel chromatography using a linear gradient of ethyl acetate in hexane from 30% to 100% (y=65%). Colourless oil.

Example 53

N-({1-[(4-Methoxy-4-methylpiperidin-1-yl)methyl]cyclopentyl}methyl)-4H,5H,6H,7H,8H,9H-cycloocta[b]thiophene-2-carboxamide N-{[1-(4-hydroxy-4-methylpiperidine-1-carbonyl)cyclopentyl]methyl}-4H,5H,6H,7H,8H,9H-cycloocta[b]thiophene-2-carboxamide (Intermediate 76)

The title compound was prepared by the general procedure (scheme 1, step 6, method A) from Intermediate 2 and 4-methoxy-4-methylpiperidine (CAS: 3970-72-7). The crude product was purified by flash silica gel chromatography using a linear gradient of ethyl acetate in hexane from 30% to 100% (y=81%). Colourless oil.

N-({1-[(4-Methoxy-4-methylpiperidin-1-yl)methyl]cyclopentyl}methyl)-4H,5H,6H,7H,8H,9H-cycloocta[b]thiophene-2-carboxamide The title compound was prepared by the general procedure (scheme 1, step 7) from Intermediate 76 and LiAlH$_4$. The crude product was purified by flash silica gel chromatography using a linear gradient of ethyl acetate in hexane from 30% to 100% (y=61%). Colourless oil.

Example 54

N-[3-(3-Methoxypiperidin-1-yl)-2,2-dimethylpropyl]-4H,5H,6H,7H,8H,9H-cycloocta[b]thiophene-2-carboxamide N-[3-(3-Methoxypiperidin-1-yl)-2,2-dimethyl-3-oxopropyl]-4H,5H,6H,7H,8H,9H-cycloocta[b]thiophene-2-carboxamide (Intermediate 77)

The title compound was prepared by the general procedure (scheme 1, step 6, method A) from Intermediate 16 and 3-methoxypiperidine (CAS: 4045-29-8). The crude product was purified by flash silica gel chromatography using a linear gradient of ethyl acetate in hexane from 30% to 100% (y=80%). Colourless oil.

N-[3-(3-Methoxypiperidin-1-yl)-2,2-dimethylpropyl]-4H,5H,6H,7H,8H,9H-cycloocta[b]thiophene-2-carboxamide The title compound was prepared by the general procedure (scheme 1, step 7) from Intermediate 77 and LiAlH$_4$. The crude product was purified by flash silica gel chromatography using a linear gradient of ethyl acetate in hexane from 30% to 100% (y=55%). Colourless oil.

Example 55

N-({1-[(3-Methoxypiperidin-1-yl)methyl]cyclobutyl}methyl)-4H,5H,6H,7H,8H,9H-cycloocta[b]thiophene-2-carboxamide N-{[1-(3-Methoxypiperidine-1-carbonyl)cyclobutyl]methyl}-4H,5H,6H,7H,8H,9H-cycloocta[b]thiophene-2-carboxamide (Intermediate 78)

The title compound was prepared by the general procedure (scheme 1, step 6, method A) from Intermediate 30 and 3-methoxypiperidine (CAS: 4045-29-8). The crude product was purified by flash silica gel chromatography using a linear gradient of ethyl acetate in hexane from 30% to 100% (y=81%). Colourless oil.

N-({1-[(3-Methoxypiperidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 78 and LiAlH$_4$. The crude product was purified by flash silica gel chromatography using a linear gradient of ethyl acetate in hexane from 30% to 100% (y=71%). Colourless oil.

Example 56

N-({1-[(Dimethylamino)methyl]-3,3-difluorocyclobutyl}methyl)-4H,5H,6H,7H,8H,9H-cycloocta[b]thiophene-2-carboxamide Methyl 1-(aminomethyl)-3,3-difluorocyclobutanecarboxylate hydrochloride (Intermediate 79)

Thionyl chloride was added to a 0° C. cooled solution of amino acid in methanol. The reaction was heated to reflux temperature and stirred for 3 h. After cooling, the mixture was evaporated and the residue was used for the next step without further purification.

Methyl 3,3-difluoro-1-{[(4,5,6,7,8,9-hexahydrocycloocta[b]thiophen-2-ylcarbonyl)amino]methyl} cyclobutanecarboxylate (Intermediate 80)

The title compound was prepared by the general procedure (scheme 1, step 4, method B) from 4,5,6,7,8,9-hexahydrocycloocta[b]thiophene-2-carboxylic acid (CAS: 40133-09-3) and Intermediate 79. The crude product was purified by flash silica gel chromatography using a linear gradient of ethyl acetate in hexane from 5% to 70% (y=87%). White solid.

3,3-Difluoro-1-{[(4,5,6,7,8,9-hexahydrocycloocta[b]thiophen-2-ylcarbonyl)amino]methyl} cyclobutanecarboxylic acid (Intermediate 81)

The title compound was prepared by the general procedure (scheme 1, step 5, method A) from Intermediate 80. Y=96%. White solid.

N-{[3,3-Difluoro-1-(pyrrolidine-1-carbonyl)cyclobutyl]methyl}-4H,5H,6H,7H,8H,9H-cycloocta[b]thiophene-2-carboxamide (Intermediate 82)

The title compound was prepared by the general procedure (scheme 1, step 6, method A) from Intermediate 81 and HATU at room temperature for 10 min. Then dimethylamine (CAS: 124-40-3) and TEA were added and the resulting mixture was stirred at room temperature overnight. The crude product was purified by flash silica gel chromatography using a linear gradient of ethyl acetate in hexane from 5% to 70% (y=68%). White solid.

N-({1-[(Dimethylamino)methyl]-3,3-difluorocyclobutyl}methyl)-4H,5H,6H,7H,8H,9H-cycloocta[b]thiophene-2-carboxamide The title compound was prepared by the general procedure (scheme 1, step 7) from Intermediate 82 and LiAlH$_4$. The crude product was purified by flash silica gel chromatography using a linear gradient of ethyl acetate in hexane from 50% to 100% (y=33%). Colorless oil.

Example 57

N-{[3,3-Difluoro-1-(pyrrolidin-1-ylmethyl)cyclobutyl]methyl}-4H,5H,6H,7H,8H,9H-cycloocta[b]thiophene-2-carboxamide N-{[3,3-Difluoro-1-(pyrrolidine-1-carbonyl)cyclobutyl]methyl}-4H,5H,6H,7H,8H,9H-cycloocta[b]thiophene-2-carboxamide (Intermediate 83)

The title compound was prepared by the general procedure (scheme 1, step 6, method A) from Intermediate 81 and HATU at room temperature for 10 min. Then pyrrolidine (CAS: 123-75-1) and TEA were added and the resulting mixture was stirred at room temperature overnight. The crude product was purified by flash silica gel chromatography using a linear gradient of ethyl acetate in hexane from 5% to 70% (y=68%). White solid.

N-{[3,3-Difluoro-1-(pyrrolidin-1-ylmethyl)cyclobutyl]methyl}-4H,5H,6H,7H,8H,9H-cycloocta[b]thiophene-2-carboxamide The title compound was prepared by the general procedure (scheme 1, step 7) from Intermediate 83 and LiAlH$_4$. The crude product was purified by flash silica gel chromatography using a linear gradient of ethyl acetate in hexane from 50% to 100% (y=38%). Colorless Example 58

N-({1-[(4-Hydroxy-3,3-dimethylpiperidin-1-yl)methyl]cyclobutyl}methyl)-4H,5H,6H,7H,8H,9H-cycloocta[b]thiophene-2-carboxamide N-{[1-(4-Hydroxy-3,3-dimethylpiperidine-1-carbonyl)cyclobutyl]methyl}-4H,5H,6H,7H,8H,9H-cycloocta[b]thiophene-2-carboxamide (Intermediate 84)

The title compound was prepared by the general procedure (scheme 1, step 6, method A) from Intermediate 30 and 3,3-dimethylpiperidin-4-ol (CAS: 373603-88-4). The crude product was purified by flash silica gel chromatography using a linear gradient of ethyl acetate in hexane from 30% to 100% (y=81%). Colourless oil.

N-({1-[(4-Hydroxy-3,3-dimethylpiperidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 84 and LiAlH$_4$. The crude product was purified by flash silica gel chromatography using a linear gradient of ethyl acetate in hexane from 30% to 100% (y=62%). Colourless oil.

Example 59

N-({1-[(3-Hydroxy-3-methylpiperidin-1-yl)methyl]cyclobutyl}methyl)-4H,5H,6H,7H,8H,9H-cycloocta[b]thiophene-2-carboxamide N-{[1-(3-Hydroxy-3-methylpiperidine-1-carbonyl)cyclobutyl]methyl}-4H,5H,6H,7H,8H,9H-cycloocta[b]thiophene-2-carboxamide (Intermediate 85)

The title compound was prepared by the general procedure (scheme 1, step 6, method A) from Intermediate 30 and 3-methylpiperidin-3-ol (CAS: 473730-88-0). The crude product was purified by flash silica gel chromatography using a linear gradient of ethyl acetate in hexane from 30% to 100% (y=65%). Colourless oil.

N-({1-[(3-Hydroxy-3-methylpiperidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 85 and LiAlH$_4$. The crude product was purified by flash silica gel chroma-

Examples 60 and 61

N-({1-[(Dimethylamino)methyl]-2-methylcyclopentyl}methyl)-4H,5H,6H,7H,8H,9H-cycloocta[b]thiophene-2-carboxamide Ethyl 1-[[(4,5,6,7,8,9-hexahydrocycloocta[b]thiophen-2-ylcarbonyl)amino]methyl]-2-methylcyclopentanecarboxylate (Intermediate 86)

The title compound was prepared by the general procedure (scheme 1, step 4) from 4H,5H,6H,7H,8H,9H-cycloocta[b]thiophene-2-carboxylic acid (CAS: 40133-09-3) and HATU at room temperature for 10 min. Then ethyl 1-(aminomethyl)-2-methylcyclopentanecarboxylate (CAS: 1500317-16-7) and TEA were added and the resulting mixture was stirred at room temperature overnight. The crude product was purified by flash silica gel chromatography using a linear gradient of ethyl acetate in from 0% to 20% (y=96%). Colourless oil.

1-[[(4,5,6,7,8,9-Hexahydrocycloocta[b]thiophen-2-ylcarbonyl)amino]methyl]-2-methylcyclopentanecarboxylic acid (Intermediate 87)

The title compound was prepared by the general procedure (scheme 1, step 5, method A) from Intermediate 86 and 3N NaOH in EtOH (y=88%). White solid.

N-{[1-(Dimethylcarbamoyl)-2-methylcyclopentyl]methyl}-4H,5H,6H,7H,8H,9H-cycloocta[b]thiophene-2-carboxamide (Intermediate 88)

The title compound was prepared by the general procedure (scheme 1, step 6, method A) from intermediate 87 and HATU at room temperature for 10 min. Then dimethylamine (2M in THF) (CAS: 124-40-3) and TEA were added and the resulting mixture was stirred at room temperature overnight. The crude product was purified by flash silica gel chromatography using a linear gradient of ethyl acetate in hexane from 0% to 50% (y=77%). Colourless oil.

N-({1-[(Dimethylamino)methyl]-2-methylcyclopentyl}methyl)-4H,5H,6H,7H,8H,9H-cycloocta[b]thiophene-2-carboxamide The title compound was prepared by the general procedure (scheme 1, step 7) from intermediate 88 and LiAlH$_4$. The crude product was purified by flash silica gel chromatography using a linear gradient of ethyl acetate in hexane from 20% to 80%. The crude product was purified by flash silica gel chromatography (Biotage Isolera-SNAP 10 g) eluting with 20% to 80% EtOAc/Hexane to obtain the two diasteroisomers:

Example 60 (Fraction 1) and Example 61 (Fraction 2) were purified by HPLC using a linear gradient of acetonitrile in water from 10% to 90%. White solid.

Example 62

N-{[2-Methyl-1-(pyrrolidin-1-ylmethyl)cyclopentyl]methyl}-4H,5H,6H,7H,8H,9H-cycloocta[b]thiophene-2-carboxamide N-{[2-Methyl-1-(pyrrolidine-1-carbonyl)cyclopentyl]methyl}-4H,5H,6H,7H,8H,9H-cycloocta[b]thiophene-2-carboxamide (Intermediate 89)

The title compound was prepared by the general procedure (scheme 1, step 6, method A) from Intermediate 87 and HATU at room temperature for 10 min. Then pyrrolidine (CAS: 123-75-1) and TEA were added and the resulting mixture was stirred at room temperature overnight. The crude product was purified by flash silica gel chromatography using a linear gradient of ethyl acetate in hexane from 0% to 50% (y=59%). White solid.

N-{[2-Methyl-1-(pyrrolidin-1-ylmethyl)cyclopentyl]methyl}-4H,5H,6H,7H,8H,9H-cycloocta[b]thiophene-2-carboxamide The title compound was prepared by the general procedure (scheme 1, step 7) from Intermediate 89 and LiAlH$_4$. The crude product was purified by HPLC using a linear gradient of acetonitrile in water from 10% to 90% (y=16%). Colourless oil.

Example 63 And Example 64

N-[[1-[(3-hydroxypyrrolidin-1-yl)methyl]cyclopentyl]methyl]-4,5,6,7,8,9-hexahydrocycloocta[b]thiophene-2-carboxamide Example 25 was purified by HPLC using Lux® 5 μm Amylose-1 column and a mixture of hexane-ethanol (70:30) as eluant.

Example 63: 1$^{st}$ fraction.
Example 64: 2$^{nd}$ fraction.

Example 65

N-({1-[(3-hydroxypiperidin-1-yl)methyl]cyclobutyl}methyl)-4H,5H,6H,7H,8H,9H-cycloocta[b]thiophene-2-carboxamide N-{[1-(3-Hydroxypiperidine-1-carbonyl)cyclobutyl]methyl}-4H,5H,6H,7H,8H,9H-cycloocta[b]thiophene-2-carboxamide (Intermediate 90)

The title compound was prepared by the general procedure (scheme 1, step 6, method A) from Intermediate 30 and piperidin-3-ol (CAS: 6859-99-0). The crude product was purified by flash silica gel chromatography using a linear gradient of ethyl acetate in hexane from 30% to 100% (y=81%). Colourless oil.

N-({1-[(3-hydroxypiperidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 90 and LiAlH$_4$. The crude product was purified by flash silica gel chromatography using a linear gradient of ethyl acetate in hexane from 30% to 100% (y=58%). Colourless oil.

Example 66

N-({1-[(3-Hydroxypyrrolidin-1-yl)methyl]cyclobutyl}methyl)-4H,5H,6H,7H,8H,9H-cycloocta[b]thiophene-2-carboxamide N-{[1-(3-Hydroxypyrrolidine-1-carbonyl)cyclobutyl]methyl}-4H,5H,6H,7H,8H,9H-cycloocta[b]thiophene-2-carboxamide (Intermediate 91)

The title compound was prepared by the general procedure (scheme 1, step 6, method A) from Intermediate 30 and pyrrolidin-3-ol (CAS: 40499-83-0). The crude product was purified by flash silica gel chromatography using a linear gradient of ethyl acetate in hexane from 30% to 100% (y=71%). Colourless oil.

N-({1-[(3-Hydroxypyrrolidin-1-yl)methyl]cyclobutyl}methyl)-4H,5H,6H,7H,8H,9H-cycloocta[b]thiophene-2-carboxamide The title compound was prepared by the general procedure (scheme 1, step 7) from Intermediate 91 and LiAlH₄. The crude product was purified by flash silica gel chromatography using a linear gradient of ethyl acetate in hexane from 30% to 100% (y=63%). Colourless oil.

Example 67

N-[3-(4-Hydroxy-4-methylpiperidin-1-yl)-2,2-dimethylpropyl]-4H,5H,6H,7H,8H,9H-cycloocta[b]thiophene-2-carboxamide N-[3-(4-Hydroxy-4-methylpiperidin-1-yl)-2,2-dimethyl-3-oxopropyl]-4H,5H,6H,7H,8H,9H-cycloocta[b]thiophene-2-carboxamide (Intermediate 92)

The title compound was prepared by the general procedure (scheme 1, step 6, method A) from Intermediate 16 and 4-methylpiperidin-4-ol (CAS: 3970-68-1). The crude product was purified by flash silica gel chromatography using a linear gradient of ethyl acetate in hexane from 30% to 100% (y=80%). Colourless oil.

N-[3-(4-Hydroxy-4-methylpiperidin-1-yl)-2,2-dimethylpropyl]-4H,5H,6H,7H,8H,9H-cycloocta[b]thiophene-2-carboxamide The title compound was prepared by the general procedure (scheme 1, step 7) from Intermediate 92 and LiAlH₄. The crude product was purified by flash silica gel chromatography using a linear gradient of ethyl acetate in hexane from 30% to 100% (y=55%). Colourless oil.

Example 68

N-[3-(4-Hydroxy-3,3-dimethylpiperidin-1-yl)-2,2-dimethylpropyl]-4H,5H,6H,7H,8H,9H-cycloocta[b]thiophene-2-carboxamide N-[3-(4-Hydroxy-3,3-dimethylpiperidin-1-yl)-2,2-dimethyl-3-oxopropyl]-4H,5H,6H,7H,8H,9H-cycloocta[b]thiophene-2-carboxamide (Intermediate 93)

The title compound was prepared by the general procedure (scheme 1, step 6, method A) from Intermediate 16 and 3,3-dimethylpiperidin-4-ol (CAS: 373603-88-4). The crude product was purified by flash silica gel chromatography using a linear gradient of ethyl acetate in hexane from 30% to 100% (y=76%). Colourless oil.

N-[3-(4-Hydroxy-3,3-dimethylpiperidin-1-yl)-2,2-dimethylpropyl]-4H,5H,6H,7H,8H,9H-cycloocta[b]thiophene-2-carboxamide The title compound was prepared by the general procedure (scheme 1, step 7) from Intermediate 93 and LiAlH₄. The crude product was purified by flash silica gel chromatography using a linear gradient of ethyl acetate in hexane from 30% to 100% (y=67%). Colourless oil.

Example 69

N-({1-[(3aS,6aS)-Hexahydro-2H-furo[2,3-c]pyrrol-5-ylmethyl]cyclopentyl}methyl)-4H,5H,6H,7H,8H,9H-cycloocta[b]thiophene-2-carboxamide N-({1-[(3aS,6aS)-Hexahydro-2H-furo[2,3-c]pyrrole-5-carbonyl]cyclopentyl}methyl)-4H,5H,6H,7H,8H,9H-cycloocta[b]thiophene-2-carboxamide (Intermediate 94)

The title compound was prepared by the general procedure (scheme 1, step 6, method B) from Intermediate 2 and 3,3-dimethylpiperidin-4-ol (CAS: 373603-88-4). The crude product was purified by flash silica gel chromatography using a linear gradient of ethyl acetate in hexane from 10% to 50% (y=71%). Colourless oil.

N-({1-[(3aS,6aS)-Hexahydro-2H-furo[2,3-c]pyrrol-5-ylmethyl]cyclopentyl}methyl)-4H,5H,6H,7H,8H,9H-cycloocta[b]thiophene-2-carboxamide The title compound was prepared by the general procedure (scheme 1, step 7) from Intermediate 94 and LiAlH₄. The crude product was purified by flash silica gel chromatography using a linear gradient of methanol in dichloromethane from 0% to 20% (y=63%). Colourless oil.

Structures of the exemplified compounds are reported in Table 2

TABLE 2

| Ex. | Structure | Chemical Name |
|---|---|---|
| 1 | 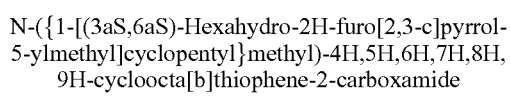 | N-(2,2-dimethyl-3-pyrrolidin-1-ylpropyl)-4,5,6,7,8,9-hexahydrocycloocta[b]thiophene-2-carboxamide |

TABLE 2-continued

| Ex. | Structure | Chemical Name |
|---|---|---|
| 2 | 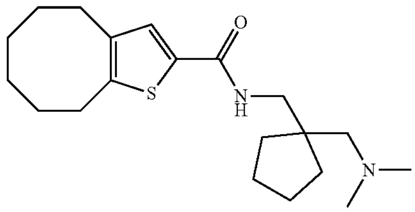 [SMILES: CN(C)CC1(CNC(=O)c2cc3c(s2)CCCCCC3)CCCC1] | N-[[1-[(dimethylamino)methyl]cyclopentyl]methyl]-4,5,6,7,8,9-hexahydrocycloocta[b]thiophene-2-carboxamide |
| 3 | 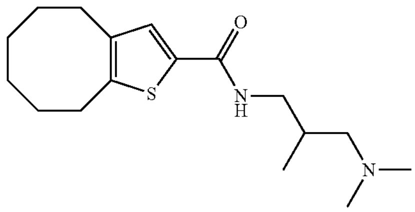 [SMILES: CC(CNC(=O)c1cc2c(s1)CCCCCC2)CN(C)C] | N-[3-(dimethylamino)-2-methylpropyl]-4,5,6,7,8,9-hexahydrocycloocta[b]thiophene-2-carboxamide |
| 4 | 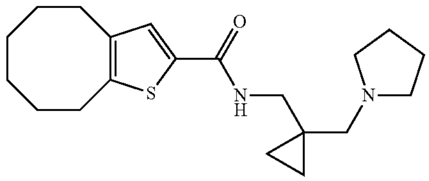 [SMILES: O=C(NCC1(CN2CCCC2)CC1)c1cc2c(s1)CCCCCC2] | N-[[1-(pyrrolidin-1-ylmethyl)cyclopropyl]methyl]-4,5,6,7,8,9-hexahydrocycloocta[b]thiophene-2-carboxamide |
| 5 | 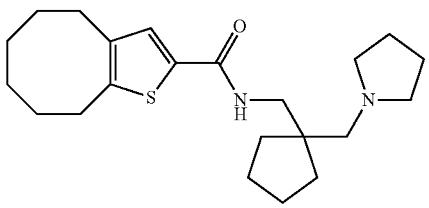 [SMILES: O=C(NCC1(CN2CCCC2)CCCC1)c1cc2c(s1)CCCCCC2] | N-[[1-(pyrrolidin-1-ylmethyl)cyclopentyl]methyl]-4,5,6,7,8,9-hexahydrocycloocta[b]thiophene-2-carboxamide |
| 6 | 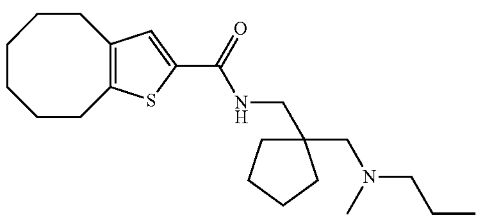 [SMILES: CCCN(C)CC1(CNC(=O)c2cc3c(s2)CCCCCC3)CCCC1] | N-[[1-[[methyl(propyl)amino]methyl]cyclopentyl]methyl]-4,5,6,7,8,9-hexahydrocycloocta[b]thiophene-2-carboxamide |
| 7 | 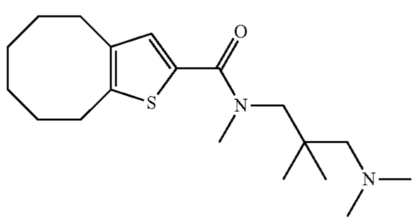 [SMILES: CN(C)CC(C)(C)CN(C)C(=O)c1cc2c(s1)CCCCCC2] | N-[3-(dimethylamino)-2,2-dimethylpropyl]-N-methyl-4,5,6,7,8,9-hexahydrocycloocta[b]thiophene-2-carboxamide |
| 8 | 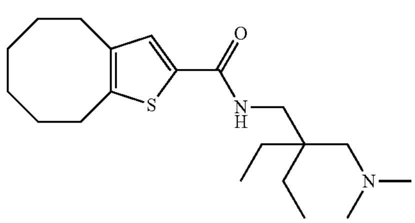 [SMILES: CCC(CC)(CNC(=O)c1cc2c(s1)CCCCCC2)CN(C)C] | N-[2-[(dimethylamino)methyl]-2-ethylbutyl]-4,5,6,7,8,9-hexahydrocycloocta[b]thiophene-2-carboxamide |

TABLE 2-continued

| Ex. | Structure | Chemical Name |
|---|---|---|
| 9 | 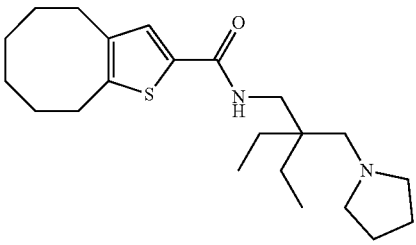 [SMILES: CCC(CC)(CNC(=O)c1cc2c(s1)CCCCCC2)CN1CCCC1] | N-[2-ethyl-2-(pyrrolidin-1-ylmethyl)butyl]-4,5,6,7,8,9-hexahydrocycloocta[b]thiophene-2-carboxamide |
| 10 | 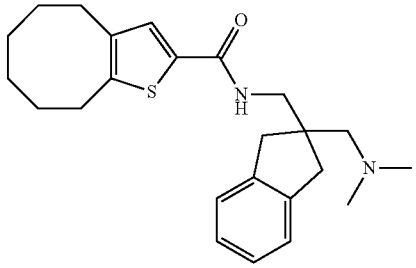 [SMILES: CN(C)CC1(CNC(=O)c2cc3c(s2)CCCCCC3)Cc2ccccc2C1] | N-[[2-[(dimethylamino)methyl]-1,3-dihydroinden-2-yl]methyl]-4,5,6,7,8,9-hexahydrocycloocta[b]thiophene-2-carboxamide |
| 11 | 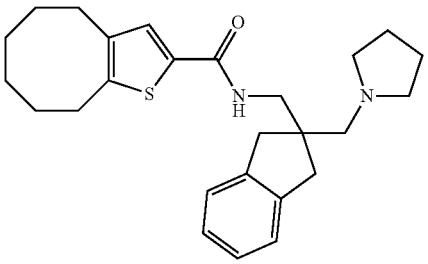 [SMILES: O=C(NCC1(CN2CCCC2)Cc2ccccc2C1)c1cc2c(s1)CCCCCC2] | N-[[2-(pyrrolidin-1-ylmethyl)-1,3-dihydroinden-2-yl]methyl]-4,5,6,7,8,9-hexahydrocycloocta[b]thiophene-2-carboxamide |
| 12 | 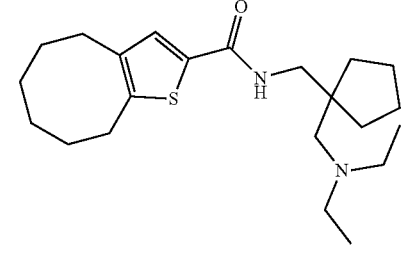 [SMILES: CCN(CC)CC1(CNC(=O)c2cc3c(s2)CCCCCC3)CCCC1] | N-[[1-(diethylaminomethyl)cyclopentyl]methyl]-4,5,6,7,8,9-hexahydrocycloocta[b]thiophene-2-carboxamide |
| 13 | 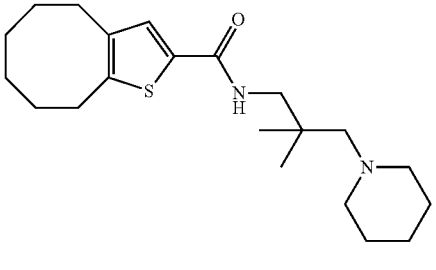 [SMILES: CC(C)(CNC(=O)c1cc2c(s1)CCCCCC2)CN1CCCCC1] | N-(2,2-dimethyl-3-piperidin-1-ylpropyl)-4,5,6,7,8,9-hexahydrocycloocta[b]thiophene-2-carboxamide |
| 14 | 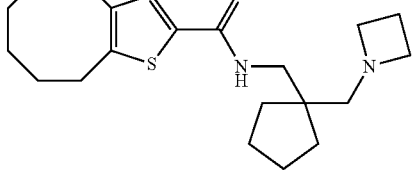 | N-[[1-(azetidin-1-ylmethyl)cyclopentyl]methyl]-4,5,6,7,8,9-hexahydrocycloocta[b]thiophene-2-carboxamide |

TABLE 2-continued

| Ex. | Structure | Chemical Name |
|---|---|---|
| 15 | 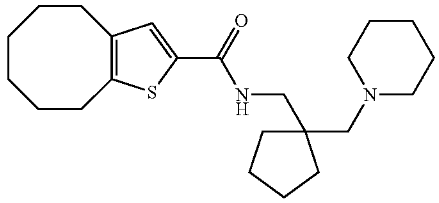 [SMILES: O=C(NCC1(CN2CCCCC2)CCCC1)c1cc2c(s1)CCCCCC2] | N-[[1-(piperidin-1-ylmethyl)cyclopentyl]methyl]-4,5,6,7,8,9-hexahydrocycloocta[b]thiophene-2-carboxamide |
| 16 | 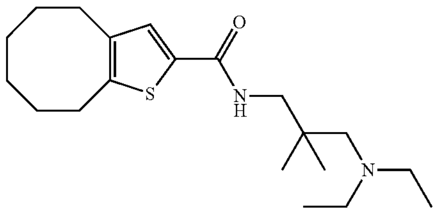 [SMILES: CCN(CC)CC(C)(C)CNC(=O)c1cc2c(s1)CCCCCC2] | N-[3-(diethylamino)-2,2-dimethylpropyl]-4,5,6,7,8,9-hexahydrocycloocta[b]thiophene-2-carboxamide |
| 17 | 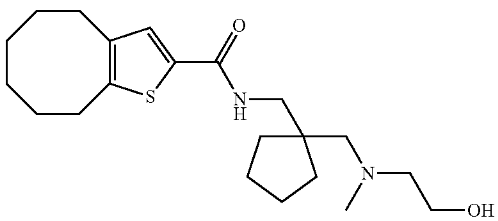 [SMILES: CN(CCO)CC1(CNC(=O)c2cc3c(s2)CCCCCC3)CCCC1] | N-[[1-[[2-hydroxyethyl(methyl)amino]methyl]cyclopentyl]methyl]-4,5,6,7,8,9-hexahydrocycloocta[b]thiophene-2-carboxamide |
| 18 | 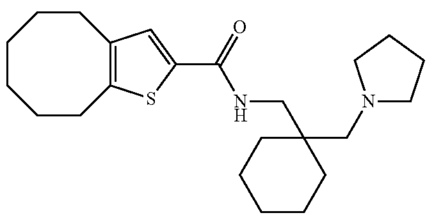 [SMILES: O=C(NCC1(CN2CCCC2)CCCCC1)c1cc2c(s1)CCCCCC2] | N-[[1-(pyrrolidin-1-ylmethyl)cyclohexyl]methyl]-4,5,6,7,8,9-hexahydrocycloocta[b]thiophene-2-carboxamide |
| 19 | 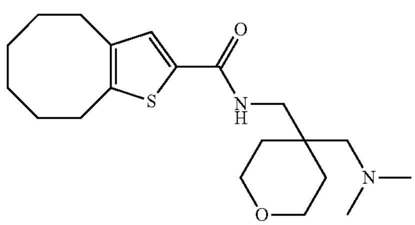 [SMILES: CN(C)CC1(CNC(=O)c2cc3c(s2)CCCCCC3)CCOCC1] | N-[[4-[(dimethylamino)methyl]oxan-4-yl]methyl]-4,5,6,7,8,9-hexahydrocycloocta[b]thiophene-2-carboxamide |
| 20 | 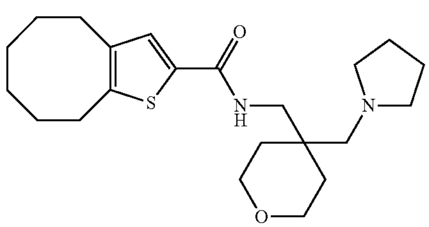 [SMILES: O=C(NCC1(CN2CCCC2)CCOCC1)c1cc2c(s1)CCCCCC2] | N-[[4-(pyrrolidin-1-ylmethyl)oxan-4-yl]methyl]-4,5,6,7,8,9-hexahydrocycloocta[b]thiophene-2-carboxamide |
| 21 | 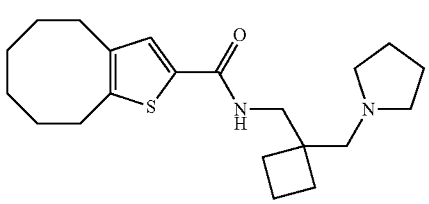 [SMILES: O=C(NCC1(CN2CCCC2)CCC1)c1cc2c(s1)CCCCCC2] | N-[[1-(pyrrolidin-1-ylmethyl)cyclobutyl]methyl]-4,5,6,7,8,9-hexahydrocycloocta[b]thiophene-2-carboxamide |

TABLE 2-continued

| Ex. | Structure | Chemical Name |
|---|---|---|
| 22 | 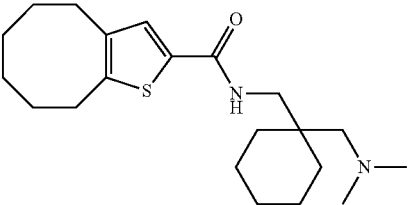 [SMILES: CN(C)CC1(CNC(=O)c2cc3c(s2)CCCCCC3)CCCCC1] | N-[[1-[(dimethylamino)methyl]cyclohexyl]methyl]-4,5,6,7,8,9-hexahydrocycloocta[b]thiophene-2-carboxamide |
| 23 | 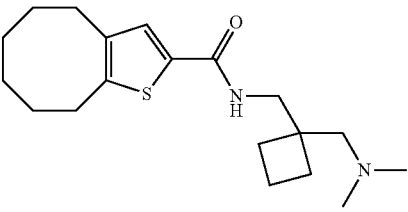 [SMILES: CN(C)CC1(CNC(=O)c2cc3c(s2)CCCCCC3)CCC1] | N-[[1-[(dimethylamino)methyl]cyclobutyl]methyl]-4,5,6,7,8,9-hexahydrocycloocta[b]thiophene-2-carboxamide |
| 24 | 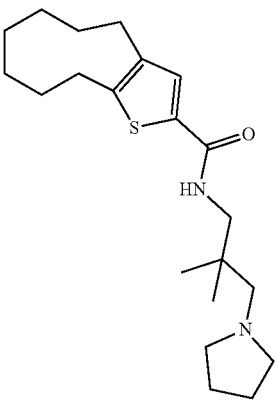 [SMILES: CC(C)(CNC(=O)c1cc2c(s1)CCCCCCC2)CN1CCCC1] | N-(2,2-dimethyl-3-pyrrolidin-1-ylpropyl)-5,6,7,8,9,10-hexahydro-4H-cyclonona[b]thiophene-2-carboxamide |
| 25 | 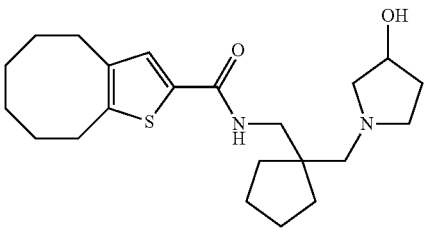 | N-[[1-[(3-hydroxypyrrolidin-1-yl)methyl]cyclopentyl]methyl]-4,5,6,7,8,9-hexahydrocycloocta[b]thiophene-2-carboxamide |
| 26 | 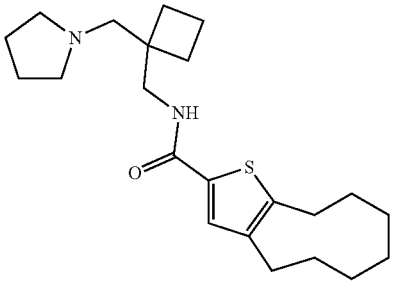 [SMILES: O=C(NCC1(CN2CCCC2)CCC1)c1cc2c(s1)CCCCCCC2] | N-[[1-(pyrrolidin-1-ylmethyl)cyclobutyl]methyl]-5,6,7,8,9,10-hexahydro-4H-cyclonona[b]thiophene-2-carboxamide |
| 27 | 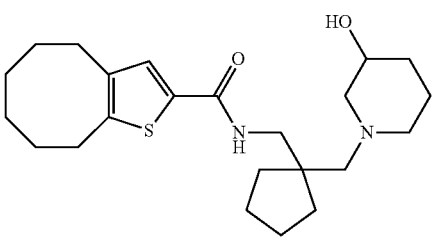 [SMILES: O=C(NCC1(CN2CCCC(O)C2)CCCC1)c1cc2c(s1)CCCCCC2] | N-[[1-[(3-hydroxypiperidin-1-yl)methyl]cyclopentyl]methyl]-4,5,6,7,8,9-hexahydrocycloocta[b]thiophene-2-carboxamide |

TABLE 2-continued

| Ex. | Structure | Chemical Name |
|---|---|---|
| 28 | 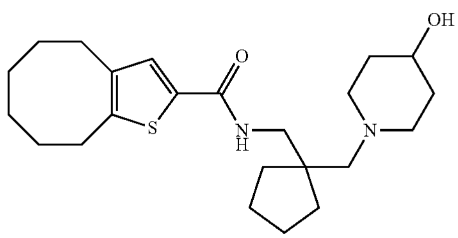 [SMILES: O=C(NCC1(CN2CCC(O)CC2)CCCC1)c1cc2c(s1)CCCCCC2] | N-[[1-[(4-hydroxypiperidin-1-yl)methyl]cyclopentyl]methyl]-4,5,6,7,8,9-hexahydrocycloocta[b]thiophene-2-carboxamide |
| 29 | 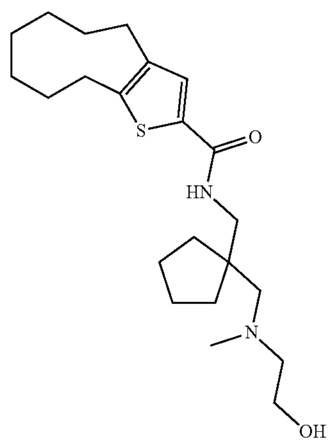 [SMILES: CN(CCO)CC1(CNC(=O)c2cc3c(s2)CCCCCCC3)CCCC1] | N-[[1-[[2-hydroxyethyl(methyl)amino]methyl]cyclopentyl]methyl]-5,6,7,8,9,10-hexahydro-4H-cyclonona[b]thiophene-2-carboxamide |
| 30 | 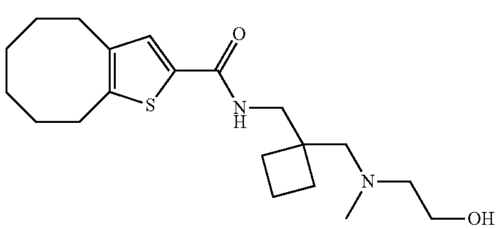 [SMILES: CN(CCO)CC1(CNC(=O)c2cc3c(s2)CCCCCC3)CCC1] | N-[[1-[[2-hydroxyethyl(methyl)amino]methyl]cyclobutyl]methyl]-4,5,6,7,8,9-hexahydrocycloocta[b]thiophene-2-carboxamide |
| 31 | 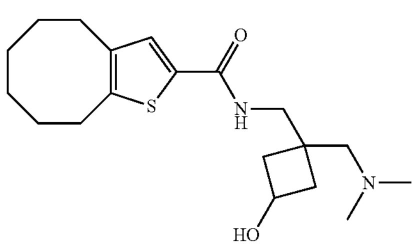 [SMILES: CN(C)CC1(CNC(=O)c2cc3c(s2)CCCCCC3)CC(O)C1] | N-[[1-[(dimethylamino)methyl]-3-hydroxycyclobutyl]methyl]-4,5,6,7,8,9-hexahydrocycloocta[b]thiophene-2-carboxamide |
| 32 | 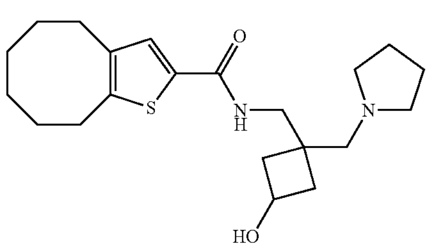 [SMILES: O=C(NCC1(CN2CCCC2)CC(O)C1)c1cc2c(s1)CCCCCC2] | N-[[3-hydroxy-1-(pyrrolidin-1-ylmethyl)cyclobutyl]methyl]-4,5,6,7,8,9-hexahydrocycloocta[b]thiophene-2-carboxamide |

TABLE 2-continued

| Ex. | Structure | Chemical Name |
|---|---|---|
| 33 | 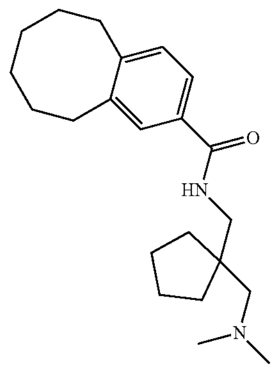 [SMILES: CN(C)CC1(CNC(=O)c2ccc3c(c2)CCCCCC3)CCCC1] | N-[[1-[(dimethylamino)methyl]cyclopentyl]methyl]-5,6,7,8,9,10-hexahydrobenzo[8]annulene-3-carboxamide |
| 34 | 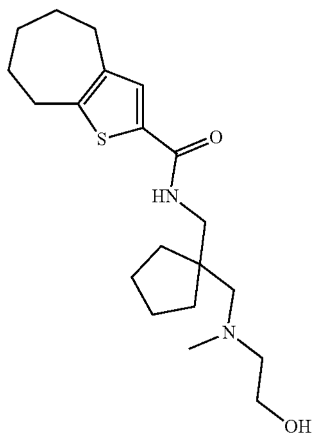 [SMILES: CN(CCO)CC1(CNC(=O)c2cc3c(s2)CCCCC3)CCCC1] | N-[[1-[[2-hydroxyethyl(methyl)amino]methyl]cyclopentyl]methyl]-5,6,7,8-tetrahydro-4H-cyclohepta[b]thiophene-2-carboxamide |
| 35 | 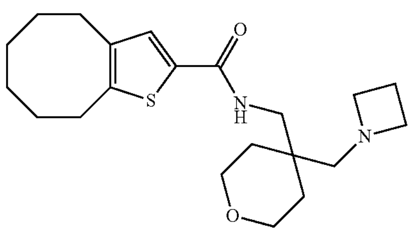 [SMILES: O=C(NCC1(CN2CCC2)CCOCC1)c1cc2c(s1)CCCCCC2] | N-[[4-(azetidin-1-ylmethyl)oxan-4-yl]methyl]-4,5,6,7,8,9-hexahydrocycloocta[b]thiophene-2-carboxamide |
| 36 | 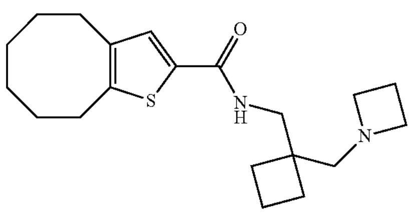 [SMILES: O=C(NCC1(CN2CCC2)CCC1)c1cc2c(s1)CCCCCC2] | N-[[1-(azetidin-1-ylmethyl)cyclobutyl]methyl]-4,5,6,7,8,9-hexahydrocycloocta[b]thiophene-2-carboxamide |
| 37 | 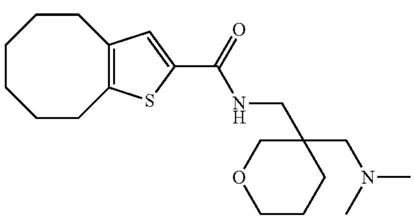 [SMILES: CN(C)CC1(CNC(=O)c2cc3c(s2)CCCCCC3)CCCOC1] | N-[[3-[(dimethylamino)methyl]oxan-3-yl]methyl]-4,5,6,7,8,9-hexahydrocycloocta[b]thiophene-2-carboxamide |

TABLE 2-continued

| Ex. | Structure | Chemical Name |
|---|---|---|
| 38 | 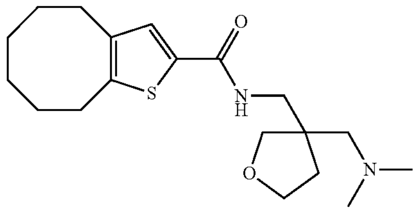 [SMILES: CN(C)CC1(CNC(=O)c2cc3c(s2)CCCCCC3)CCOC1] | N-[[3-[(dimethylamino)methyl]oxolan-3-yl]methyl]-4,5,6,7,8,9-hexahydrocycloocta[b]thiophene-2-carboxamide |
| 39 | 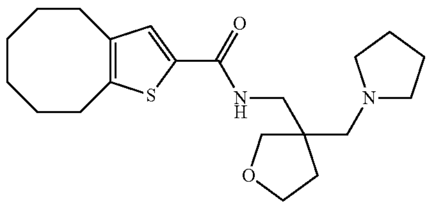 [SMILES: O=C(NCC1(CN2CCCC2)CCOC1)c1cc2c(s1)CCCCCC2] | N-[[3-(pyrrolidin-1-ylmethyl)oxolan-3-yl]methyl]-4,5,6,7,8,9-hexahydrocycloocta[b]thiophene-2-carboxamide |
| 40 | 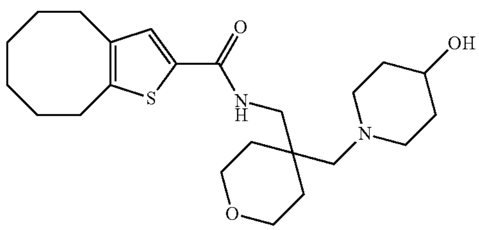 [SMILES: O=C(NCC1(CN2CCC(O)CC2)CCOCC1)c1cc2c(s1)CCCCCC2] | N-[[4-[(4-hydroxypiperidin-1-yl)methyl]oxan-4-yl]methyl]-4,5,6,7,8,9-hexahydrocycloocta[b]thiophene-2-carboxamide |
| 41 | 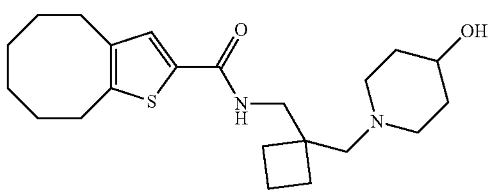 [SMILES: O=C(NCC1(CN2CCC(O)CC2)CCC1)c1cc2c(s1)CCCCCC2] | N-[[1-[(4-hydroxypiperidin-1-yl)methyl]cyclobutyl]methyl]-4,5,6,7,8,9-hexahydrocycloocta[b]thiophene-2-carboxamide |
| 42 | 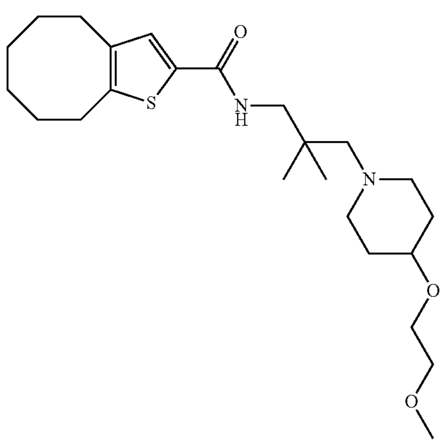 [SMILES: COCCOC1CCN(CC(C)(C)CNC(=O)c2cc3c(s2)CCCCCC3)CC1] | N-[3-[4-(2-methoxyethoxy)piperidin-1-yl]-2,2-dimethylpropyl]-4,5,6,7,8,9-hexahydrocycloocta[b]thiophene-2-carboxamide |
| 43 | 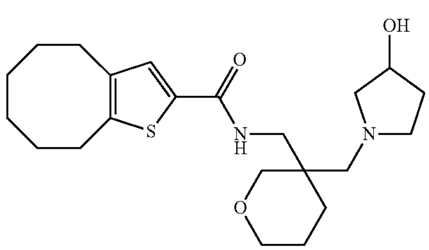 [SMILES: O=C(NCC1(CN2CCC(O)C2)CCCOC1)c1cc2c(s1)CCCCCC2] | N-[[3-[(3-hydroxypyrrolidin-1-yl)methyl]oxan-3-yl]methyl]-4,5,6,7,8,9-hexahydrocycloocta[b]thiophene-2-carboxamide |

TABLE 2-continued

| Ex. | Structure | Chemical Name |
|---|---|---|
| 44 | 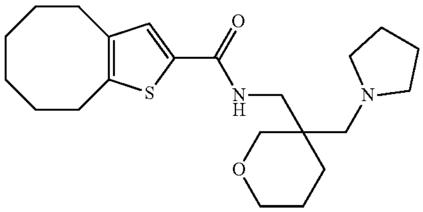 [SMILES: O=C(NCC1(CN2CCCC2)CCCOC1)c1cc2c(s1)CCCCCC2] | N-[[3-(pyrrolidin-1-ylmethyl)oxan-3-yl]methyl]-4,5,6,7,8,9-hexahydrocycloocta[b]thiophene-2-carboxamide |
| 45 | 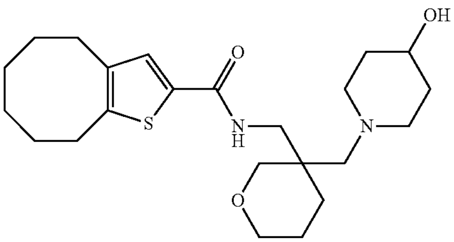 [SMILES: O=C(NCC1(CN2CCC(O)CC2)CCCOC1)c1cc2c(s1)CCCCCC2] | N-[[3-[(4-hydroxypiperidin-1-yl)methyl]oxan-3-yl]methyl]-4,5,6,7,8,9-hexahydrocycloocta[b]thiophene-2-carboxamide |
| 46 | 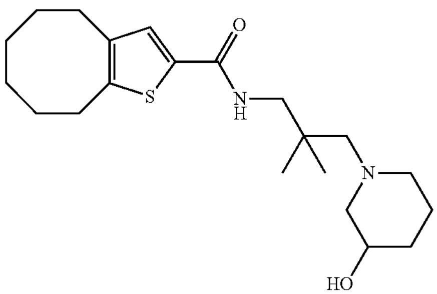 [SMILES: CC(C)(CNC(=O)c1cc2c(s1)CCCCCC2)CN1CCCC(O)C1] | N-[3-(3-hydroxypiperidin-1-yl)-2,2-dimethylpropyl]-4,5,6,7,8,9-hexahydrocycloocta[b]thiophene-2-carboxamide |
| 47 | 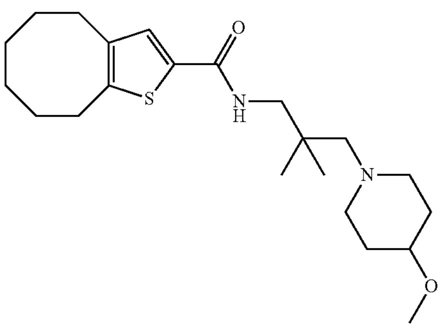 [SMILES: COC1CCN(CC(C)(C)CNC(=O)c2cc3c(s2)CCCCCC3)CC1] | N-[3-(4-methoxypiperidin-1-yl)-2,2-dimethylpropyl]-4,5,6,7,8,9-hexahydrocycloocta[b]thiophene-2-carboxamide |
| 48 | 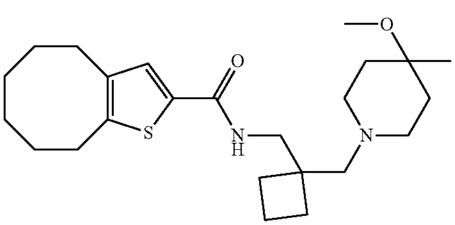 [SMILES: COC1(C)CCN(CC2(CNC(=O)c3cc4c(s3)CCCCCC4)CCC2)CC1] | N-[[1-[(4-methoxy-4-methylpiperidin-1-yl)methyl]cyclobutyl]methyl]-4,5,6,7,8,9-hexahydrocycloocta[b]thiophene-2-carboxamide |
| 49 | 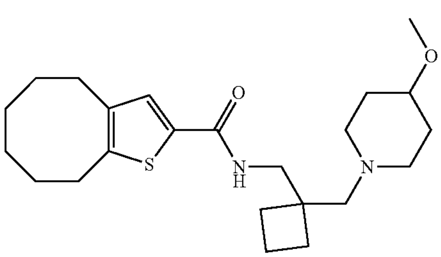 [SMILES: COC1CCN(CC2(CNC(=O)c3cc4c(s3)CCCCCC4)CCC2)CC1] | N-[[1-[(4-methoxypiperidin-1-yl)methyl]cyclobutyl]methyl]-4,5,6,7,8,9-hexahydrocycloocta[b]thiophene-2-carboxamide |

TABLE 2-continued

| Ex. | Structure | Chemical Name |
|---|---|---|
| 50 | 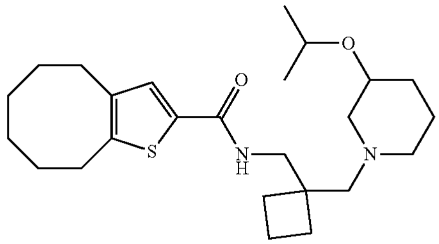 [SMILES: CC(C)OC1CCCN(CC2(CNC(=O)c3cc4c(s3)CCCCCC4)CCC2)C1] | N-[[1-[(3-propan-2-yloxypiperidin-1-yl)methyl]cyclobutyl]methyl]-4,5,6,7,8,9-hexahydrocycloocta[b]thiophene-2-carboxamide |
| 51 | 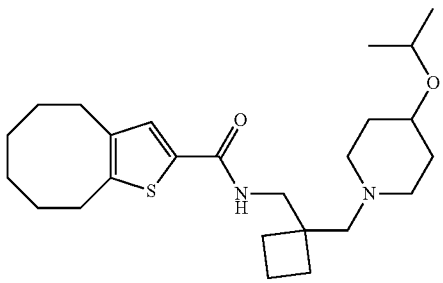 [SMILES: CC(C)OC1CCN(CC2(CNC(=O)c3cc4c(s3)CCCCCC4)CCC2)CC1] | N-[[1-[(4-propan-2-yloxypiperidin-1-yl)methyl]cyclobutyl]methyl]-4,5,6,7,8,9-hexahydrocycloocta[b]thiophene-2-carboxamide |
| 52 | 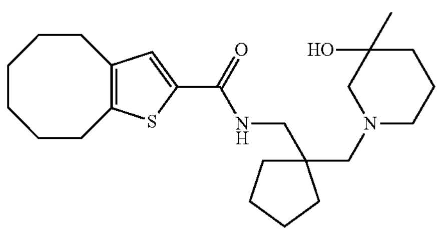 [SMILES: CC1(O)CCCN(CC2(CNC(=O)c3cc4c(s3)CCCCCC4)CCCC2)C1] | N-[[1-[(3-hydroxy-3-methylpiperidin-1-yl)methyl]cyclopentyl]methyl]-4,5,6,7,8,9-hexahydrocycloocta[b]thiophene-2-carboxamide |
| 53 | 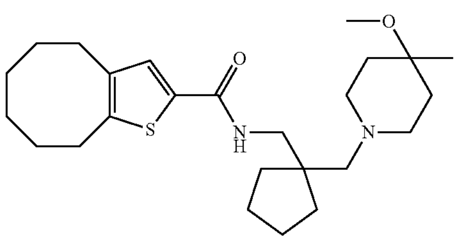 [SMILES: COC1(C)CCN(CC2(CNC(=O)c3cc4c(s3)CCCCCC4)CCCC2)CC1] | N-[[1-[(4-methoxy-4-methylpiperidin-1-yl)methyl]cyclopentyl]methyl]-4,5,6,7,8,9-hexahydrocycloocta[b]thiophene-2-carboxamide |
| 54 | 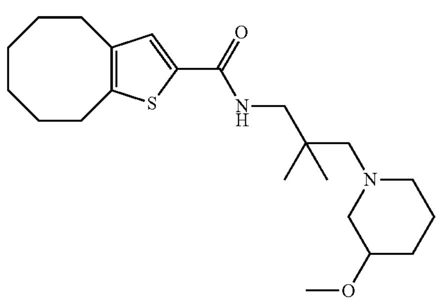 [SMILES: COC1CCCN(CC(C)(C)CNC(=O)c2cc3c(s2)CCCCCC3)C1] | N-[3-(3-methoxypiperidin-1-yl)-2,2-dimethylpropyl]-4,5,6,7,8,9-hexahydrocycloocta[b]thiophene-2-carboxamide |
| 55 | 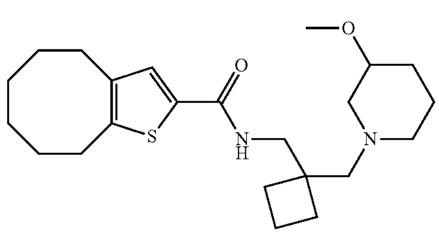 [SMILES: COC1CCCN(CC2(CNC(=O)c3cc4c(s3)CCCCCC4)CCC2)C1] | N-[3-(3-methoxypiperidin-1-yl)-2,2-dimethylpropyl]-4,5,6,7,8,9-hexahydrocycloocta[b]thiophene-2-carboxamide |

TABLE 2-continued

| Ex. | Structure | Chemical Name |
|---|---|---|
| 56 | 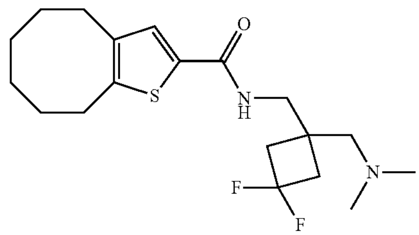 [SMILES: CN(C)CC1(CNC(=O)c2cc3c(s2)CCCCCC3)CC(F)(F)C1] | N-[[1-[(dimethylamino)methyl]-3,3-difluorocyclobutyl]methyl]-4,5,6,7,8,9-hexahydrocycloocta[b]thiophene-2-carboxamide |
| 57 | 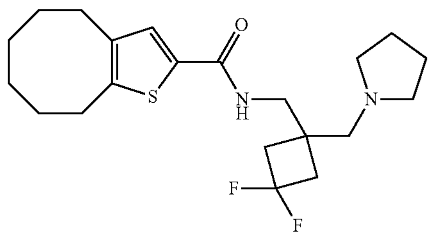 [SMILES: O=C(NCC1(CN2CCCC2)CC(F)(F)C1)c1cc2c(s1)CCCCCC2] | N-[[3,3-difluoro-1-(pyrrolidin-1-ylmethyl)cyclobutyl]methyl]-4,5,6,7,8,9-hexahydrocycloocta[b]thiophene-2-carboxamide |
| 58 | 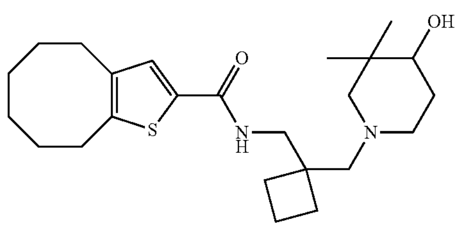 [SMILES: CC1(C)CN(CC2(CNC(=O)c3cc4c(s3)CCCCCC4)CCC2)CCC1O] | N-[[1-[(4-hydroxy-3,3-dimethylpiperidin-1-yl)methyl]cyclobutyl]methyl]-4,5,6,7,8,9-hexahydrocycloocta[b]thiophene-2-carboxamide |
| 59 | 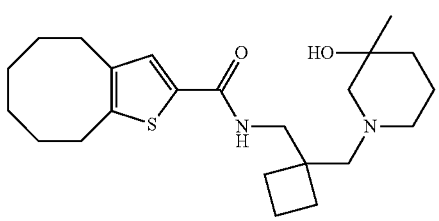 [SMILES: CC1(O)CCCN(CC2(CNC(=O)c3cc4c(s3)CCCCCC4)CCC2)C1] | N-[[1-[(3-hydroxy-3-methylpiperidin-1-yl)methyl]cyclobutyl]methyl]-4,5,6,7,8,9-hexahydrocycloocta[b]thiophene-2-carboxamide |
| 60 | 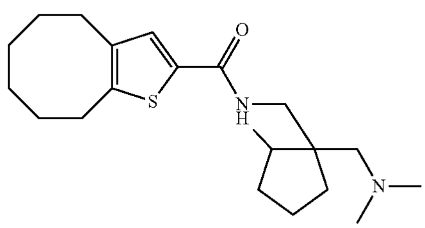 [SMILES: CC1CCCC1(CNC(=O)c1cc2c(s1)CCCCCC2)CN(C)C] | N-[[1-[(dimethylamino)methyl]-2-methylcyclopentyl]methyl]-4,5,6,7,8,9-hexahydrocycloocta[b]thiophene-2-carboxamide |
| 61 | 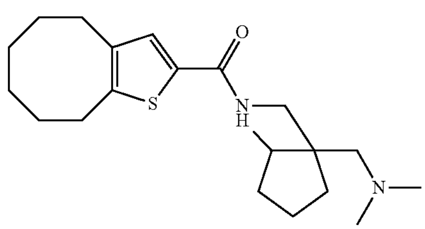 [SMILES: CC1CCCC1(CNC(=O)c1cc2c(s1)CCCCCC2)CN(C)C] | N-[[1-[(dimethylamino)methyl]-2-methylcyclopentyl]methyl]-4,5,6,7,8,9-hexahydrocycloocta[b]thiophene-2-carboxamide |
| 62 | 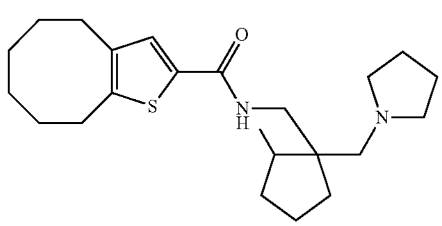 [SMILES: CC1CCCC1(CNC(=O)c1cc2c(s1)CCCCCC2)CN1CCCC1] | N-[[2-methyl-1-(pyrrolidin-1-ylmethyl)cyclopentyl]methyl]-4,5,6,7,8,9-hexahydrocycloocta[b]thiophene-2-carboxamide |

TABLE 2-continued

| Ex. | Structure | Chemical Name |
|---|---|---|
| 63 | 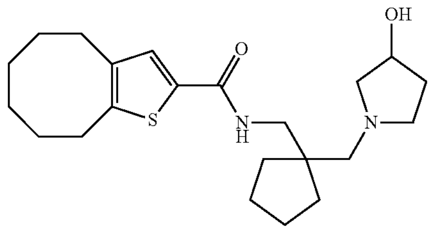 [SMILES: O=C(NCC1(CN2CCC(O)C2)CCCC1)c1cc2c(s1)CCCCCC2] | N-[[1-[(3-hydroxypyrrolidin-1-yl)methyl]cyclopentyl]methyl]-4,5,6,7,8,9-hexahydrocycloocta[b]thiophene-2-carboxamide |
| 64 | 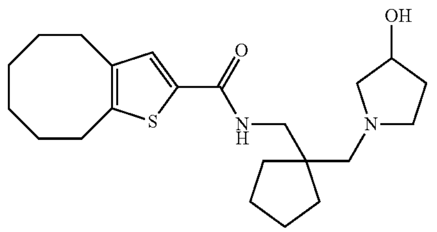 [SMILES: O=C(NCC1(CN2CCC(O)C2)CCCC1)c1cc2c(s1)CCCCCC2] | N-[[1-[(3-hydroxypyrrolidin-1-yl)methyl]cyclopentyl]methyl]-4,5,6,7,8,9-hexahydrocycloocta[b]thiophene-2-carboxamide |
| 65 | 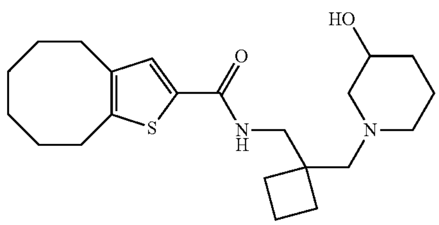 [SMILES: O=C(NCC1(CN2CCCC(O)C2)CCC1)c1cc2c(s1)CCCCCC2] | N-[[1-[(3-hydroxypiperidin-1-yl)methyl]cyclobutyl]methyl]-4,5,6,7,8,9-hexahydrocycloocta[b]thiophene-2-carboxamide |
| 66 | 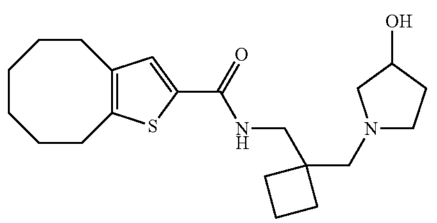 [SMILES: O=C(NCC1(CN2CCC(O)C2)CCC1)c1cc2c(s1)CCCCCC2] | N-[[1-[(3-hydroxypyrrolidin-1-yl)methyl]cyclobutyl]methyl]-4,5,6,7,8,9-hexahydrocycloocta[b]thiophene-2-carboxamide |
| 67 | 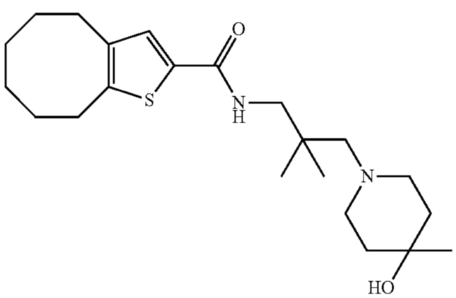 [SMILES: CC(C)(CNC(=O)c1cc2c(s1)CCCCCC2)CN1CCC(C)(O)CC1] | N-[3-(4-hydroxy-4-methylpiperidin-1-yl)-2,2-dimethylpropyl]-4,5,6,7,8,9-hexahydrocycloocta[b]thiophene-2-carboxamide |
| 68 | 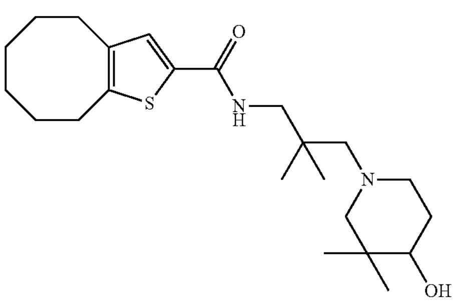 [SMILES: CC(C)(CNC(=O)c1cc2c(s1)CCCCCC2)CN1CCC(O)C(C)(C)C1] | N-[3-(4-hydroxy-3,3-dimethylpiperidin-1-yl)-2,2-dimethylpropyl]-4,5,6,7,8,9-hexahydrocycloocta[b]thiophene-2-carboxamide |

TABLE 2-continued

| Ex. | Structure | Chemical Name |
|---|---|---|
| 69 | 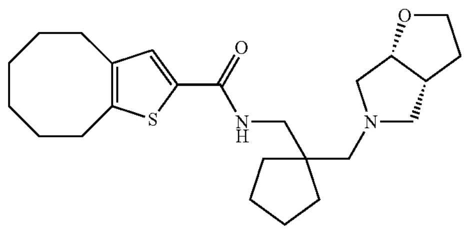 [SMILES: O=C(NCC1(CN2C[C@H]3CCO[C@H]3C2)CCCC1)c1cc2c(s1)CCCCCC2] | N-[[1-[[(3aR,6aS)-2,3,3a,4,6,6a-hexahydrofuro[2,3-c]pyrrol-5-yl]methyl]cyclopentyl]methyl]-4,5,6,7,8,9-hexahydrocycloocta[b]thiophene-2-carboxamide |
| 70 | 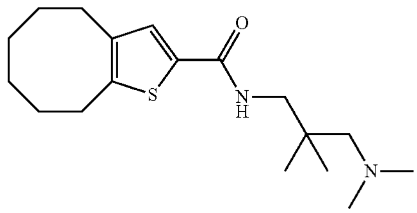 [SMILES: CN(C)CC(C)(C)CNC(=O)c1cc2c(s1)CCCCCC2] | N-[3-(dimethylamino)-2,2-dimethylpropyl]-4,5,6,7,8,9-hexahydrocycloocta[b]thiophene-2-carboxamide |

Analytical Procedures and Data

HPLC Preparation

HPLC system WATERS Quaternary Gradient Mobile 2535 equipped with WATERS UV/Visible Detector 2489 set to a dual-wavelength UV detection. Two mobile phases were used, mobile phase A: water (MilliQ) 0.05% TFA; mobile phase B: acetonitrile (Chromasolv Sigma-Aldrich) 0.05% TFA, and the run gradient conditions were set specifically for each compound. The purifications were achieved on a XBRIDGE Waters Column C18 5 µm 19×150. An injection volume between 100 and 500 µl was used and the flow was 15 ml/min.

Racemate Separations

The two enantiomers examples 63 and 64 were obtained by resolution of the racemic mixture example 25 using a WATERS Quaternary Gradient Mobile 2535 equipped with WATERS UV/Visible Detector 2489 set to a dual-wavelength UV detection at 250 and 265 nm. The chiral resolution was achieved on the Lux® 5 µm Amylose-1 column (250 mm×4.6 mm, particle size 5 m) using Hexane (Chromasolv Sigma-Aldrich)—Ethanol (Chromasolv Sigma-Aldrich) 70-30 (v/v) as isocratic mobile phase. The sample was eluted from the column at a flow rate of 1.0 ml/min at room temperature (Pressure: 500 psi). The mixture was dissolved in Ethanol at concentration of 1% (w/v) and the injection volume was 100 µL.

Additional racemic compounds disclosed herein may be separated by the methods disclosed above and known in the art, and once isolated, are provided for individually as stereoisomers A and B as above.

LCMS

LCMS General Procedure.

HPLC measurement was performed using a Dionex 3000 module comprising a quaternary pump with degasser, an autosampler, a column oven (set at 29° C.), a diode-array detector DAD and a column as specified in the respective methods below. Flow from the column was split to a MS spectrometer. The MS detector (LCQ Fleet Thermo Scientific) was configured with an electrospray ionization source. Mass spectra were acquired by scanning from 50 to 800 in 0.48 second. The capillary needle voltage was 5 kV in positive and negative ionization mode and the source temperature was maintained at 275° C. Nitrogen was used as the nebulizer gas, the flow was 8 l/min. Data acquisition was performed with Thermo Xcalibur Qual Browser.

LCMS—Method.

In addition to general procedure: Reversed phase HPLC was carried out on a Kinetex XB-C18 column Phenomenex (1.7 m, 50×2.1 mm) with a flow rate of 0.300 ml/min. Two mobile phases were used, mobile phase A: ammonium formate buffer solution at pH 3.5; mobile phase B: acetonitrile (Chromasolv Sigma-Aldrich), and they were employed to run a gradient conditions from 15% B for 0.5 minutes, from 15% to 98% in 4.0 minutes, 98% B for 1.35 minutes and 15% B in 0.10 minutes and hold these conditions for 2.75 minutes in order to reequilibrate the column (Total Run Time 8.7 minutes). An injection volume of 1 µl was used.

TABLE 3

Retention time ($R_t$) in minutes, [M + H]+ peak, LCMS procedure

| Example | RT (min) | [M + H]+ |
|---|---|---|
| 1 | 4.8 | 349.3 |
| 2 | 4.8 | 349.3 |
| 3 | 4.3 | 309.4 |
| 4 | 4.7 | 347.5 |
| 5 | 5.1 | 375.4 |
| 6 | 5.2 | 377.5 |
| 7 | 4.6 | 337.4 |
| 8 | 4.8 | 351.5 |
| 9 | 5.1 | 377.5 |
| 10 | 4.9 | 397.5 |
| 11 | 5.2 | 423.6 |
| 12 | 5.2 | 377.4 |
| 13 | 4.9 | 363.5 |
| 14 | 4.7 | 361.5 |
| 15 | 5.2 | 389.6 |
| 16 | 4.6 | 351.5 |
| 17 | 4.5 | 379.5 |
| 18 | 5.3 | 389.3 |
| 19 | 4.6 | 365.3 |
| 20 | 4.8 | 391.3 |
| 21 | 4.8 | 361.3 |
| 22 | 4.7 | 363.4 |
| 23 | 4.5 | 335.4 |
| 24 | 4.8 | 363.4 |
| 25 | 4.5 | 391.3 |
| 26 | 5.0 | 375.4 |
| 27 | 4.5 | 405.4 |
| 28 | 4.5 | 405.4 |
| 29 | 4.4 | 393.4 |

TABLE 3-continued

Retention time (R$_t$) in minutes, [M + H]$^+$ peak, LCMS procedure

| Example | RT (min) | [M + H]$^+$ |
|---|---|---|
| 30 | 4.3 | 365.4 |
| 31 | 4.2 | 351.3 |
| 32 | 4.3 | 377.5 |
| 33 | 4.8 | 343.4 |
| 34 | 4.4 | 365.4 |
| 35 | 4.5 | 377.2 |
| 36 | 5.6 | 347.2 |
| 37 | 4.4 | 365.2 |
| 38 | 4.3 | 351.3 |
| 39 | 4.7 | 3773 |
| 40 | 4.2 | 421.2 |
| 41 | 4.5 | 391.3 |
| 42 | 4.6 | 437.3 |
| 43 | 4.3 | 407.3 |
| 44 | 4.6 | 391.4 |
| 45 | 4.4 | 421.4 |
| 46 | 4.5 | 379.3 |
| 47 | 4.7 | 393.2 |
| 48 | 4.9 | 419.5 |
| 49 | 5.0 | 405.3 |
| 50 | 5.5 | 433.4 |
| 51 | 5.3 | 433.4 |
| 52 | 4.8 | 419.2 |
| 53 | 5.2 | 433.3 |
| 54 | 4.9 | 393.3 |
| 55 | 5.0 | 405.4 |
| 56 | 4.8 | 371.2 |
| 57 | 5.0 | 397.2 |
| 58 | 4.9 | 419.3 |
| 59 | 4.7 | 405.3 |
| 60 | 4.7 | 363.3 |
| 61 | 4.8 | 363.3 |
| 62 | 5.0 | 389.4 |
| 63 | 4.5 | 391.3 |
| 64 | 4.5 | 391.3 |
| 65 | 4.4 | 391.2 |
| 66 | 4.3 | 377.2 |
| 67 | 4.4 | 393.3 |
| 68 | 4.6 | 407.3 |
| 69 | 5.1 | 417.4 |
| 70 | | |

NMR Characterization $^1$H NMR spectra were recorded on a Varian Mercury NMR 400 MHz spectrometer using CDCl$_3$, DMSO-d or CDOD as solvents. Chemical shifts (δ) are reported in parts per million (ppm) relative to tetramethylsilane (TMS), which was used as internal standard.

TABLE 4

NMR data of compounds

| Example | $^1$H-NMR 400 |
|---|---|
| 1 | $^1$H NMR (400 MHz, CHLOROFORM-d) δ ppm 0.98 (s, 6 H) 1.33-1.45 (m, 4 H) 1.56-1.63 (m, 2 H) 1.63-1.70 (m, 2 H) 1.83 (br s, 4 H) 2.53 (s, 2 H) 2.62 (br d, J = 6.32 Hz, 2 H) 2.68 (br s, 4 H) 2.79-2.86 (m, 2 H) 3.32 (d, J = 4.49 Hz, 2 H) 7.15 (s, 1 H) 9.14 (br s, 1 H) |
| 2 | $^1$H NMR (400 MHz, CHLOROFORM-d) δ ppm 1.22-1.44 (m, 6 H) 1.51-1.76 (m, 10 H) 2.33 (s, 6 H) 2.43 (s, 2 H) 2.62 (t, J = 6.3 Hz, 2 H) 2.81 (t, J = 6.2 Hz, 2 H) 3.34 (d, J = 5.04 Hz, 2 H) 7.16 (s, 1 H) 8.84 (br s, 1 H). |
| 3 | $^1$H NMR (400 MHz, CHLOROFORM-d) δ ppm 1.00 (d, J = 6.60 Hz, 3 H) 1.28-1.47 (m, 4 H) 1.53-1.72 (m, 4 H) 2.21 (br s, 1 H) 2.45-2.55-2.67 (m, 9 H) 2.78-2.85 (m, 2 H) 2.86-3.07 (m, 1 H) 3.24-3.56 (m, 2 H) 7.32 (s, 1 H) 8.27 (br s, 1 H) 8.51 (s, 1 H) 9.97 (br s, 1 H). |
| 4 | $^1$H NMR (400 MHz, METHANOL-d$_4$) δ ppm 0.54 (s, 2H) 0.67-0.72 (m, 2 H) 1.53 (br d, J = 1.92 Hz, 4 H) 1.78 (br dd, J = 10.91, 4.40 Hz, 4 H) 1.95 (br s, 4 H) 2.63 (s, 2 H) 2.72 (br s, 4 H) 2.76-2.82 (m, 2 H) 2.95-3.01 (m, 2 H) 3.46 (s, 2 H) 7.38 (s, 1 H) |
| 5 | $^1$H NMR (400 MHz, CHLOROFORM-d) δ ppm 1.22-1.44 (m, 6 H) 1.47-1.73 (m, 10 H) 1.83 (br s, 4 H) 2.62 (m, 8 H) 2.75-2.89 (m, 2 H) 3.35 (br d, J = 4.77 Hz, 2 H) 7.13 (br s, 1 H) 9.07 (br s, 1 H). |
| 6 | $^1$H NMR (400 MHz, METHANOL-d$_4$) δ ppm 0.91 (t, J = 7.38 Hz, 3 H) 1.34-1.48 (m, 6 H) 1.49-1.78 (m, 12 H) 2.36 (br s, 3 H) 2.44 (br s, 2 H) 2.53 (br s, 2 H) 2.67 (t, J = 6.3 Hz, 2 H) 2.87 (t, J = 6.2 Hz, 2 H) 3.35 (s, 2 H) 7.23 (s, 1 H). |
| 7 | $^1$H NMR (400 MHz, METHANOL-d$_4$) δ ppm 1.00 (br s, 6 H) 1.37-1.50 (m, 4 H) 1.60-1.75 (m, 4 H) 2.29 (br s, 3 H) 2.34 (br s, 6 H) 2.68-2.75 (m, 2 H) 2.84-2.91 (m, 2 H) 3.35 (br s, 2 H) 3.53 (br s, 2 H) 7.24 (s, 1 H) |
| 8 | $^1$H NMR (400 MHz, METHANOL-d$_4$) δ ppm 0.84 (t, J = 7.5 Hz, 6 H) 1.22-1.41 (m, 8 H) 1.63-1.69 (m, 4 H) 2.40 (s, 6 H) 2.43 (s, 2 H) 2.70 (t, J = 6.2 Hz, 2 H) 2.87 (t, J = 6.1 Hz, 2 H) 3.31 (s, 2 H) 7.22 (s, 1 H). |
| 9 | $^1$H NMR (400 MHz, CHLOROFORM-d) δ ppm 0.81 (t, J = 7.5 Hz, 6H) 1.29-1.40 (m, 9H) 1.57-1.65 (m, 5H) 1.82 (br s, 4H) 2.55 (s, 2H) 2.60-2.67 (m, 6H) 2.81 (t, J = 6.12 Hz, 2H) 3.32 (br d, J = 4.32 Hz, 2H) 7.13 (s, 1H) 9.12 (br s, 1H). |
| 10 | $^1$H NMR (400 MHz, CHLOROFORM- d) δ ppm 1.40 (br s, 4 H) 1.63-1.68 (m, 4 H) 2.40 (s, 6 H) 2.64-266 (m, 4H) 2.80-2.89 (m, 6H) 3.49 (d, J = 4.48 Hz, 2H) 7.11-7.16 (m, 5H) 8.71 (br s, 1H). |
| 11 | $^1$H NMR (400 MHz, METHANOL-d$_4$) δ ppm 1.39 (br s, 4 H) 1.61-1.66 (m, 4 H) 1.84 (br s, 4 H) 2.63-2.68 (m, 6 H) 2.82-2.85 (m, 8 H) 3.43 (s, 2 H) 7.06-7.14 (m, 5H). |
| 12 | $^1$H NMR (400 MHz, CHLOROFORM-d) δ ppm 1.04 (t, J = 7.10 Hz, 6 H) 1.28-1.35 (m, 6 H) 1.51-1.68 (m, 10 H) 2.49 (s, 2 H) 2.56-262 (m, 6 H) 2.80 (t, J = 6.14 Hz, 2H) 3.33 (br d, J = 4.48 Hz, 2 H) 7.16 (s, 1 H) 8.91 (br s, 1 H). |

TABLE 4-continued

NMR data of compounds

| Example | ¹H-NMR 400 |
|---|---|
| 13 | ¹H NMR (400 MHz, CHLOROFORM-d) δ ppm 0.93 (s, 6 H) 1.25-1.45 (m, 6 H) 1.52-1.71 (m, 8 H) 2.26 (s, 2 H) 2.48 (br s, 4 H) 2.57-2.67 (m, 2 H) 2.73-2.86 (m, 2 H) 3.26 (d, J = 4.40 Hz, 2 H) 7.26 (s, 1 H) 8.76 (br s, 1 H). |
| 14 | ¹H NMR (400 MHz, CHLOROFORM-d) δ ppm 1.24-1.66 (m, 16 H) 2.21-2.23 (m, 2 H) 2.62-2.66 (m, 4 H) 2.82-2.85 (t, J = 6.14 Hz, 2 H) 3.27 (br d, J = 4.76 Hz, 2 H) 3.51 (br s, 4 H) 7.33 (s, 1H) 9.19 (br s, 1 H). |
| 15 | ¹H NMR (400 MHz, CHLOROFORM-d) δ ppm 1.32-1.37 (m, 8 H) 1.56-1.64 (m, 14 H) 2.37(s, 2 H) 2.46 (br s, 4 H) 2.60 (t, J = 6.26 Hz, 2 H) 2.80 (t, J = 6.14 Hz, 2 H) 3.31 (br d, J = 4.88 Hz, 2 H) 7.22 (s, 1 H) 8.73 (br s, 1 H). |
| 16 | ¹H NMR (400 MHz, METHANOL-d₄) δ ppm 0.95 (s, 6 H) 1.05 (t, J = 7.10 Hz, 6 H) 1.40 (br s, 4 H) 1.56-1.74 (m, 4 H) 2.40 (s, 2 H) 2.59 (q, J = 7.06 Hz, 4 H) 2.63-2.74 (m, 2 H) 2.80-2.92 (m, 2 H) 3.24 (s, 2 H) 7.27 (s, 1 H). |
| 17 | ¹H NMR (400 MHz, METHANOL-d₄) δ ppm 1.40-1.41 (m, 6 H) 1.60-1.71 (m, 10 H) 2.40 (s, 3 H), 2.58 (br s, 2 H) 2.68-2.71 (m, 4 H) 2.87 (t, J = 6.14 Hz, 2 H) 3.37 (s, 2 H) 3.71 (t, J = 5.54 Hz, 2 H) 7.39 (s, 1 H). |
| 18 | ¹H NMR (400 MHz, METHANOL-d₄) δ ppm 1.29-1.50 (m, 14 H) 1.62-1.66 (m, 4 H) 1.83 (br s, 4 H) 2.26 (s, 2 H) 2.64-2.69 (m, 6 H) 2.85 (t, J = 6.10 Hz, 2 H) 3.40 (s, 2 H), 7.18 (s, 1 H). |
| 19 | ¹H NMR (400 MHz, METHANOL-d₄) δ ppm 1.40-1.54 (m, 8 H) 1.63-1.67 (m, 4 H) 2.37 (s, 6 H) 2.42 (s, 2 H) 2.68 (t, J = 6.22 Hz, 2 H) 2.86 (t, J = 6.14 Hz, 2 H) 3.52 (s, 2 H) 3.67-3.69 (m, 4 H) 7.25 (s, 1 H). |
| 20 | ¹H NMR (400 MHz, METHANOL-d₄) δ ppm 1.40-1.49 (m, 8 H), 1.53-1.67 (m, 4 H) 1.84 (br s, 4 H) 2.63-2.70 (m, 8 H) 2.86 (t, J = 6.14 Hz, 2 H) 3.54 (s, 2 H) 3.66-3.72 (m, 4 H) 7.21 (s, 1 H). |
| 21 | ¹H NMR (400 MHz, METHANOL-d₄) δ ppm 1.33-1.48 (m, 4 H) 1.57-1.73 (m, 4 H) 1.76-1.94 (m, 10 H) 2.57 (br s, 4 H) 2.62-2.72 (m, 4 H) 2.80-2.91 (m, 2 H) 3.26-3.33 (m, 2 H) 7.21 (s, 1 H) |
| 22 | ¹H NMR (400 MHz, METHANOL-d₄) δ ppm 1.18-1.58 (m, 14 H) 1.59-1.75 (m, 4 H) 2.29-2.45 (m, 8 H) 2.69 (t, J = 6.24 Hz, 2 H) 2.87 (t, J = 6.14 Hz, 2 H) 3.41 (s, 2 H) 7.22 (s, 1 H). |
| 23 | ¹H NMR (400 MHz, METHANOL-d₄) δ ppm 1.30-1.50 (m, 4 H) 1.57-1.73 (m, 4 H) 1.79-1.92 (m, 5 H) 1.96-2.11 (m, 1 H) 2.25 (s, 6 H) 2.45 (s, 2 H) 2.61-2.75 (m, 2 H) 2.81-2.90 (m, 2 H) 3.58 (s, 2 H) 7.26 (s, 1 H). |
| 24 | ¹H NMR (400 MHz, METHANOL-d₄) δ ppm 0.92-1.01 (m, 6 H) 1.25-1.53 (m, 8 H) 1.60-1.87 (m, 8 H) 2.54 (s, 2 H) 2.70 (br t, J = 6.02 Hz, 6 H) 2.83-2.92 (m, 2 H) 7.22 (s, 1 H). |
| 25 | ¹H NMR (400 MHz, CHLOROFORM-d) δ ppm 1.36 (br s, 6 H) 1.48-1.76 (m, 10 H) 1.92 (br s, 2 H) 2.26 (br s, 2 H) 2.54-2.67 (m, 2 H) 2.76-3.01 (m, 7 H) 3.30 (br s, 3 H) 4.52 (br s, 1 H) 7.38 (br s, 1 H). |
| 26 | ¹H NMR (400 MHz, CHLOROFORM-d) δ ppm 1.23-1.50 (m, 8 H) 1.52-1.76 (m, 10 H) 1.83 (br s, 4 H) 2.54-2.71 (m, 6 H) 2.71-2.91 (m, 2 H) 3.35 (br d, J = 4.77 Hz, 2 H) 7.13 (br s, 1 H) 9.07 (br s, 1 H). |
| 27 | ¹H NMR (400 MHz, METHANOL-d₄) δ ppm 1.41 (br s, 6 H) 1.49-1.76 (m, 12 H) 1.79-1.90 (m, 2 H) 2.29 (br s, 2 H) 2.45 (s, 2 H) 2.66-2.74 (m, 2 H) 2.80 (s, 1 H) 2.83-2.93 (m, 3 H) 3.34 (s, 2 H) 3.61 (br d, J = 4.21 Hz, 1 H) 7.27-7.36 (m, 1 H). |
| 28 | ¹H NMR (400 MHz, METHANOL-d₄) δ ppm 1.41 (br s, 6 H) 1.49-1.89 (m, 14 H) 2.05-2.33 (m, 2 H) 2.47 (br s, 2 H) 2.62-2.75 (m, 3 H) 2.82-2.96 (m, 3 H) 3.24-3.45 (m, 2 H) 3.74 (br s, 1 H) 7.40 (s, 1 H). |
| 29 | ¹H NMR (400 MHz, CHLOROFORM-d) δ ppm 1.29-1.48 (m, 6 H) 1.57-1.77 (m, 10 H) 1.91 (quin, J = 5.98 Hz, 2 H) 2.55-2.66 (m, 3 H) 2.69 (s, 3 H) 2.74-2.88 (m, 4 H) 3.04 (br t, J = 6.51 Hz, 2 H) 3.29 (br d, J = 6.05 Hz, 2 H) 3.74-3.87 (m, 2 H) 7.39 (s, 1 H). |
| 30 | ¹H NMR (400 MHz, CHLOROFORM-d) δ ppm 1.35 (br d, J = 1.83 Hz, 4 H) 1.52-1.68 (m, 4 H) 1.74-1.90 (m, 5 H) 1.99-2.16 (m, 1 H) 2.33 (s, 3 H) 2.54-2.69 (m, 6 H) 2.71-2.87 (m, 2 H) 3.65 (d, J = 5.96 Hz, 2 H) 3.72 (t, J = 5.27 Hz, 2 H) 7.31 (s, 1 H) 7.88 (br s, 1 H). |
| 31 | ¹H NMR (400 MHz, CHLOROFORM-d) δ ppm 1.36 (br s, 4 H) 1.41-1.59 (m, 4 H) 1.96-2.00 (m, 2 H) 2.22-2.23 (m, 2 H) 2.39-2.41 (m, 6 H) 2.60-2.64 (m, 4 H) 2.81 (t, J = 5.98 Hz, 2 H) 3.52-3.67 (m, 2 H) 4.26-4.32 (m, 1 H) 7.25 (s, 1 H) 8.31 (br s, 1 H). |
| 32 | ¹H NMR (400 MHz, CHLOROFORM-d) δ ppm 1.35 (br s, 4 H) 1.57-1.63 (m, 4 H) 1.82-1.89 (m, 6 H) 2.20-2.22 (m, 2 H) 2.26-2.80 (m, 10 H) 3.47-3.65 (m, 2 H) 4.27-4.48 (m, 2 H) 7.15 (s, 1 H) 8.57 (br s, 1 H). |
| 33 | ¹H NMR (400 MHz, METHANOL-d4) δ ppm 1.28-1.48 (m, 6 H) 1.53-1.78 (m, 10 H) 2.35 (s, 6 H) 2.48 (s, 2 H) 2.74-2.88 (m, 5 H) 3.39 (s, 2 H) 7.19 (d, J = 7.53 Hz, 1 H) 7.44-7.57 (m, 2 H) |
| 34 | ¹H NMR (400 MHz, CHLOROFORM-d) δ ppm 1.21-1.37 (m, 2 H) 1.52-1.77 (m, 10 H) 1.77-1.88 (m, 2 H) 2.36 (s, 3 H) 2.51 (br s, 1 H) 2.49 (s, 1 H) 2.55-2.69 (m, 1 H) 2.55-2.69 (m, 3 H) 2.71-2.83 (m, 2 H) 3.35 (d, J = 5.59 Hz, 2 H) 3.73 (t, J = 5.45 Hz, 2 H) 7.25 (s, 1 H) 7.88 (br s, 1 H). |
| 35 | ¹H NMR (400 MHz, CHLOROFORM-d) δ ppm 1.30-1.43 (m, 2 H) 1.30-1.43 (m, 1 H) 1.53-1.74 (m, 4 H) 1.75-2.00 (m, 6 H) 2.06-2.19 (m, 2 H) 2.32 (br s, 2 H) 2.54-2.69 (m, 2 H) 2.69-2.79 (m, 1 H) 2.79-2.87 (m, 4 H) 2.89 (br s, 1 H) 3.49-3.65 (m, 4 H) 3.65-3.77 (m, 2 H) 7.20-7.30 (m, 1 H) 7.43 (br s, 1 H). |

TABLE 4-continued

NMR data of compounds

| Example | ¹H-NMR 400 |
|---|---|
| 36 | ¹H NMR (400 MHz, CHLOROFORM-d) δ ppm 1.24 (s, 2 H) 1.31-1.50 (m, 6 H) 1.50-1.78 (m, 6 H) 2.51-2.63 (m, 2 H) 2.72-2.81 (m, 3 H) 2.81-2.95 (m, 2 H) 3.31 (br s, 1 H) 3.54-3.67 (m, 4 H) 4.04 (br s, 3 H) 6.64 (s, 1 H). |
| 37 | ¹H NMR (400 MHz, METHANOL-$d_4$) δ ppm 1.35-1.46 (m, 4 H) 1.45-1.75 (m, 8 H) 2.36 (s, 6 H) 2.62-2.74 (m, 2 H) 2.81-2.92 (m, 2 H) 3.27-3.70 (m, 8 H) 7.26 (s, 1 H) |
| 38 | ¹H NMR (400 MHz, CHLOROFORM-d) δ ppm 1.30-1.45 (m, 4 H) 1.53-1.72 (m, 5 H) 1.85-1.91 (m, 1 H) 2.33 (s, 6 H) 2.48 (d, J = 13.28 Hz, 1 H) 2.56 (d, J = 13.24 Hz, 1 H) 2.63 (t, J = 6.22 Hz, 2 H) 2.82 (t, J = 6.14 Hz, 2 H) 3.43-3.49 (m, 2 H) 3.53-3.58 (m, 1 H) 3.71 (d, J = 8.71 Hz, 1 H) 3.78-3.84 (m, 1 H) 3.88-3.94 (m, 1 H) 7.17 (s, 1 H) 8.36 (br s, 1 H) |
| 39 | ¹H NMR (400 MHz, CHLOROFORM-d) δ ppm 1.38 (br s, 4 H) 1.60-1.71 (m, 5 H) 1.86 (br s, 5 H) 2.61-2.69 (m, 6 H) 2.73-2.76 (m, 2 H) 2.79-2.87 (m, 2 H) 3.46-3.51 (m, 2 H) 3.54-3.59 (m, 1 H) 3.71 (d, J = 8.71 Hz, 1 H) 3.81-3.87 (m, 1 H) 3.90-3.96 (m, 1 H) 7.15 (s, 1 H) 8.71 (br s, 1 H) |
| 40 | ¹H NMR (400 MHz, CHLOROFORM- d) δ ppm 1.35 (br d, J = 1.92 Hz, 5 H) 1.41-1.53 (m, 4H) 1.53-1.70 (m, 6 H) 1.87 (br d, J = 9.90 Hz, 2 H) 2.13 (s, 3 H) 2.39 (br s, 3 H) 2.57-2.65 (m, 2 H) 2.76-2.85 (m, 3 H) 3.52 (d, J = 4.77 Hz, 2 H) 3.59-3.68 (m, 4 H) 7.21-7.30 (m, 1 H) 8.53 (br s, 1 H). |
| 41 | ¹H NMR (400 MHz, CHLOROFORM- d) δ ppm 1.27-1.46 (m, 6 H) 1.48-1.70 (m, 6 H) 1.79 (br s, 4 H) 1.83-1.91 (m, 3 H) 1.98-2.13 (m, 2 H) 2.39-2.53 (m, 2 H) 2.53-2.66 (m, 2 H) 2.67-2.85 (m, 4 H) 3.60 (br d, J = 5.41 Hz, 3 H) 7.20-7.30 (m, 1 H) 7.25 (br s, 1 H) 8.32 (br s, 1 H). |
| 42 | ¹H NMR (400 MHz, CHLOROFORM- d) δ ppm 0.93 (s, 6 H) 1.29-1.45 (m, 4 H) 1.52-1.72 (m, 6 H) 1.77-1.93 (m, 2 H) 2.29 (br s, 4 H) 2.58-2.66 (m, 2 H) 2.77-2.87 (m, 4 H) 3.26 (d, J = 4.49 Hz, 2 H) 3.35 (s, 3 H) 3.46-3.52 (m, 2 H) 3.53-3.58 (m, 2 H) 3.71 (br t, J = 6.51 Hz, 1H) 7.17-7.29 (m, 1 H) 8.53 (br s, 1 H). |
| 43 | ¹H NMR (400 MHz, METHANOL-$d_4$) δ ppm 1.23-1.46 (m, 4 H) 1.52-1.80 (m, 8 H) 2.09-2.24 (m, 1 H) 2.56-2.76 (m, 4 H) 2.76-2.94 (m, 4 H) 3.36-3.63 (m, 5 H) 3.65-3.85 (m, 2 H) 4.38 (br s, 1 H) 7.43 (s, 1 H) |
| 44 | ¹H NMR (400 MHz, METHANOL-$d_4$) δ ppm 1.21-1.46 (m, 4 H) 1.47-1.74 (m, 8 H) 1.85 (br s, 4 H) 2.53-2.78 (m, 6 H) 2.78-2.92 (m, 2 H) 3.37-3.46 (m, 2 H) 3.46-3.58 (m, 4 H) 3.62-3.74 (m, 2 H) 7.22 (s, 1 H) |
| 45 | ¹H NMR (400 MHz, METHANOL-$d_4$) δ ppm 1.27-1.46 (m, 4 H) 1.47-1.72 (m, 10 H) 1.83 (br d, J = 9.39 Hz, 2 H) 2.35 (br d, J = 13.99 Hz, 3 H) 2.42-2.56 (m, 1 H) 2.63-2.77 (m, 2 H) 2.77-2.95 (m, 4 H) 3.35 (d, J = 13.60 Hz, 1 H) 3.41-3.67 (m, 6 H) 7.34 (s, 1 H) |
| 46 | ¹H NMR (400 MHz, METHANOL-$d_4$) δ ppm 0.95 (s, 6 H) 1.35-1.47 (m, 4 H) 1.50-1.77 (m, 6H) 1.82 (br dd, J = 12.18, 4.45 Hz, 1 H) 2.11-2.36 (m, 4 H) 2.58-2.78 (m, 4 H) 2.78-2.97 (m, 3 H) 3.18-3.29 (m, 2 H) 3.71 (dt, J = 8.56, 4.52 Hz, 1 H) 7.41 (s, 1 H) |
| 47 | ¹H NMR (400 MHz, METHANOL-$d_4$) δ ppm 0.94 (s, 6 H) 1.33-1.47 (m, 4 H) 1.52-1.74 (m, 6 H) 1.79-1.95 (m, 2 H) 2.23-2.39 (m, 3 H) 2.60-2.75 (m, 2 H) 2.75-2.93 (m, 4 H) 3.17-3.27 (m, 3 H) 3.30 (s, 3 H) 7.34 (s, 1 H) |
| 48 | ¹H NMR (400 MHz, CHLOROFORM- d) δ ppm 1.06-1.18 (m, 4 H) 1.33-1.43 (m, 4 H) 1.51-1.71 (m, 6 H) 1.71-1.98 (m, 8 H) 2.07-2.19 (m, 2 H) 2.42-2.71 (m, 8 H) 2.74-3.00 (m, 4 H) 3.66 (br s, 2 H) 7.18-7.40 (m, 1 H). |
| 49 | ¹H NMR (400 MHz, METHANOL-$d_4$) δ ppm 1.33-1.50 (m, 5 H) 1.50-1.77 (m, 8 H) 1.87 (br s, 6 H) 1.94-2.51 (br s, 3 H) 2.58-2.75 (m, 3 H) 2.75-2.92 (m, 4 H) 3.07-3.28 (m, 2 H) 3.60 (s, 2 H) 4.09 (q, J = 7.14 Hz, 1 H) 7.33 (s, 1 H) |
| 50 | ¹H NMR (400 MHz, METHANOL-$d_4$) δ ppm 1.02-1.13 (m, 6 H) 1.35-1.54 (m, 4 H) 1.61-1.90 (m, 12 H) 1.95-2.16 (m, 4 H) 2.47 (d, J = 2.84 Hz, 2 H) 2.54 (br s, 1 H) 2.64-2.73 (m, 2 H) 2.78 (br d, J = 10.56 Hz, 1 H) 2.84-2.89 (m, 2 H) 3.40-3.51 (m, 2 H) 3.60-3.70 (m, 1 H) 3.78 (d, J = 13.50 Hz, 1 H) 7.40 (s, 1 H) |
| 51 | ¹H NMR (400 MHz, CHLOROFORM- d) δ ppm 1.10 (d, J = 6.14 Hz, 6 H) 1.31-1.44 (m, 4 H) 1.52-1.70 (m, 6 H) 1.72-1.88 (m, 7 H) 1.99-2.19 (m, 3 H) 2.44 (s, 2 H) 2.58-2.67 (m, 2 H) 2.71-2.87 (m, 4 H) 3.27-3.40 (m, 1 H) 3.59-3.71 (m, 3 H) 7.21 (s, 1 H) 8.31 (br s, 1 H). |
| 52 | ¹H NMR (400 MHz, CHLOROFORM- d) δ ppm 1.04-1.13 (m, 1 H) 1.05-1.20 (m, 1 H) 1.20-1.29 (m, 4 H) 1.31-1.45 (m, 1 H) 1.33-1.54 (m, 8 H) 1.55-1.76 (m, 12 H) 2.60-2.69 (m, 3 H) 2.76-2.88 (m, 3 H) 3.24-3.47 (m, 3 H) 7.35 (s, 1 H). |
| 53 | ¹H NMR (400 MHz, CHLOROFORM- d) δ ppm 1.18 (s, 4 H) 1.08-1.17 (m, 4 H) 1.28-1.44 (m, 6 H) 1.50-1.85 (m, 8 H) 2.41-2.53 (m, 6 H) 2.54-2.67 (m, 4 H) 2.78-2.86 (m, 4 H) 3.30-3.41 (m, 2 H) 7.21-7.28 (m, 1 H) 8.71 (br s, 1 H). |
| 54 | ¹H NMR (400 MHz, CHLOROFORM- d) δ ppm 0.95 (d, 6 H) 1.31-1.45 (m, 4 H) 1.46-1.57 (m, 2 H) 1.57-1.71 (m, 4 H) 1.71-1.93 (m, 2 H) 2.30 (s, 2 H) 2.40 (br s, 2 H) 2.58-2.69 (m, 2 H) 2.79-2.87 (m, 2 H) 3.19-3.27 (m, 2 H) 3.28 (s, 2 H) 3.25 (s, 2 H) 3.30-3.42 (m, 2 H) 7.36 (s, 1 H) 8.43 (br s, 1 H). |
| 55 | ¹H NMR (400 MHz, CHLOROFORM- d) δ ppm 1.26-1.41 (m, 6 H) 1.52-1.68 (m, 4 H) 1.68-1.87 (m, 8 H) 2.22 (br s, 2 H) 2.43 (br s, 3 H) 2.57-2.65 (m, 2 H) 2.72-2.82 (m, 3 H) 3.25 (s, 3 H) 3.27-3.35 (m, 1 H) 3.49 (br dd, J = 13.47, 4.67 Hz, 1 H) 3.74 (dd, J = 13.47, 5.96 Hz, 1 H) 7.20-7.36 (m, 1 H) 8.17 (br s, 1 H). |
| 56 | ¹H NMR (400 MHz, CHLOROFORM- d) δ ppm 1.31-1.44 (m, 4 H) 1.56-1.70 (m, 4 H) 2.24-2.41 (m, 8 H) 2.46-2.58 (m, 4 H) 2.58-2.68 (m, 2 H) 2.78-2.86 (m, 2 H) 3.64 (d, J = 5.41 Hz, 2 H) 7.17 (s, 1 H) 8.07 (br s, 1 H). |

TABLE 4-continued

NMR data of compounds

| Example | ¹H-NMR 400 |
|---|---|
| 57 | ¹H NMR (400 MHz, CHLOROFORM- d) δ ppm 1.38 (br d, J = 1.65 Hz, 4 H) 1.55-1.71 (m, 1 H) 1.55-1.71 (m, 3 H) 1.80 (br s, 1 H) 1.83 (br s, 3 H) 2.34 (q, J = 13.90 Hz, 2 H) 2.42-2.54 (m, 2 H) 2.56-2.66 (m, 6 H) 2.77 (s, 2 H) 2.80-2.86 (m, 2 H) 3.64 (d, J = 5.04 Hz, 2 H) 7.13 (s, 1 H) 8.52 (br s, 1 H). |
| 58 | ¹H NMR (400 MHz, CHLOROFORM- d) δ ppm 1.04-1.16 (m, 6 H) 1.35 (br s, 4 H) 1.53-1.69 (m, 4 H) 1.82-2.18 (m, 8 H) 2.61 (br d, J = 6.78 Hz, 4 H) 2.77-2.94 (m, 5 H) 3.07-3.20 (m, 2 H) 3.53-3.70 (m, 3 H) 7.41-7.51 (m, 1 H) 7.78 (br s, 1 H). |
| 59 | H NMR (400 MHz, CHLOROFORM- d) δ ppm 1.17 (s, 3 H) 1.30-1.45 (m, 4 H) 1.46-1.56 (m, 2 H) 1.56-1.74 (m, 4 H) 1.74-1.97 (m, 8 H) 1.97-2.17 (m, 4 H) 2.35-2.56 (m, 4 H) 2.56-2.66 (m, 2 H) 2.77-2.86 (m, 2 H) 3.54-3.66 (m, 1 H) 3.66-3.77 (m, 1 H) 7.29 (s, 1 H). |
| 60 | ¹H NMR (400 MHz, METHANOL-$d_4$) δ ppm 1.00 (d, J = 6.94 Hz, 3 H) 1.35-1.55 (m, 6H) 1.61-1.80 (m, 7 H) 1.84-1.96 (m, 2 H) 2.15 (s, 1 H) 2.54 (br d, J = 13.40 Hz, 1 H) 2.60-2.72 (m, 7 H) 2.80-2.93 (m, 2 H) 3.03 (br d, J = 13.60 Hz, 1 H) 3.21 (br d, J = 14.18 Hz, 1 H) 3.44 (d, J = 14.18 Hz, 1 H) 7.33 (s, 1 H) 8.53 (s, 1 H) |
| 61 | ¹H NMR (400 MHz, METHANOL-$d_4$) δ ppm 0.88 (d, J = 7.04 Hz, 3 H) 1.10-1.36 (m, 3 H) 1.40 (br s, 2 H) 1.45-1.60 (m, 2 H) 1.60-1.70 (m, 6 H) 1.70-1.80 (m, 2 H) 1.92-2.02 (m, 1 H) 2.29-2.38 (m, 6 H) 2.51 (br d, J = 13.60 Hz, 1 H) 2.63-2.71 (m, 2 H) 2.81-2.89 (m, 2 H) 3.26-3.32 (m, 2 H) 3.37-3.44 (m, 1 H) 7.22 (s, 1 H) |
| 62 | ¹H NMR (400 MHz, METHANOL-$d_4$) δ ppm 0.93-1.06 (m, 3 H) 1.33-1.48 (m, 4 H) 1.49-1.58 (m, 1H) 1.60-1.93 (m, 8 H) 1.97-2.09 (m, 1H) 2.01-2.18 (m, 6 H) 2.71 (t, J = 6.16 Hz, 2 H) 2.80-2.85 (m, 1H) 2.89 (t, J = 6.1 Hz, 2 H) 2.98-3.13 (m, 2 H) 3.34-3.50 (m, 4 H) 7.42 (s, 1 H) |
| 63 | ¹H NMR (400 MHz, METHANOL-$d_4$) δ ppm 1.41 (br s, 6 H) 1.51-1.85 (m, 10 H) 2.12-2.21 (m, 1 H) 2.47-2.82 (m, 7 H) 2.83-2.91 (m, 2 H) 2.95 (br s, 1 H) 3.22-3.34 (m, 2 H) 3.42 (d, J = 13.36 Hz, 1 H) 4.37 (br s, 1 H) 7.41 (s, 1 H). |
| 64 | ¹H NMR (400 MHz, METHANOL- $d_4$) δ ppm 1.32-1.48 (m, 6 H) 1.51-1.83 (m, 10 H) 2.14-2.21 (m, 1 H) 2.47-2.82 (m, 7 H) 2.82-2.90 (m, 2 H) 2.91-2.99 (m, 1 H) 3.24-3.34 (m, 2 H) 3.42 (d, J = 13.34 Hz, 1 H) 4.34-4.39 (m, 1 H) 7.41 (s, 1 H). |
| 65 | ¹H NMR (400 MHz, METHANOL- $d_4$) δ ppm 1.25-1.47 (m, 6 H) 1.53 (br s, 1 H) 1.57-1.73 (m, 6H) 1.79 (br d, J = 8.41 Hz, 2 H) 1.83-1.95 (m, 4 H) 1.96-2.11 (m, 2 H) 2.40-2.63 (m, 4 H) 2.63-2.80 (m, 3 H) 2.80-2.93 (m, 2 H) 3.50-3.83 (m, 2 H) 7.39 (s, 1 H). |
| 66 | ¹H NMR (400 MHz, METHANOL- $d_4$) δ ppm 1.40 (br s, 4 H) 1.54-1.72 (m, 4 H) 1.72-1.94 (m, 6 H) 1.96-2.22 (m, 2 H) 2.46-2.63 (m, 1 H) 2.63-3.00 (m, 7 H) 3.30 (dt, J = 3.13, 1.57 Hz, 1 H) 3.34 (s, 1 H) 3.45-3.60 (m, 1 H) 3.68 (d, J = 13.60 Hz, 1 H) 4.28-4.43 (m, 1 H) 7.40 (s, 1 H). |
| 67 | ¹H NMR (400 MHz, METHANOL- $d_4$) δ ppm 0.95 (s, 6 H) 1.19 (s, 3 H) 1.37-1.46 (m, 4 H) 1.55-1.73 (m, 8 H) 2.33 (s, 2 H) 2.55-2.73 (m, 5 H) 2.83-2.91 (m, 1 H) 3.24 (s, 2 H) 3.26-3.37 (m, 2 H) 7.32 (s, 1 H). |
| 68 | ¹H NMR (400 MHz, METHANOL- $d_4$) δ ppm 0.86-0.96 (m, 8 H) 1.00 (s, 4 H) 1.36-1.46 (m, 4H) 1.56-1.74 (m, 6 H) 1.99 (br d, J = 11.35 Hz, 2 H) 2.14 (s, 2 H) 2.19-2.32 (m, 2 H) 2.42 (br d, J = 11.25 Hz, 1 H) 2.62-2.90 (m, 4 H) 3.10-3.32 (m, 4 H) 7.25-7.44 (m, 1 H). |
| 69 | ¹H NMR (400 MHz, METHANOL- $d_4$) δ ppm 1.33-1.46 (m, 6 H) 1.46-1.59 (m, 1 H) 1.60-1.75 (m, 9 H) 2.05-2.11 (m, 2 H) 2.40-2.55 (m, 3 H) 2.63-2.83 (m, 3 H) 2.87 (t, J = 6.2 Hz, 2 H) 2.96 (d, J = 10.54 Hz, 1 H) 3.21 (d, J = 13.38 Hz, 1 H) 3.50 (d, J = 13.47 Hz, 1 H) 3.63 (q, J = 7.33 Hz, 1 H) 3.91 (q, J = 6.89 Hz, 1 H) 4.45 (t, J = 5.94 Hz, 1 H) 4.84 (s, 2 H) 7.37 (s, 1 H). |

Pharmacology

Gα16 Assay

Compounds (as well as stereoisomer(s) thereof and/or salt(s) thereof) were tested for CX3CR1 agonism in a cell based assay with fluorescent readout in Agonist Mode in dose response in quadruplicate with intra-plate modality).

Buffers and Reagents.

PBS (D-PBS without calcium and magnesium; EuroClone); Trypsin (Trypsin 0.05%, EDTA 0.02% in PBS; EuroClone); DMSO (Sigma); Standard tyrode buffer: in-house solution (130 mM NaCl, 5 mM KCl, 2 mM CaCl2, 1 mM MgCl2, 5 mM NaHCO$_3$, 20 mM HEPES in water at pH7.4; sterile filtered); Coelenterazine, native (Biosynth); stock 10 mM; Agonist: Recombinant Human Fractalkine (CX3CL1) (PeproTech); stock: 10 μM in standard tyrode buffer+BSA 0.1%; stored at −20° C.

Cell Line.

Human (hCX3CR1), mouse (mCX3CR1), and rat (rCX3CR1) were used for the assay.

Assay Protocol.

Experiments ere performed in 384 MTP format. Cells were seeded at 7,500 cells/well in 25 μl/well complete growth medium without selection antibiotics in 384-well plates. Twenty-four hours later, cells ere assayed for the response to various compounds using the $Ca^{2+}$ sensitive photo-protein stably expressed in the cells as readout.

The experiment was performed in a 384-well format according to the following procedure:

24 h after seeding, pre-incubate the cells at room temperature for 1 hour.

Then remove the culture medium.

Load cells with 20 μL/well of standard tyrode buffer+1 μM ceolenterazine.

Incubate cell plates for 3 hours at RT.

Inject 10 μL/w of 3× concentrated test compounds and controls in assay buffer at the FLIPRTETRA and monitor the kinetic response over a period of 90 seconds.

Data from FLIPRTETRA measurements were analyzed with the Genedata Screener© software. The following examples are meant to illustrate, but in no way to limit, the claimed invention.

TABLE 5

| Example | hCX3CR1 agonism $EC_{50}$ (μM) | mCX3CR1 agonism $EC_{50}$ (μM) | rCX3CR1 agonism $EC_{50}$ (μM) |
|---|---|---|---|
| 1 | 11.5 | 15.7 | 13.9 |
| 2 | 9.3 | 10.3 | 8.5 |
| 3 | 21 | 75.1 | 77.2 |
| 4 | 14.6 | 16.2 | 15.4 |
| 5 | 8.4 | 11.3 | 10.2 |
| 6 | 15.1 | 18.1 | 14.6 |
| 7 | 15.7 | 26.1 | 44.5 |
| 8 | 16.2 | 17.1 | 20 |
| 9 | 11 | 11.8 | 14.9 |
| 10 | 20.5 | 19.4 | 18.8 |
| 11 | 20.5 | 15.4 | 19.6 |
| 12 | 13.3 | 9.1 | 12.2 |
| 13 | 12.3 | 16 | 16.9 |
| 14 | 9.1 | 15.2 | 9.3 |
| 15 | 19.3 | 24.2 | 20 |
| 16 | 13.6 | 102.8 | 19.7 |
| 17 | 11.8 | 18.2 | 15.7 |
| 18 | 11 | 24.9 | 23.7 |
| 19 | 14.3 | 30.6 | 27.9 |
| 20 | 8.8 | 20.9 | 19.2 |
| 21 | 6 | 6.6 | 5.8 |
| 22 | 11.5 | 15.1 | 13.7 |
| 23 | 10.5 | 11.5 | 9.5 |
| 24 | 24.6 | 50.9 | 59.9 |
| 25 | 10.5 | 39.7 | 23.1 |
| 26 | 27.3 | 58.1 | 46.7 |
| 27 | 11.3 | 12.7 | 10.8 |
| 28 | 8.2 | 10 | 9.4 |
| 29 | 18.7 | 46.3 | 47 |
| 30 | 10.2 | 17 | 13.4 |
| 31 | 9.4 | 18.5 | 14.8 |
| 32 | 9.1 | 14.8 | 11.4 |
| 33 | 17.4 | 44.4 | 22.7 |
| 34 | 13.7 | 46.9 | 12.9 |
| 35 | 12.8 | 18 | 12.1 |
| 36 | 9.1 | >100 | >100 |
| 37 | 12.2 | 15 | 11.5 |
| 38 | 10 | 15.8 | 13.1 |
| 39 | 11.1 | 9.6 | 10.9 |
| 40 | 20.8 | 83.8 | 74.9 |
| 41 | 8.6 | 9.4 | 7.4 |
| 42 | 22.6 | >100 | 81.4 |
| 43 | 11.3 | 42.8 | 15.6 |
| 44 | 9.6 | 10.8 | 8.4 |
| 45 | 14.3 | 41.6 | 18.7 |
| 46 | 10.9 | 52.8 | 19.8 |
| 47 | 12.6 | 71.5 | 19.8 |
| 48 | 18.5 | 18.2 | 13.7 |
| 49 | 10 | 8.7 | 6.6 |
| 50 | 15.8 | 45.7 | 43.5 |
| 51 | 15.7 | 15.4 | 34.8 |
| 52 | 19.4 | 25.1 | 19.4 |
| 53 | 8.6 | 48.6 | 33.7 |
| 54 | 16.3 | >100 | >100 |
| 55 | 13.7 | 8.1 | 12.1 |
| 56 | 18.5 | 24.9 | 23.9 |
| 57 | 15.3 | 30.1 | 20.3 |
| 58 | 21.9 | 19.1 | 16.8 |
| 59 | 11.9 | 9.0 | 9.2 |
| 60 | 16.8 | 89.8 | 18.9 |
| 61 | 13.4 | 33.8 | 15.2 |
| 62 | 20.8 | 99.4 | 40.9 |
| 63 | 9.8 | 13.5 | 9.7 |
| 64 | 10.2 | 13.7 | 9.1 |
| 65 | 6 | 9.2 | 7.4 |
| 66 | 16 | 20.4 | 11.4 |
| 67 | 18.3 | 87.1 | 78.9 |
| 68 | 19.7 | >100 | 63 |
| 69 | 18 | 33.6 | 20.4 |
| 70 | 17 | 44.7 | 26.1 |

ChAMPion Assay

Buffers and Reagents.

PBS (D-PBS without calcium and magnesium; EuroClone); Trypsin (Trypsin 0.05%, EDTA 0.02% in PBS; EuroClone); DMSO (Sigma); Tyrode buffer $Ca^{2+}$ free: in-house solution (130 mM NaCl, 5 mM KCl, 1 mM $MgC^2$, 5 mM $NaHCO_3$, 20 mM HEPES (pH 7.4); sterile filtered and autoclaved); Tyrode buffer 10 mM $Ca^{2+}$: in-house solution (130 mM NaCl, 5 mM KCl, 10 mM $CaCl_2$), 1 mM MgCl2, 5 mM $NaHCO_3$, 20 mM HEPES, in water at pH 7.4, sterile filtered); Coelenterazine, native (Biosynth); stock 10 mM; Agonist: Recombinant Human Fractalkine (CX3CL1) (PeproTech); stock: 1 μM in standard Tyrode buffer/BSA 01%; stored at −20° C.

Cell Line.

The final clone for the hCX3CR1 assay was CHO ChAMPion/CX3CR1 K1.6. ChAMPion technology is based on the co-expression of a $Ca^{2+}$ sensitive photoprotein and of a cyclic nucleotide-gated (CNG) channel acting as a cAMP biosensor in a CHO-K1 cell line. CNG channels are non-selective ligand gated cation channels that can be opened by the direct interaction with either cAMP or cGMP, at the intracellular C-terminus site of the channel. Channel opening allows the flux of extracellular calcium into the cell cytoplasm and its transient elevation can be recorded by means of several different calcium indicators. In the chAMPion system, the CNG channel has been modified to display sensitivity to cAMP levels in the physiological range. In addition the calcium influx through the opened channel is immediately detected by the recording of the photoprotein-emitted flash type luminescence signal.

The chAMPion cell line system can monitor the activation of transfected Gαi-coupled receptors, which elicit changes in 3,′5′-adenosine cyclic monophosphate (cAMP) levels, which in turn is responsible for CNG opening and consequent $Ca^{2+}$ influx.

Assay Protocol.

Experiments were performed in 384 MTP format. Cells were seeded at 10,000 cells/well in 25 μl/well complete growth medium without selection antibiotics in 384-well plates. Twenty-four hours later, cells were assayed for the response to various compounds using the $Ca^{2+}$ sensitive photo-protein stably expressed in the cells as readout.

The experiment was performed in a 384-well format according to the following procedure:

24 h after seeding, pre-incubate the cells at room temperature for 1 hour.

Then remove the culture medium.

Load cells with 20 μL/well of $Ca^{2+}$ free tyrode buffer+ceolenterazine 5 μM.

Incubate cell plates for 4 hours at RT.

10 μl/well of 3× concentrated compounds in Ca2+ free tyrode buffer+Forskolin 9 μM (final Forskolin concentration=3 μM) are applied to the cells (at 10 μl/s). Ten minutes later a second injection is performed: 10 μl/well of $Ca^{2+}$ free tyrode buffer+BSA 0.04% (final BSA concentration=0.01%). Twenty minutes later a third injection is performed: 20 l/well of 10 mM $Ca^{2+}$ tyrode buffer (final $Ca^{2+}$ concentration was 3.3 mM) and luminescence is recorded for 90 seconds.

Data from FLIPRTETRA measurements are analyzed with the Genedata Screener© software.

TABLE 6

| Example | hCX3CR1 agonism $EC_{50}$ (μM) |
|---|---|
| 1 | 2.1 |
| 2 | 1.3 |
| 3 | 30 |
| 4 | 2.8 |
| 5 | 1.8 |
| 6 | 4.5 |
| 7 | 9.9 |
| 8 | 11.2 |
| 9 | 4.1 |
| 10 | 12.2 |
| 11 | 6.3 |
| 12 | 6.2 |
| 13 | 2.2 |
| 14 | 1.6 |
| 15 | 2.7 |
| 16 | 6.6 |
| 17 | 1.3 |
| 18 | 0.94 |
| 19 | 1.9 |
| 20 | 1.7 |
| 21 | 4.4 |
| 22 | 1.3 |
| 23 | 1.4 |
| 24 | 10.6 |
| 25 | 0.70 |
| 26 | 4.3 |
| 27 | 13.1 |
| 28 | 0.79 |
| 29 | 4.8 |
| 30 | 0.60 |
| 31 | 0.89 |
| 32 | 0.64 |
| 33 | 4 |
| 34 | 36.5 |
| 69 | 5.5 |
| 70 | 3.1 |

Suchi5 Assay

Buffers and Reagents.

PBS (D-PBS without calcium and magnesium; EuroClone); Trypsin (Trypsin 0.05%, EDTA 0.02% in PBS; EuroClone); Opti-MEM medium (Thermo Fisher); DMSO (Sigma); Standard tyrode buffer: in-house solution (130 mM NaCl, 5 mM KCl, 2 mM $CaCl_2$, 1 mM $MgCl_2$, 5 mM $NaHCO_3$, 20 mM HEPES in water at pH 7.4; sterile filtered); Screen Quest™ Fluo-8 No Wash Calcium Assay Kit (AAt Bioquest®); Lipofectamine® 2000 Reagent (Thermo Fisher); Agonist: Recombinant Human Fractalkine (CX3CL1) (PeproTech); stock: 1 μM in standard Tyrode buffer/BSA 01%; stored at −20° C.

Cell Line.

The final cell line for CX3CR1-Suchi5 assay is HEK/NatClytin/CNG/Suchi5 transiently transfected hCX3CR1 cDNA. In this cell line native Gai signaling is switched to Gaq pathway thanks to the overexpression of a Gaiq chimeric G protein (called Suchi5) to direct Gai activation towards Ca2+ release for measurement.

Assay Protocol.

Experiments are performed in 384 MTP format. Transiently transfected cells are seeded at 20,000 cells/well in 25 l/well Opti-MEM medium without selection antibiotics in 384-well plates. 4-5-hours later 25 μL/well of complete medium with 20% of FBS are added to the cells. Twenty-four hours later, cells are assayed for the response to various compounds using a fluorescent $Ca^{2+}$ sensitive dye (FLUO8-No Wash Dye) as readout.

The experiment is performed in a 384-well format according to the following procedure:

24 h after seeding, remove the culture medium.

Load cells with 20 μL/well of 0.5×FLUO-8 No Wash Dye diluted in assay buffer.

Incubate cell plates for 1 hour at RT.

Inject 10 μL/w of 3× concentrated test compounds and controls in assay buffer at the FLIPRTETRA and monitor the kinetic response over a period of 90 seconds.

Data from FLIPRTETRA measurements are analyzed with the Genedata Screener© software.

TABLE 7

| Example | hCX3CR1 agonism $EC_{50}$ (μM) |
|---|---|
| 1 | 13.9 |
| 2 | 5.4 |
| 5 | 12.9 |
| 13 | 9.6 |
| 15 | 5.5 |
| 21 | 4.7 |
| 23 | 6.5 |
| 25 | 11.8 |
| 27 | 7.5 |
| 28 | 6.7 |
| 30 | 36.1 |
| 31 | 4.7 |
| 32 | 5.8 |
| 41 | 2.5 |
| 45 | 14.1 |
| 46 | 11.8 |
| 47 | 16.4 |
| 48 | 9.9 |
| 49 | 8.9 |
| 50 | 16.1 |
| 51 | 18.4 |
| 52 | 8.4 |
| 53 | 11.8 |
| 54 | 17.4 |
| 55 | 7.1 |
| 56 | 9.6 |
| 57 | 15.6 |
| 58 | 5 |
| 59 | 1 |
| 60 | 10.3 |
| 61 | 6.8 |
| 62 | 12.9 |
| 63 | 9.6 |
| 64 | 8.7 |
| 65 | 8.2 |
| 66 | 7.2 |
| 67 | 14.4 |
| 68 | 19.5 |
| 70 | 9.3 |

GTPγ[$^{35}$S] Scintillation Proximity Assay

Compounds were tested for agonist activity at the mouse and human CX3CR1 receptor using cell membranes from CHO-K1 cells expressing recombinant mouse or human CX3CR1. For agonist testing, membranes are mixed with GDP. In parallel, GTPγ[$^{35}$S] is mixed with the beads just before starting the reaction. The following reagents are successively added in the wells of an Optiplate (Perkin Elmer): 50 μL of test or reference ligand, 10 μL of assay buffer, 20 μL of the membranes:GDP mix, and 20 μL of the GTPγ[$^{35}$S]:beads mix. The plates are covered with a top seal, mixed on an orbital shaker for 2 min, and then incubated for 1 hour at room temperature. Then the plates are centrifuged for 10 min at 2000 rpm, incubated at room temperature 1 hour and counted for 1 min/well with a PerkinElmer TopCount reader.

TABLE 8

CX3CR1 agonism of compounds disclosed herein.

| Compound Name | GTPγ[³⁵S] Assay EC$_{50}$(μM) (E$_{max}$) |
|---|---|
| Compound 1 | Human: 1.3 (60%) |
| | Mouse: 41.4 (44%) |
| Compound 2 | Human: 0.8 (80%) |
| | Mouse: 8.5 (55%) |
| Compound 70 | Human: 4.1 (61%) |
| | Mouse: >50 (26%) |

CX3CR1 Agonists Prevent CX3CR1-Dependent THP-1 Cell Adhesion to HepG2 Cells

This assay measures the adhesion of THP-1 monocytes, which constitutively express CX3CR1, to HepG2 cells, a fractalkine-expressing cell line. Briefly, HepG2 cells were seeded at 80,000 cells per well in 96-well plates and allowed to form a monolayer overnight. The following day, THP-1 cells (at 2×10$^6$ cells/mL) were fluorescently labeled with Calcein-AM (5 μM) and pre-treated with compound at the doses indicated for 30 min. Labeled THP-1 cells were subsequently seeded (50,000/well) into the HepG2-containing plates and incubated for 30 min before imaging for Calcein-AM signal on the INCell Analyzer Imaging System. After four washes, the plates were imaged once again to calculate THP-1 cell adhesion, as measured by the percentage of cells remaining on the plates. Compounds 1 and 2 both prevented THP-1 adhesion to HepG2 cells in a dose-dependent manner (FIG. 1). These agonists behave as functional antagonists in the cell adhesion assay by blocking the interaction between CX3CR1 and fractalkine. Furthermore, this effect was shown to be CX3CR1-dependent in THP-1 cells lacking CX3CR1 expression through genetic manipulation (FIG. 1).

Figure 2:
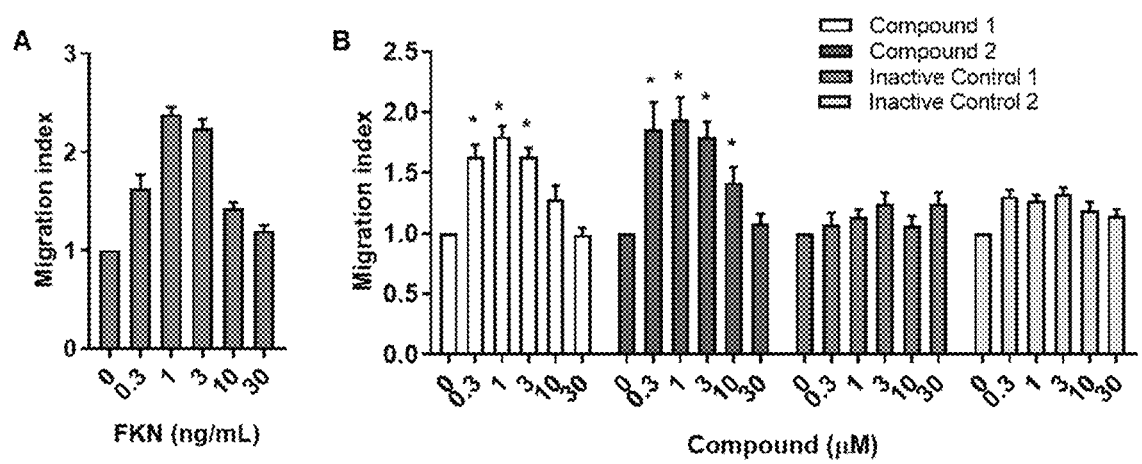
FIG. 2 shows the effect of various concentrations of compounds disclosed herein on fractalkine (FKN, FIG. 2A, left graph) and CX3CR1 agonist-directed (FIG. 2B, right graphs) chemotaxis on primary human monocytes.

Primary Human Monocytes Migrate Along a Chemotactic Gradient Towards CX3CR1 Agonists The chemotaxis assay assesses the CX3CR1-dependent migration of primary human monocytes towards fractalkine and active CX3CR1 agonists. To determine the migration index, monocytes were positively selected from freshly isolated human PBMCs and seeded at 50,000 cells per insert, on the upper chamber of a transwell plate with a pore size of 5 μm. The lower chamber was loaded with recombinant human fractalkine, or active and inactive CX3CR1 agonists at the concentrations shown in FIG. 2. Monocytes were allowed to migrate for 4 hours, and subsequently detected in the lower chamber with the CellTiter-Glo Assay, which measures metabolically active cells. As expected, monocytes migrated towards fractalkine (FIG. 2A), and only towards active CX3CR1 agonists (FIG. 2B), suggesting a CX3CR1-dependent process.

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A compound of the following formula (I)

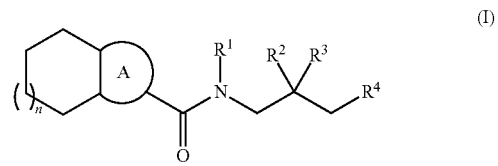

or a stereoisomer thereof, or a salt thereof, wherein:
n is an integer between 1 and 4, forming a 6-10-membered cycloalkyl;
A is chosen from phenyl and heteroaryl, optionally substituted with one or more $C_1$-$C_3$ alkyl substituents;
$R^1$ is chosen from hydrogen and $C_1$-$C_3$ alkyl;
$R^2$ and $R^3$ are joined together via a group Y, such that $R^2$—Y—$R^3$, together with the carbon to which $R^2$ and $R^3$ attach, forms $C_3$-$C_7$ cycloalkyl or $C_3$-$C_7$ heterocycloalkyl, either of which is optionally substituted with one or more substituents chosen from hydroxyl, halogen, and $C_1$-$C_6$alkyl; or the $C_3$-$C_7$ cycloalkyl or $C_3$-$C_7$ heterocycloalkyl is fused with a phenyl ring which is optionally substituted with one or more substituents chosen from hydroxyl, halogen, and $C_1$-$C_6$ alkyl;
Y is chosen from $CH_2$ and O;
$R^4$ is chosen from

(a)

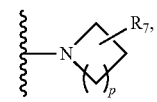

(b)

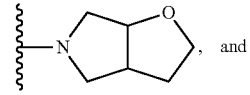

(c)

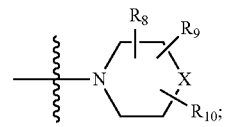

(d)

$R^5$ and $R^6$ are each independently $C_1$-$C_6$ alkyl;
$R^7$, $R^8$, $R^9$, and $R^{10}$ are independently chosen from hydrogen and hydroxyl, or are independently chosen from $C_1$-$C_6$ alkyl and $C_1$-$C_6$ alkyloxy, either of which is optionally substituted with methoxy;
p is 1 or 2; and
X is chosen from $CH_2$, O, or $NR^{11}$ where $R^{11}$ is hydrogen or $C_1$-$C_3$ alkyl.

2. The compound as recited in claim 1, or a stereoisomer thereof, or a salt thereof, wherein A is thiophene.

3. The compound as recited in claim 2, or a stereoisomer thereof, or a salt thereof, wherein $R^1$ is chosen from hydrogen and methyl.

4. The compound as recited in claim 1, or a stereoisomer thereof, or a salt thereof, wherein $R^5$ and $R^6$ are each independently $C_1$-$C_3$ alkyl.

5. The compound as recited in claim 1, or a stereoisomer thereof, or a salt thereof, wherein $R^7$, $R^8$, $R^9$, and $R^{10}$ are independently hydrogen, hydroxyl, $C_1$-$C_3$ alkyl, $C_1$-$C_3$ alkoxy, optionally substituted with methoxy.

6. The compound as recited in claim 1, or a stereoisomer thereof, or a salt thereof, wherein X is chosen from $CH_2$, O, or NH.

7. A compound of the following formula (I)

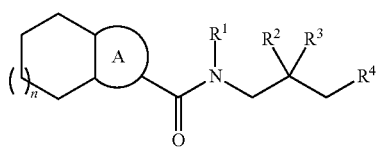

or a stereoisomer thereof, or a salt thereof, wherein:

n is an integer between 1 and 4, forming a 6-10-membered cycloalkyl;

A is chosen from phenyl and heteroaryl, optionally substituted with one or more $C_1$-$C_3$ alkyl substituents;

$R^1$ is chosen from hydrogen and $C_1$-$C_3$ alkyl;

$R^2$ and $R^3$ are joined together via a group Y, such that $R^2$—Y—$R^3$, together with the carbon to which $R^2$ and $R^3$ attach, forms $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl;

Y is chosen from $CH_2$ and O;

$R^4$ is chosen from

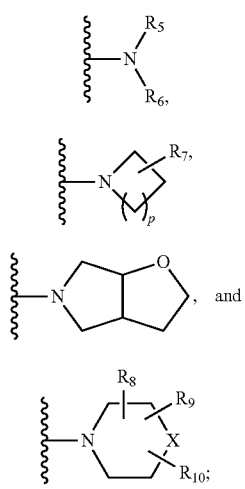

$R^5$ and $R^6$ are each independently $C_1$-$C_6$ alkyl;

$R^7$, $R^8$, $R^9$, and $R^{10}$ are independently chosen from hydrogen and hydroxyl, or are independently chosen from $C_1$-$C_6$ alkyl and $C_1$-$C_6$ alkyloxy, either of which is optionally substituted with methoxy;

p is 1 or 2; and

X is chosen from $CH_2$, O, or $NR^{11}$ where $R^{11}$ is hydrogen or $C_1$-$C_3$ alkyl.

8. The compound as recited in claim 7, or a stereoisomer thereof, or a salt thereof, wherein A is thiophene.

9. The compound as recited in claim 8, or a stereoisomer thereof, or a salt thereof, wherein $R^1$ is chosen from hydrogen and methyl.

10. The compound as recited in claim 8, or a stereoisomer thereof, or a salt thereof, wherein $R^5$ and $R^6$ are each independently $C_1$-$C_3$ alkyl.

11. The compound as recited in claim 8, or a stereoisomer thereof, or a salt thereof, wherein $R^7$, $R^8$, $R^9$, and $R^{10}$ are independently hydrogen, hydroxyl, $C_1$-$C_3$ alkyl, $C_1$-$C_3$ alkoxy, optionally substituted with methoxy.

12. The compound as recited in claim 8, or a stereoisomer thereof, or a salt thereof, wherein X is chosen from $CH_2$, O, or NH.

13. The compound as recited in claim 7, or a stereoisomer thereof, or a salt thereof, wherein:

n is an integer between 1 and 4, forming a 6-10-membered cycloalkyl;

A is thiophene;

$R^1$ is chosen from hydrogen and methyl;

$R^2$ and $R^3$ are joined together via a group Y, such that $R^2$—Y—$R^3$, together with the carbon to which $R^2$ and $R^3$ attach, forms $C_3$-$C_6$ cycloalkyl or $C_3$-$C_6$ heterocycloalkyl, either of which is optionally substituted with one or more substituents chosen from hydroxyl, fluorine, and methyl; or the $C_3$-$C_6$ cycloalkyl or $C_3$-$C_6$ heterocycloalkyl is fused with a phenyl ring which is optionally substituted with one or more substituents chosen from hydroxyl, halogen, and $C_1$-$C_6$ alkyl;

Y is chosen from $CH_2$ and O;

$R^4$ is chosen from

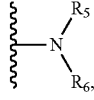

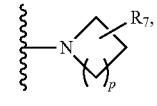

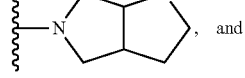

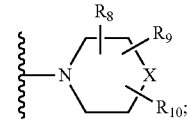

$R^5$ and $R^6$ are independently $C_1$-$C_3$ alkyl;

$R^7$, $R^8$, $R^9$, and $R^{10}$ are independently chosen from hydrogen, hydroxyl, $C_1$-$C_3$ alkyl, and $C_1$-$C_3$ alkoxy, optionally substituted with methoxy;

p is 1 or 2; and

X is chosen from $CH_2$, O, or $NR_{11}$; and $R_{11}$ is $C_1$-$C_3$ alkyl.

14. A compound chosen from any one of
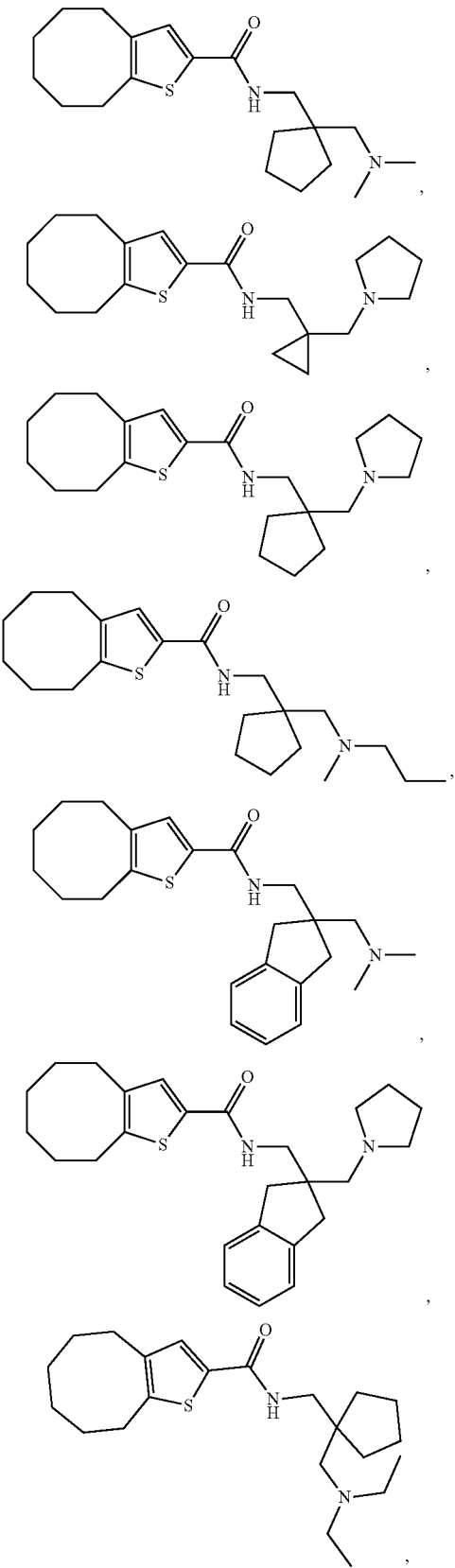
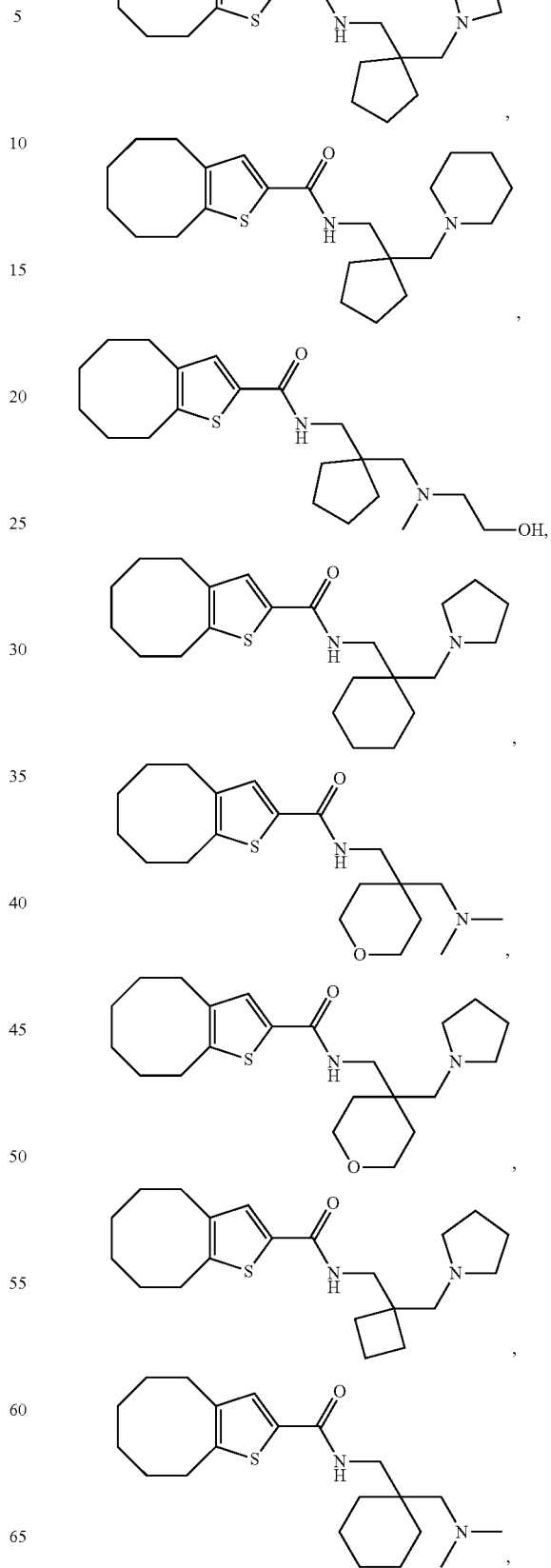

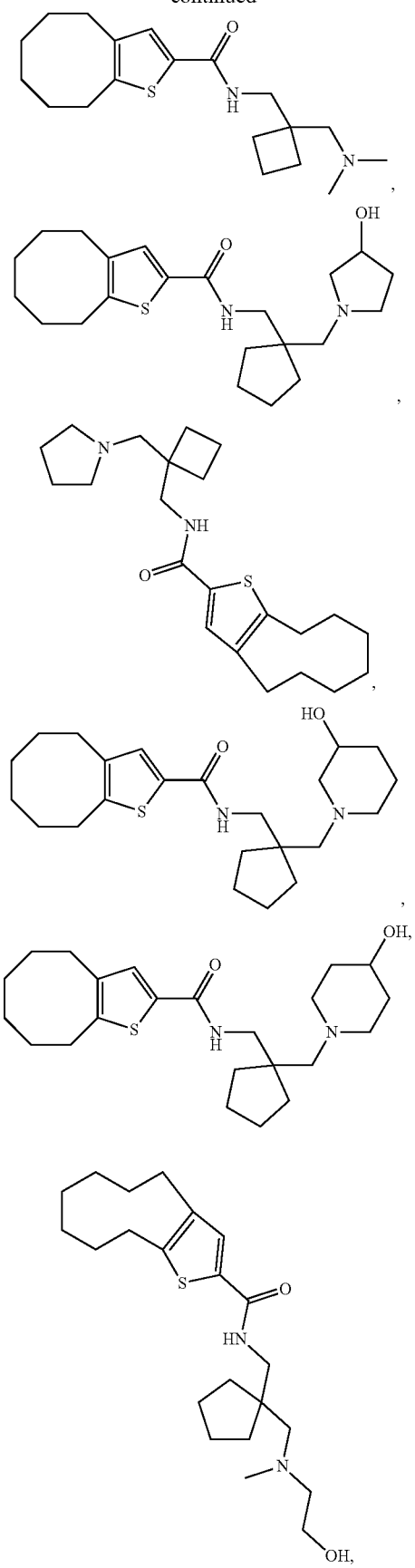
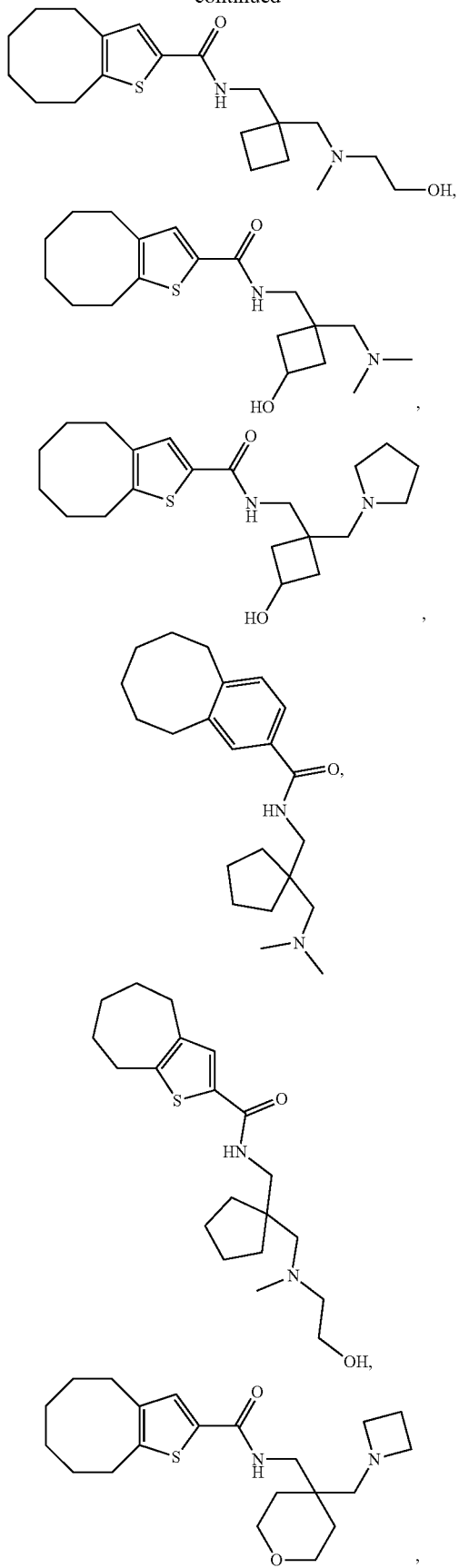

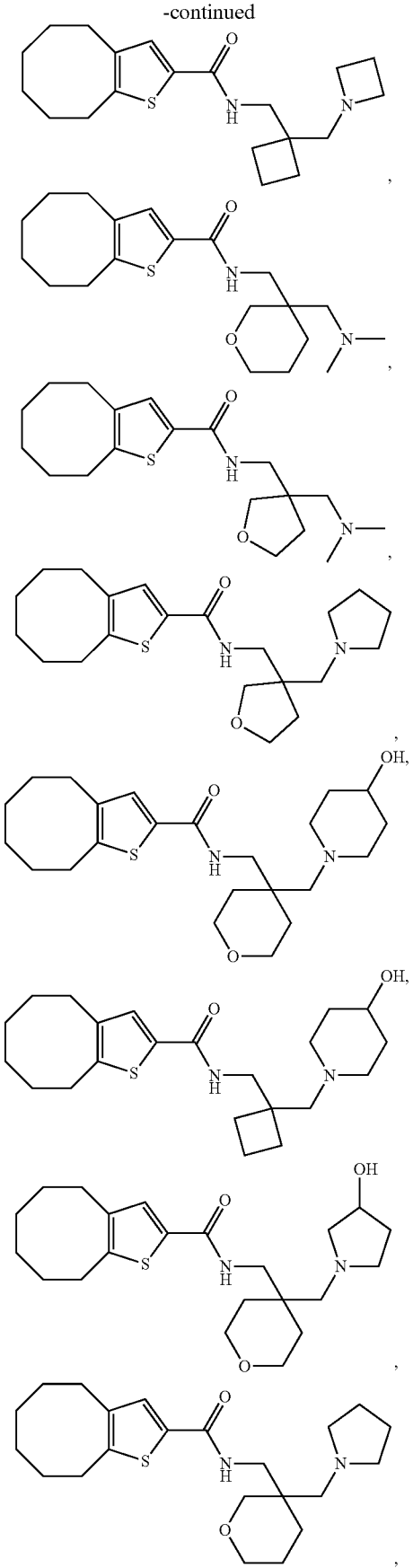
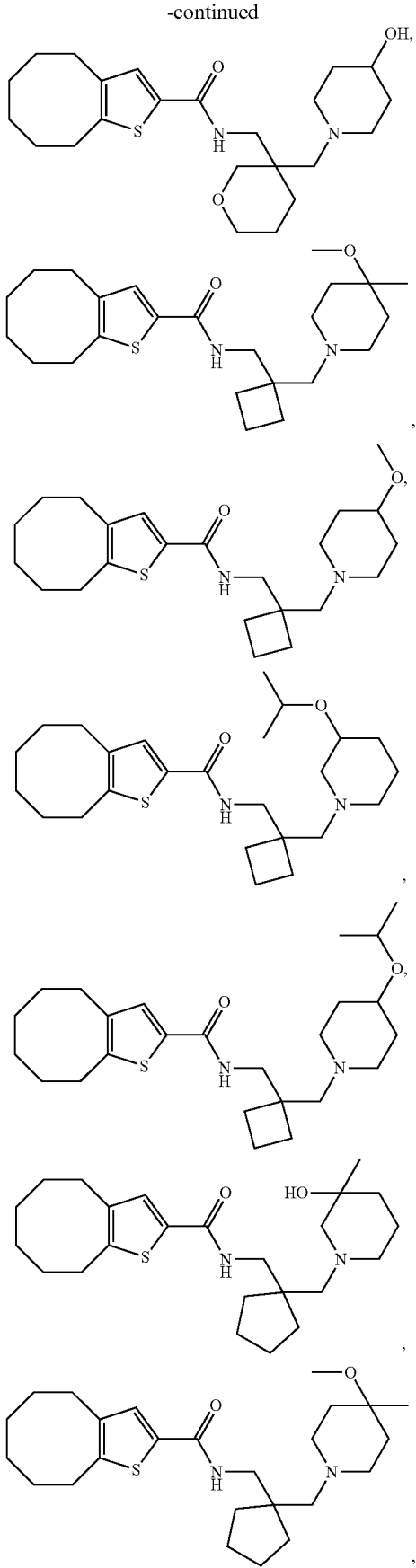

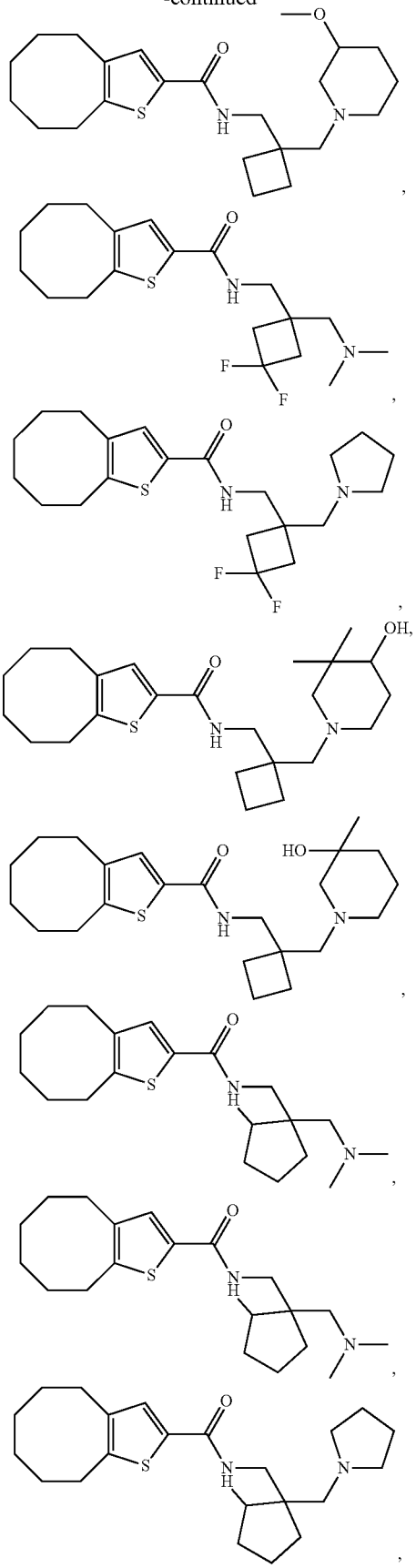

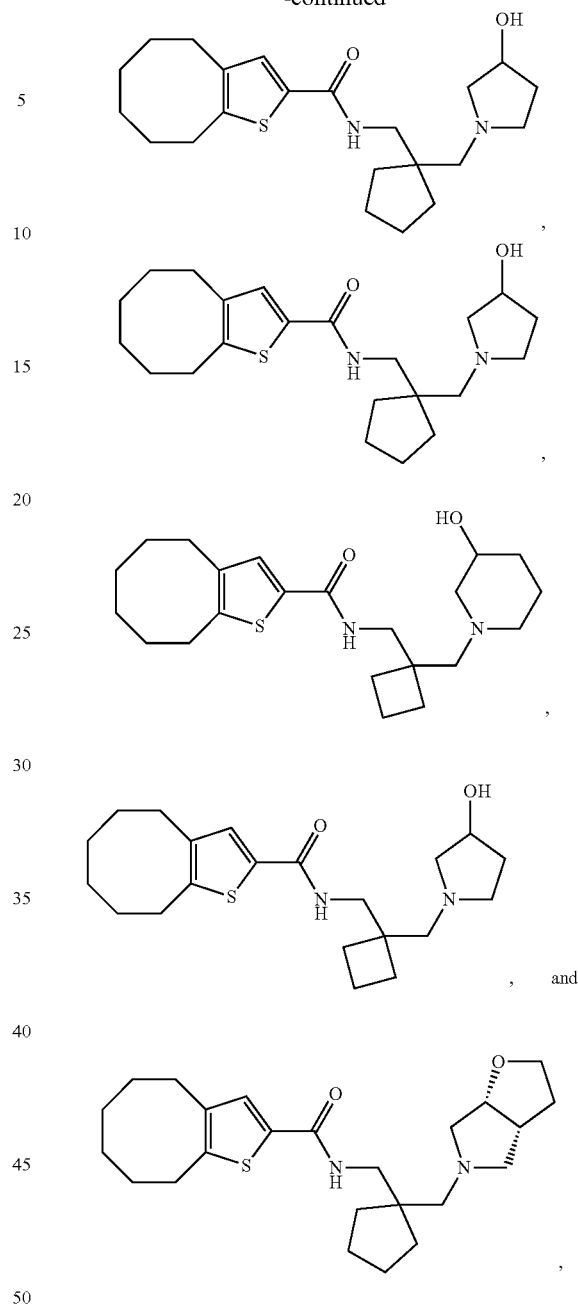

or a stereoisomer thereof, or a salt thereof.

15. A pharmaceutical composition comprising a compound as recited in claim 1, or a stereoisomer thereof, or a salt thereof, together with a pharmaceutically acceptable carrier.

16. A pharmaceutical composition comprising a compound as recited in claim 7, or a stereoisomer thereof, or a salt thereof, together with a pharmaceutically acceptable carrier.

17. A pharmaceutical composition comprising a compound as recited in claim 14, or a stereoisomer thereof, or a salt thereof, together with a pharmaceutically acceptable carrier.

* * * * *